United States Patent [19]

Hepp et al.

[11] Patent Number: 4,751,726
[45] Date of Patent: Jun. 14, 1988

[54] EKG TELEMETRY BASE STATION

[75] Inventors: Dennis G. Hepp, Coon Rapids; Paul J. Beckmann, St. Paul; Thomas C. Evans, Fridley; Robert A. Neumann; Maynard J. Hoffman, both of Blaine; Thomas L. Jirak, Plymouth, all of Minn.

[73] Assignee: Futurecare Systems, Inc., Minneapolis, Minn.

[21] Appl. No.: 838,997

[22] Filed: Mar. 10, 1986

[51] Int. Cl.⁴ .......................................... H04M 11/00
[52] U.S. Cl. ....................................... 379/93; 379/38; 379/106
[58] Field of Search ........... 179/2 A, 2 DP; 128/904, 128/903; 379/93, 97, 98, 104, 106, 38

[56] References Cited

U.S. PATENT DOCUMENTS

| | | |
|---|---|---|
| 3,872,251 | 3/1975 | Auerbach et al. ............ 179/2 A |
| 3,872,252 | 3/1975 | Malchman et al. ............ 179/2 A |
| 3,882,277 | 5/1975 | De Pedro et al. ............ 379/106 |
| 3,885,552 | 5/1975 | Kennedy ................... 128/904 |
| 4,004,577 | 1/1977 | Sarnoff ................... 128/904 |
| 4,173,971 | 11/1979 | Karz ...................... 128/904 |
| 4,428,381 | 1/1984 | Hepp ...................... 128/904 |

Primary Examiner—James L. Dwyer
Attorney, Agent, or Firm—Kinney & Lange

[57] ABSTRACT

A telemetry base station for use in a system also including a patient worn EKG monitor and transmitter, and a physician monitoring station. The base station is microprocessor controlled, and includes a receiver for receiving FM EKG transmissions from the patient transmitter, an A to D converter, a conventional telephone set, used as an intercom to communicate with the physician, and a data modem which is used for digitized transmissions of the EKG signals. Base station functions including selection of data or voice transmission are controlled by a physician monitoring station. The base station includes simulated telephone ringing functions which assist in its use by patients without specialized training.

3 Claims, 13 Drawing Sheets

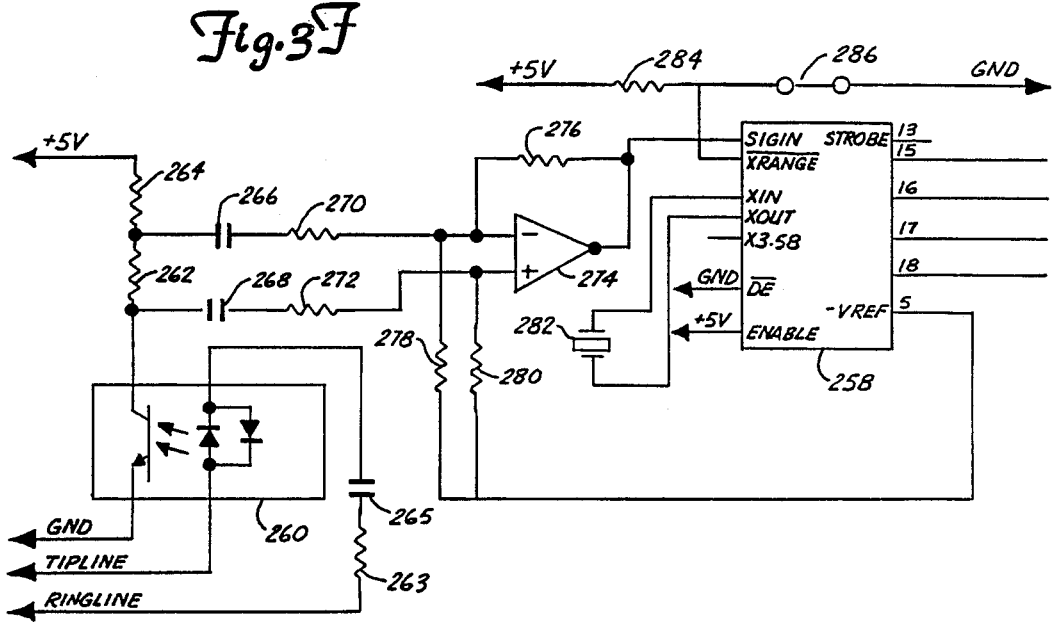

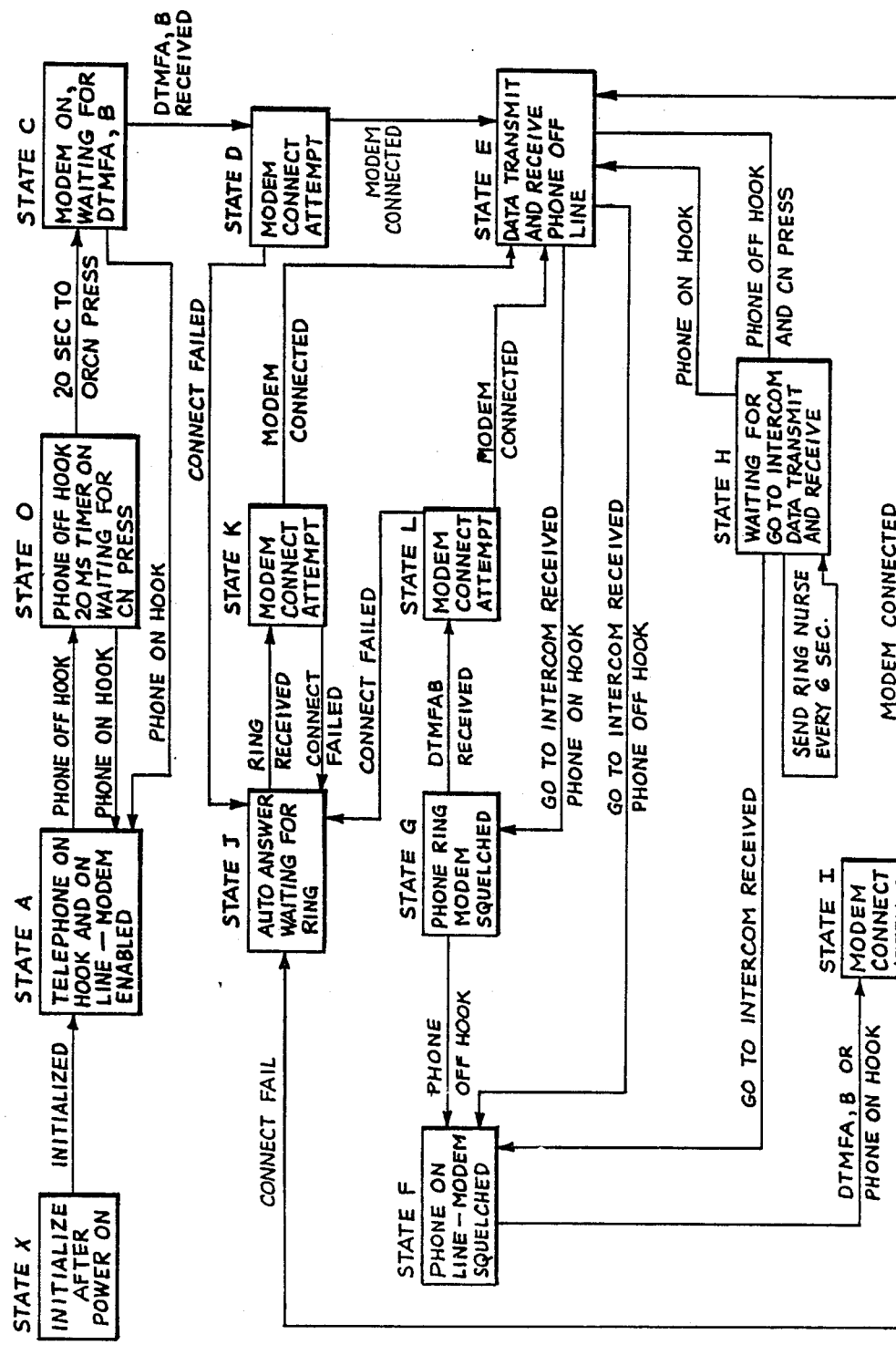

EKG TELEMETRY BASE STATION

BACKGROUND OF THE INVENTION

The present invention relates generally to EKG and patient monitoring systems, and in more particularity to telephonic electrocardiogram monitoring.

Transtelephonic EKG monitoring has become routine for patients with implanted pacemakers. Typically, such monitoring is short-term, and involves the patient contacting the physician by phone, and employing an EKG transmitter of the type described in U.S. Pat. No. 4,151,513, issued to Menken et al. Use of such device typically requires the patient to apply EKG electrodes to his or her body, and to subsequently couple the monitoring device to their telephone to allow for a brief period of monitoring.

Long-term monitoring has typically been accomplished by means of a holter monitor, or similar device, which stored long sequences of EKG strips either on magnetic tape or in a digital memory as described in U.S. Pat. No. 4,360,030 issued to Citron et al. With such systems, the physician typically does not have the ability to monitor the patient's condition in real time. As such, when long-term real time monitoring is required, patients often must remain in the hospital.

SUMMARY OF THE INVENTION

The present invention provides a system which allows for continuous long-term transtelephonic EKG monitoring. This system provides the benefits of long-term EKG monitoring without requiring that the patient remain in the hospital.

The system includes a patient worn EKG monitor and transmitter. This small, battery-powered device is worn by the patient during the intended period of monitoring, and provides an FM modulated EKG signal. In addition, the transmitter provides 2 KHz tone bursts superimposed over the EKG signal in the event of either a sensed pacemaker spike, or the pressing of a patient alert button on the transmitter.

The base station includes an FM receiver which receives the transmitted EKG and 3 KHz bursts. The base station includes an A/D converter and a modem, both under microprocessor control, and sends a digitized version of the EKG, along with the pacing spike and patient alert indicators to the physician's monitoring station where they may be displayed and analyzed. In addition, the base station includes a telephone set which allows the patient to speak to the physician.

The base station is designed to allow operation by a patient with a minimum of training. When the base station is initially powered up and coupled to the patient's telephone line, it simply functions as a telephone. This allows the patient to contact the physician or the physician to contact the patient in order to begin the monitoring procedure. Once the monitoring procedure has begun, the telephone is disconnected from the telephone line, and the base station is coupled to the physician monitoring station by means of a 1200 baud modem. While coupled, operation of the base station is under control of the physician's monitoring station. The base station may be instructed to couple the telephone to the phone line to serve an intercom function, to provide a calibration signal, to adjust the gain of the EKG signal, to transmit a measured pacing rate, and to perform various other functions.

One important feature of the base station is that in the event the patient desires to contact the physician during EKG monitoring, the patient need only remove the hand piece of the telephone set and press a call nurse button. This will initiate a digital transmission to the physician's base station indicating that voice communication is desired. While the base station waits for a response, it causes a simulated ringing signal in the earpiece of the base station telephone set. However, digital EKG transmission continues uninterrupted until and unless the physician elects to initiate voice communication and use the intercom function. Similarly, when the physician desires to contact the patient, although the telephone portion of the base station is not connected to the phone line, a telephone ring occurs to signal to patient that voice communication is desired. This simulated telephone function is believed to be particularly beneficial in that it is easily understood by and familiar to almost all potential patients.

The structure and functioning of the base station is described in more detail in the following brief and detailed descriptions of the drawings.

BRIEF DESCRIPTION OF THE DRAWINGS

FIGS. 3A through 3I are schematic drawings of the circuitry within the base station.

FIG. 4 is a state diagram illustrating the basic functional operation of the base station.

DETAILED DESCRIPTION OF THE DRAWINGS

Figure 1:
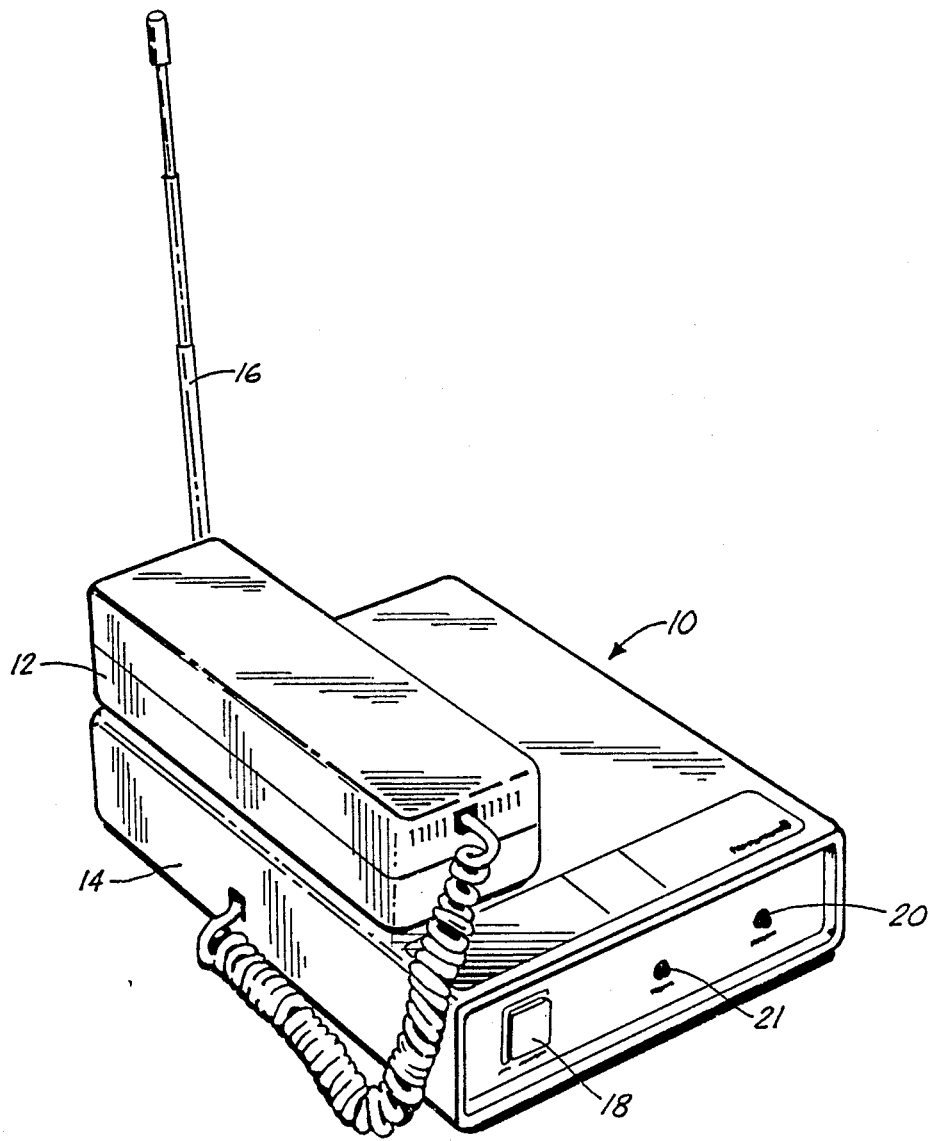
FIG. 1 is a plan drawing of the base station.

FIG. 1 is a plan drawing of the telemetry base station. The base station 10 includes an external telephone 12 coupled to the base station by means of a standard, modular telephone jack 14. This station also includes a telescoping antenna 16 which is coupled to the RF receiver within. On the front of the base station are a Call Nurse button 18 and two indicator lights 20 and 21 which indicate that the unit is transmitting information, or that the Call Nurse button 18 has been pressed, respectively. On the back of the unit, not visible in this drawing, are two standard modular telephone jacks, one of which is used to couple the base station 10 to the patient's telephone line.

Figure 2:
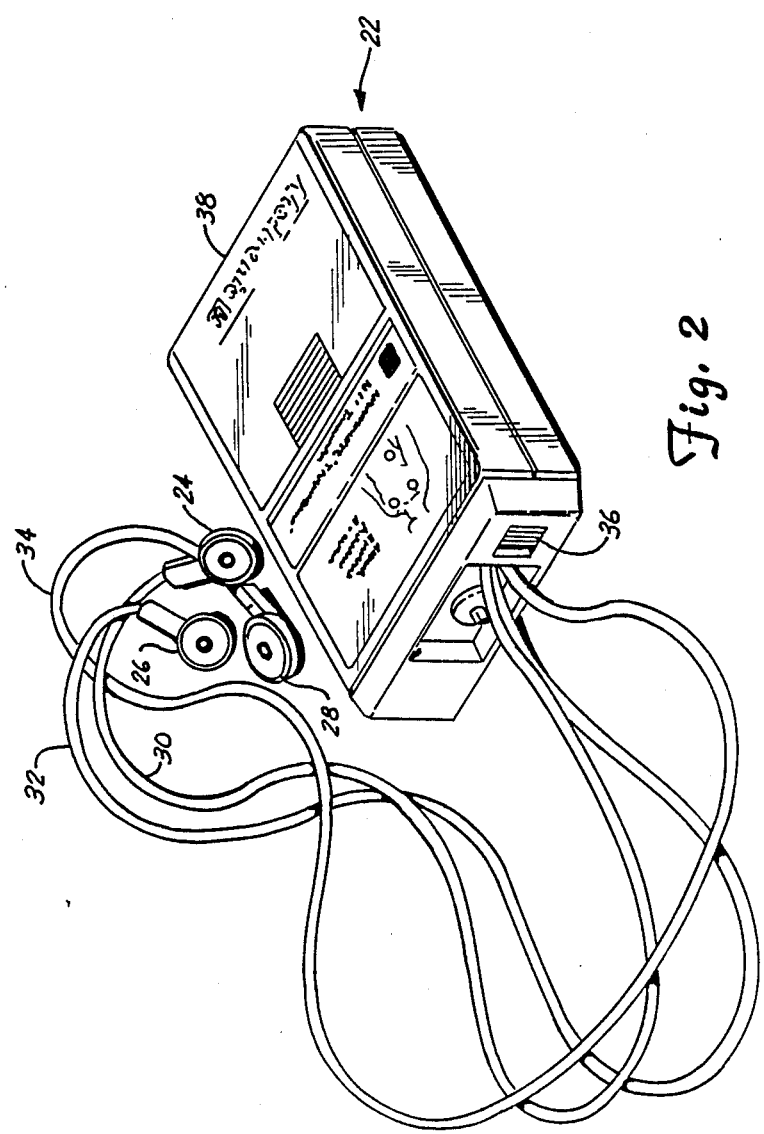
FIG. 2 shows a plan drawing of the patient transmitter.

FIG. 2 is a plan drawing of the patient transmitter. The transmitter 22 is intended to be coupled to three EKG electrodes by means of snap connectors 24, 26 and 28, mounted to conductors 30, 32 and 34, respectively. The device includes a patient alert button 36 which the patient may press in the event that the patient perceives some cardiac abnormality or related sympton, such as shortness of breath, dizziness, etc. The device is battery-powered, with batteries accessible to the patient via battery cover 38.

In use, three EKG electrodes are attached to snap connectors 24, 26 and 28, and placed on the upper right chest, upper left chest and lower right chest, respectively. The transmitter provides an FM modulated output signal with a center frequency of about 216 MHz, around which the EKG signal is modulated. In the event that the device detects a pacemaker spike, a 10 msec., 2 killocycle tone is sent to the FM modulator, and it is superimposed over the EKG signal. In the event that the patient alert button 36 is pressed, a 60 msec., 2 killocycle tone is provided to the FM modulator within the transmitter, and is superimposed over the electrocardiogram signal. As will be discussed below, these three killocycle tones are digitized by the base station, and are distinguished by their differing durations.

FIGS. 3A through 3I illustrate the circuitry within the base station. The circuitry is comprised of generally available integrated circuit chips, and is discussed in more detail below. For reference purposes, a parts list is provided following the written description of the circuitry.

Figure 3A:
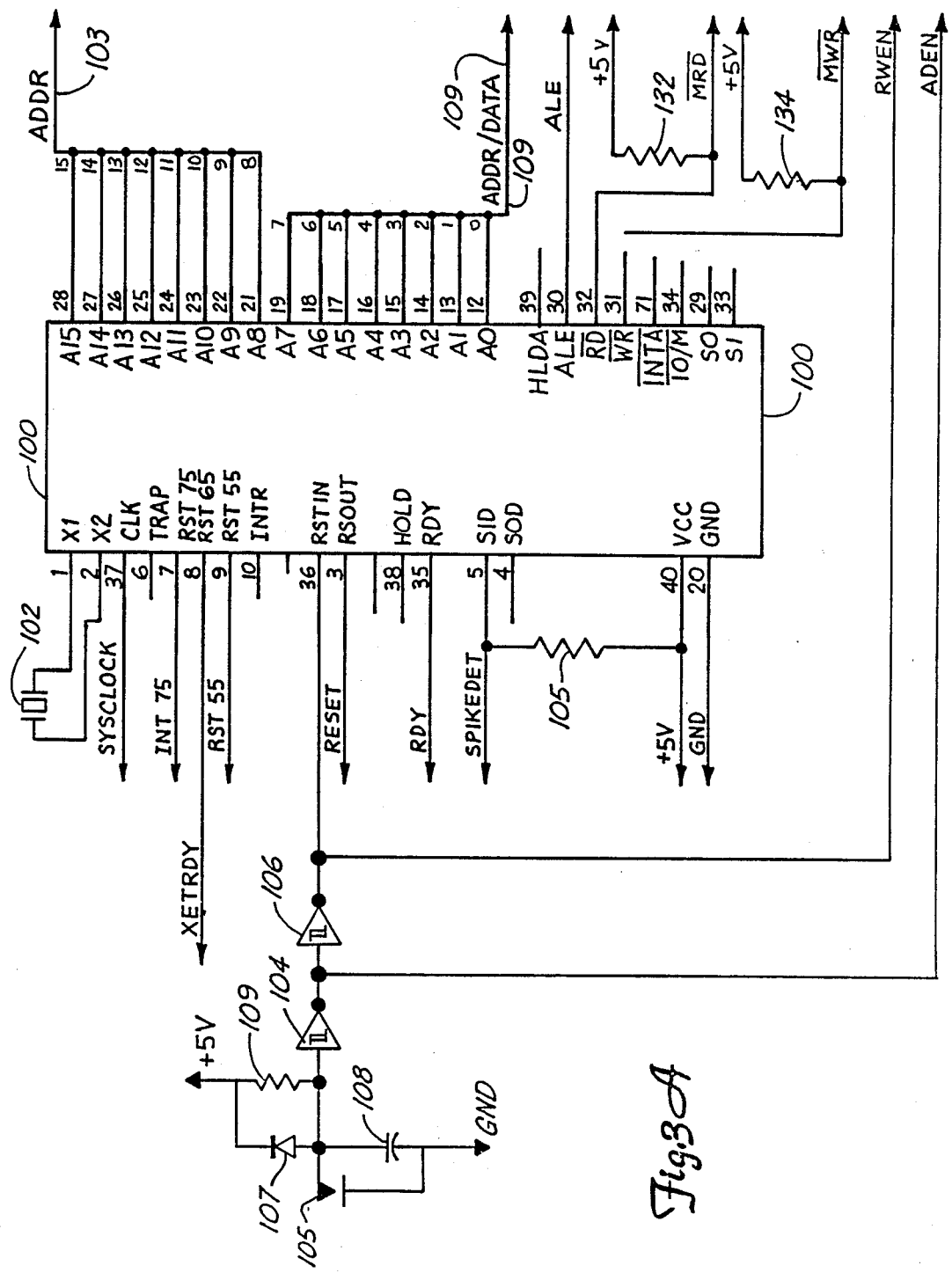

FIG. 3A illustrates the microcomputer chip 100 and its associated reset circuit. Timing functions are accomplished using a 6.00 MHz crystal 102. The power-up reset, which resets microcomputer 100 at either power-up or a push-button reset via reset button 105, is controlled by inverters 104, 106. Capacitor 108 charges via resistor 109 at power-up and holds the pin 36 (RESET IN) of microcomputer 100 low until it charges up, giving the internal circuitry of the chip enough time to reinitialize. Microcomputer 100 as illustrated is an Intel 8085 processor chip.

Figure 3B:
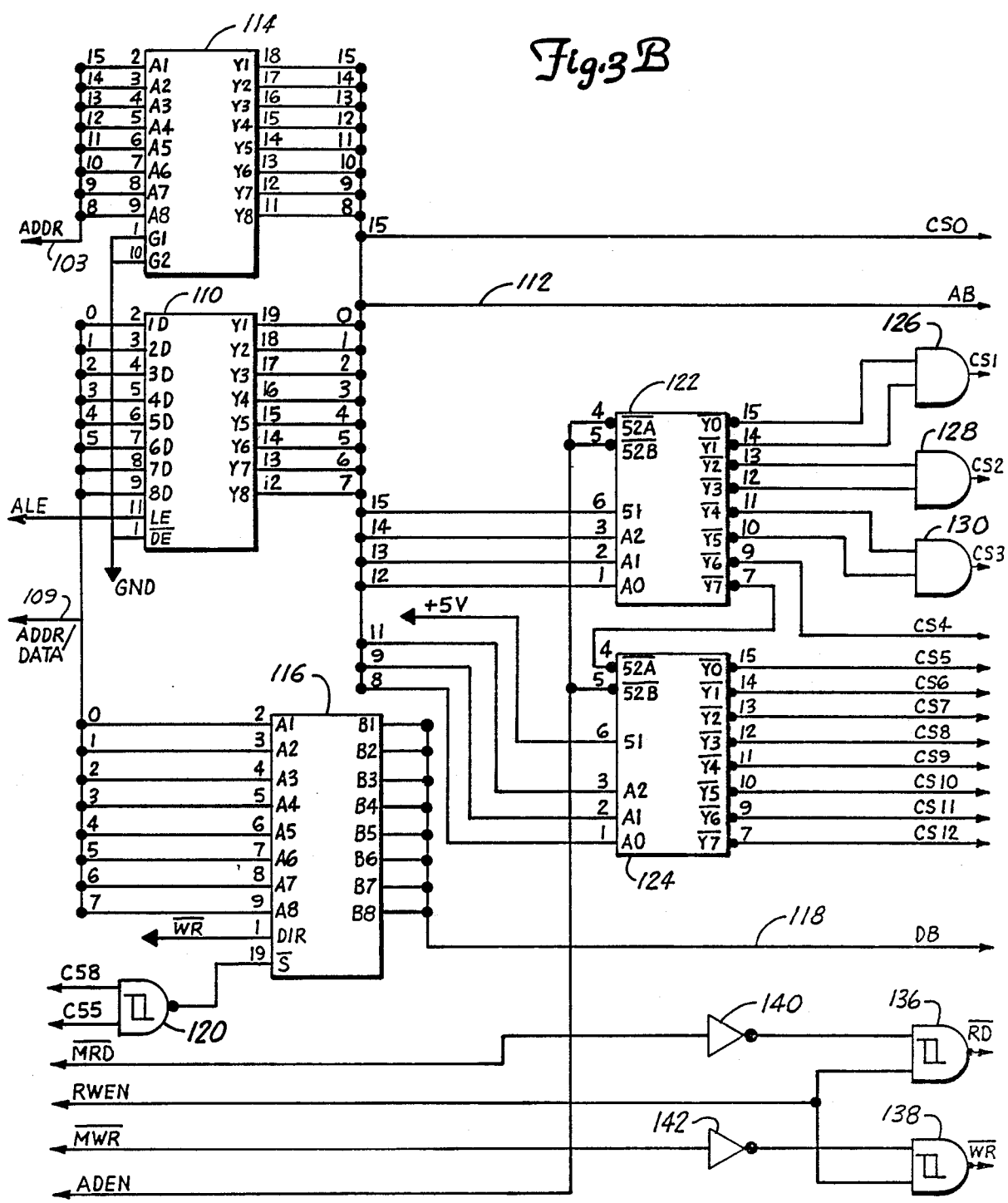

FIG. 3B illustrates the circuitry controlling the addressing functions performed by microcomputer 100. Microcomputer 100 has a multiplex bus in which the data lines and the low order address lines are multiplexed on pins 12–19, coupled to the data/address bus log 109.

In order for the microcomputer 100 to operate, the address and data lines are separated out by latch chip 110. Each address cycle, the low address lines are latched by latch chip 110 and coupled to the address bus 112. Driver chip 114 increases the drive capability of the upper order address lines. Buffer chip 116 is used to increase the drive capability of the eight data lines from microcomputer 100 and is coupled to the data bus 118. NAND gate 120 enables buffer chip 116 only during memory read and write cycles.

Figure 3C:
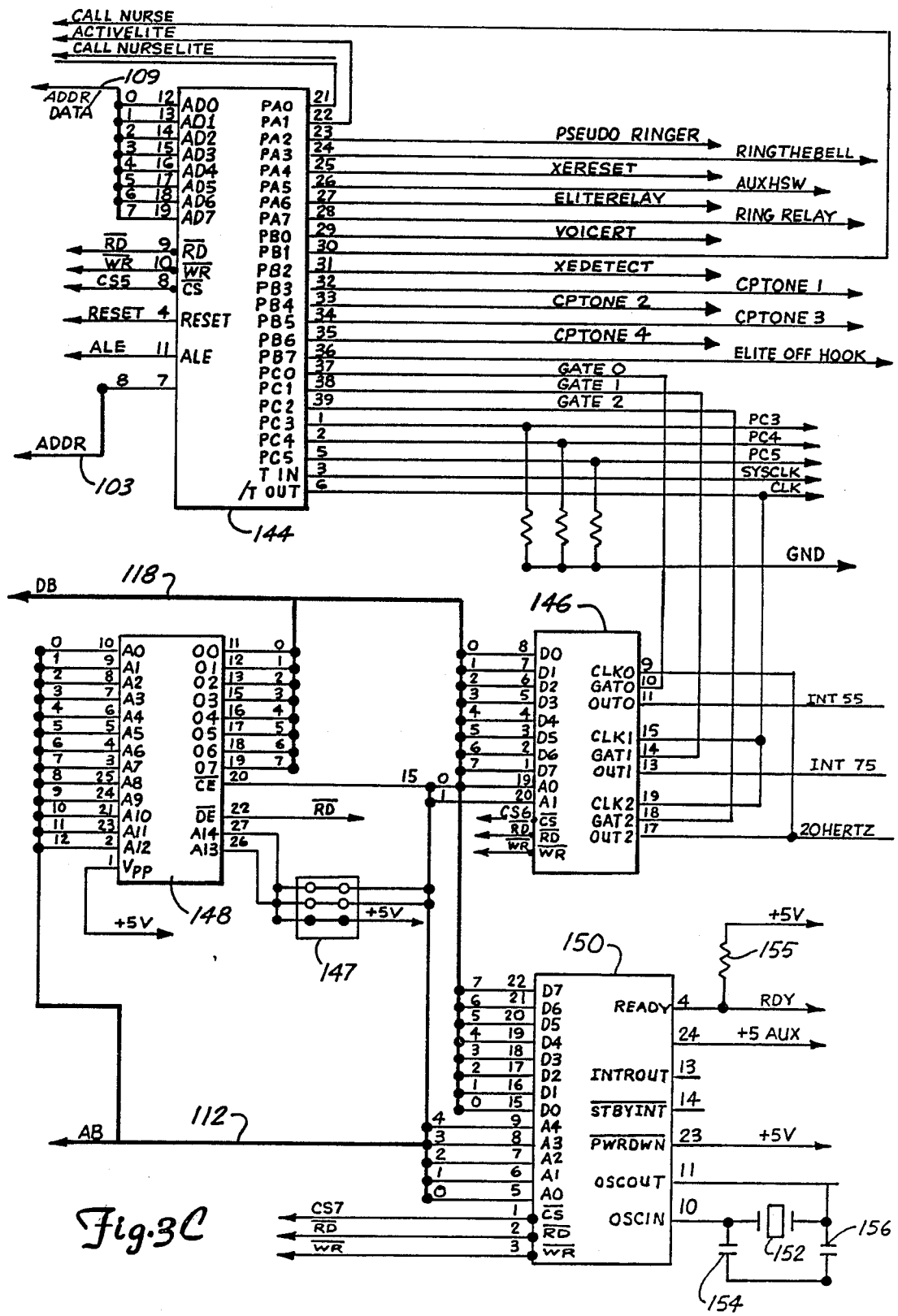

Selection of memory chips and memory mapped input/output devices is done via decoder chips 122 and 124. Both decoders 122 and 124 are one of eight line decoders. Decoder chip 122 is used to select among the random access and read only memory chips (FIG. 3C). AND gates 126, 128 and 130 are used to further decode the addresses for the RAM and ROM chips. Decoder 124 is the I/O decoder which accepts the high order address lines and divides them into individual banks of I/O addresses to enable input to and output from the various circuit chips. Resistors 132 and 134 are pull-up resistors to hold the read (RD) and write (WR) lines decoded by NAND gates 136 and 138 high between read and write cycles, a facility which the microcomputer 100 does not provide. Inverters 140 and 142 are hysteresis inverters which buffer and invert the RD and WR lines prior to driving NAND gates 136 and 138 which in turn gate the RD and WR lines to the power-up reset circuitry. NAND gates 136 and 138 ensure that during power down conditions when the RAM chips (FIG. 3C) are powered off of the internal battery (FIG. 3H), no spurious red and write signals will be applied to the RAM chips.

FIG. 3C illustrates Input/Output RAM and timer chip 144 and associated circuitry. This chip contains 256 bytes of RAM, a 14-bit binary counter, and 2½ 8-bit input/output port chips. The clock signal for the internal timer is provided by the clock out/pin 37 of microcomputer 100. The internal timer provides a 1.5 MHz CLK signal on pin 8 which is used as a base timing signal through the rest of the circuitry. Port A including pins 21–28 of chip 144 is configured as an output port used to drive various I/O devices which will be discussed individually. Port B including pins 29–36 of chip 144 is configured as an input port which is used to take various input signals and supply them to the microcomputer 100. Port C including pins 37–39, 1, 2 and 5 of chip 144 is used as an output port which again controls various functions of the circuitry.

Timer chip 146 is a triple timer chip. This chip takes the CLK signal at 1.5 MHz and in turn creates three separate timing signals. A 20 Hz signal used for internal timing and also to control the ringing functions is provided on pin 17 of chip 146. A 300 Hz timing signal which is a 3.3 msec.interrupt for the microcomputer 100 and is the basic analog sampling signal for the system is provided on pin 13. A 1 Hz timing signal is provided on pin 10 and is used whenever intervals of 1 second or more are required. Output of timing signals on pins 17, 13 and 10 are controlled by pins 37–39 of I/O chip 144.

Memory chip 146 is a read only memory chip. The socket for chip 146 is configured via a jumper block 147 to be able to accept various types of read only memory chips including 8 K, 16 K and 32 K byte ROM chips. Real time clock chip 150 functions as a real time clock source. It is programmed and set by microcomputer 100. Real time clock chip 150 employs its own 32.768 Killocycle crystal source including crystal 152 and start-up capacitors 154 and 156 and maintains the real absolute time independently of whether or not the unit is powered.

Figure 3D:
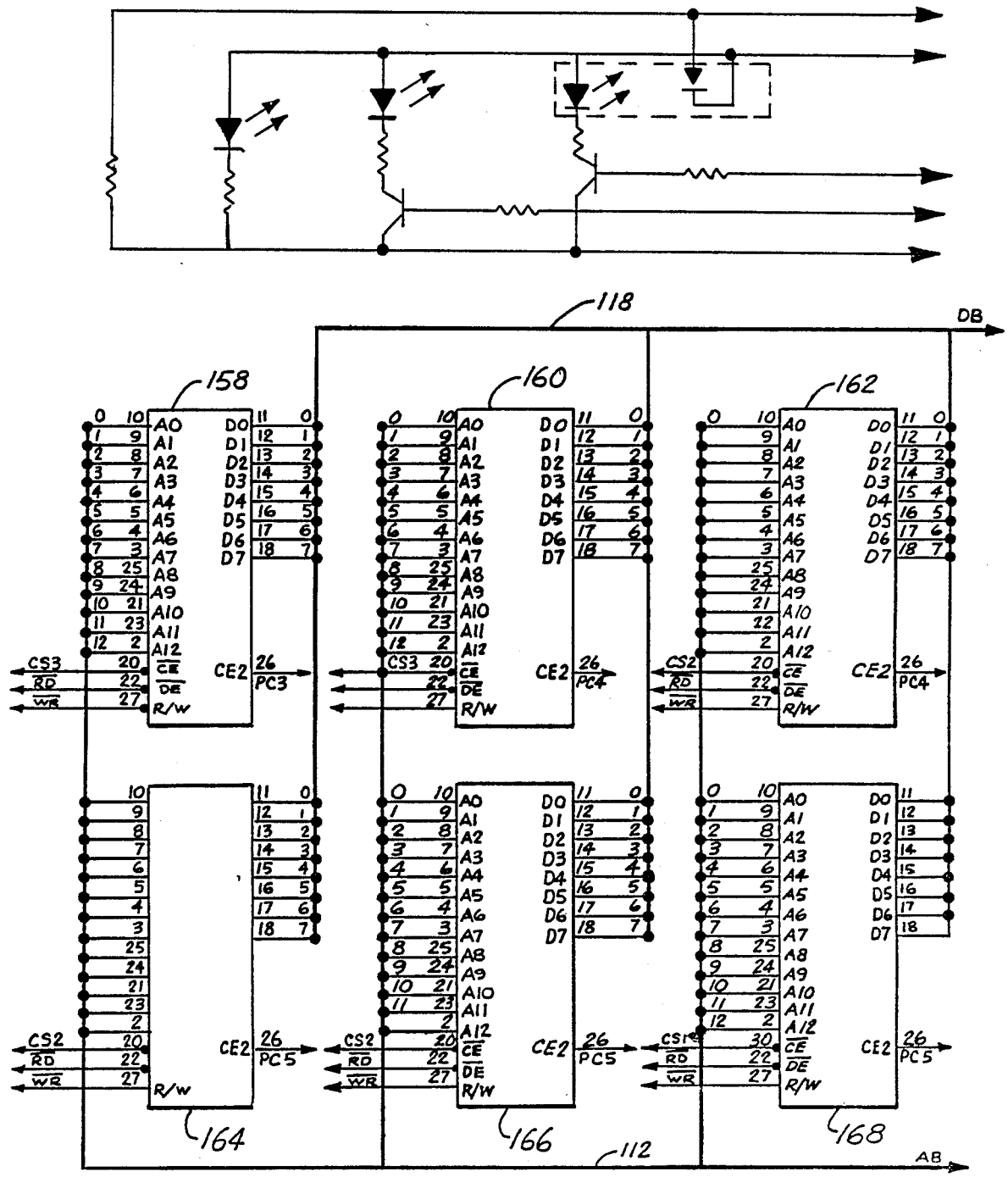

FIG. 3D illustrates chips 158, 160, 162, 164, 166 and 168 which are 8 K by 8 random access memory chips. Chip 168 is the fixed random access and temporary storage memory chip for the entire system and is used for temporary storage of variables. The remainder of the random access memory chips are selected using output port lines PC3, PC4 and PC5 from pins 1, 2 and 5 of chip 144.

In FIG. 3DD, LED's 170 and 172 correspond to the power on and data transmitting indicator LED's 20 and 21 (FIG. 1). Power LED 120 is on whenever power is available in the unit. LED 172 is controlled by the ACTIVELITE line from pin 22 of I/O chip 144 and is turned on via driver transistor 174. Switch 184 is a momentary push-button switch with an integral light emitting diode 186 and corresponds to Call Nurse switch 18 (FIG. 1). The light emitting diode 186 is controlled by transistor 188, controlled by the CALLNURSELITE line from pin 21 of I/O chip 144. Switch 184 is read by microcomputer 100 via pin 30, I/O chip 144.

Figure 3E:
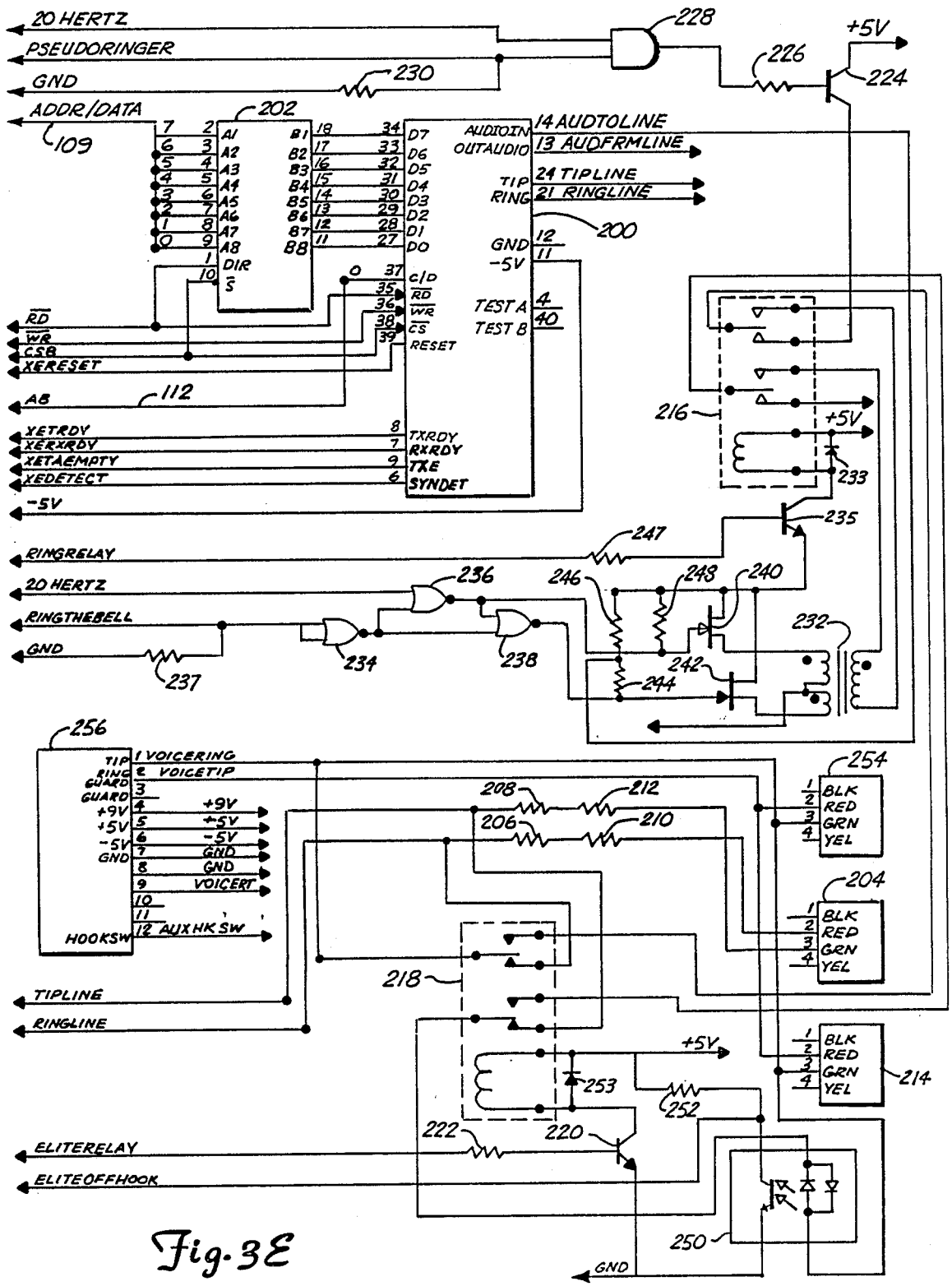

FIG. 3E illustrates the telephone interconnect section of base station 10. Modem chip 200 is a self-contained 1200 baud modem. This module functions as a complete Bell 212A and Bell 103A compatible modem which can be directly interfaced to a microcomputer bus, and also allows direct connection to a telephone line on the public switch network with pass through FCC registration. The modem chip 200 also has audio output and inputs to allow analog audio signals to be coupled into the phone line via microcomputer control. Modem chip 200, as illustrated, is an XE 1203 modem chip manufactured by XECOM, Inc., Milpitas, CA.

Octal buffer chip 202 is used to buffer the data lines going into the modem 200 and to provide additional digital drive capability and isolation. Buffer chip 202 is a bidirectional bus buffer allowing both reading and writing of data to the unit. Buffer 202 interfaces directly to the microcomputer 100 via multiplexed Address-/Data Bus 109, and uses the chip select pin 38 to read and write. The hardware reset pin 39 is controlled by the XERESET line from pin 25 of I/O chip 144. This provides microcomputer 100 with hardware reset control of the modem 200.

Jack 204 is the main phone line connection of the base station 10 to the external telephone line. Standard tip and ring connections are used. Pins 1 and 4 of the Jack 204 are not connected. Inductor 206 and resistor 208 and inductor 310 and resistor 212 are series components used for surge protection between modem 200 and the telephone line. These are standard telephone industry interconnect components. Jack 214 is a two conductor four position RJ type connection jack which is used to connect the internal circuitry to the external telephone 12 (FIG. 1) mounted to the top of base station 10. External telephone 12 is not continuously connected to the telephone line, but is connected selectively to the telephone line via relay 218 controlled by microcomputer 100. When relay 218 is unenergized in the normally closed position, telephone 12 is connected directly to jack 204. This connection allows the base station 10 to function as a standard telephone set when the unit is unpowered or if it should lose power for any reason. Relay 218 is energized by transistor 220, controlled by the ELITERELAY line from pin 27, I/O chip 144. When relay 218 is energized, telephone 12 is disconnected from the telephone line and connected to relay 216. Relay 216 in the normally closed position connects the telephone set to a pseudo ring circuit. The pseudo ring circuit is composed of transistor 224, resistor 226, and AND gate 228 and allows a simulated ringing sound to occur in the hand set of telephone 12. The pseudo ring circuit is controlled by the PSEUDORINGER line from pin 23 of I/O chip 144. The patient hears a simulated ring back suggesting that the phone is ringing at the physician's monitoring terminal. In reality, only a digital control signal has been sent and EKG transmission continues across the telephone line. When the pseudo ring function is enabled by the PSEUDORINGER line, the 20 Hz signal which originates at pin 17 of timer chip 146 is applied to relay 216 by AND gate 228 and thereby applied to telephone 12 via relay 218 and jack 214.

When relay 216 is in the energized position, telephone 12 is disconnected from the pseudo ring circuit and connected via relay 218 to transformer 232. Transformer 232 is used to create a high voltage signal of 250 volts AC which is used to ring the ringer inside the telephone 12. The ring signal is created via the 20 HERTZ line from timer chip 146, gated with the RING THE BELL signal from pin 24 of I/O chip 144 through series of NOR gates 234, 236 and 238. The 20 Hz signal is fed to power FETs 240 and 242 which provide the primary drive circuit to transformer 232, the secondary of which creates the 250 volt ringing signal at 20 Hz which is provided to telephone 12. Telephone 12 will ring only when it is in the on hook position with the hook switch closed either in the cradle or with the hook switch depressed by the patient when holding it in the patient's hand which is standard telephone set function. Jack 204 is coupled to the hook switch of telephone 12 via optical isolator 250 which is powered through resistor 252. When the telephone 12 is in the on hook position and presents a high impedance, the signal out of optical isolator 250 is high. When telephone 12 goes off hook, it presents a low impedance and the signal from optical isolator 250 goes low. The signal on the ELITEOFF hook line from optical isolator 250 is read by microcomputer 100 through pin 36 of I/O chip 144.

A second jack 254 is provided which allows a second telephone line to be connected to the unit. In some clinical applications, the base station is used on two telephone lines simultaneously. Typically, in such an application, a 49 MHz full duplex cordless voice system is added to the unit. In this application, relay 218 is not installed in the unit and telephone 12 is continuously connected to Jack 204. In such application, connector 256 would connect jack 254 to the 49 MHz cordless phone base circuitry and would provide power and ground voltages and a digital signal to control the hook switch. The hook switch control is provided by the AUXHKSW line coupled to pin 26 of I/O chip 144. When relay 218 is not installed in the unit, telephone 12 is effectively isolated from all other circuitry except jack 204 and is not under any control of microcomputer 12.

FIG. 3F illustrates detection chip 258 and its associated circuitry. Detection chip 258 is a Teltone M981 call progress tone detection chip which allows microcomputer 100 to assess the operating condition of the telephone line. An optical isolator 260 is used in parallel across jack 204 and processes the sounds which come across the line via resistors 262, 264, capacitors 266 and 268, resistors 270 and 272, operational amplifier 274, resistors 276, 278 and 280. This resistor capacitor amplifier network amplifies and level shifts the signals coming from opto-isolator 260 and applies them to detector chip 258. Detector chip 258 has its own 3.58 MHz crystal 282, provides a filtering and selection function with four outputs which indicate receipt of call processing tones on line CPTONE 1, 2, 3 and 4. These outputs are available to microcomputer 100 via pins 32-35 of I/O chip 144. This allows microcomputer 100 to detect the presence of a 100 Hz call waiting tone which is typically sent across the phone line in pairs of two at 4 second intervals. When a call waiting feature is installed on the patient's phone line, detector chip 258, in combination with microcomputer 100, circuitry allows the detection of an incoming telephone call. The base station 10 can then notify the physician's terminal and, on command of the physician's terminal, allow the telephone 12 to ring and allow the patient to access the second incoming call.

Figure 3G:
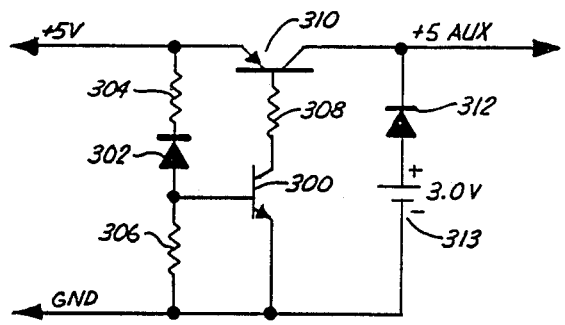
Figure 3G:
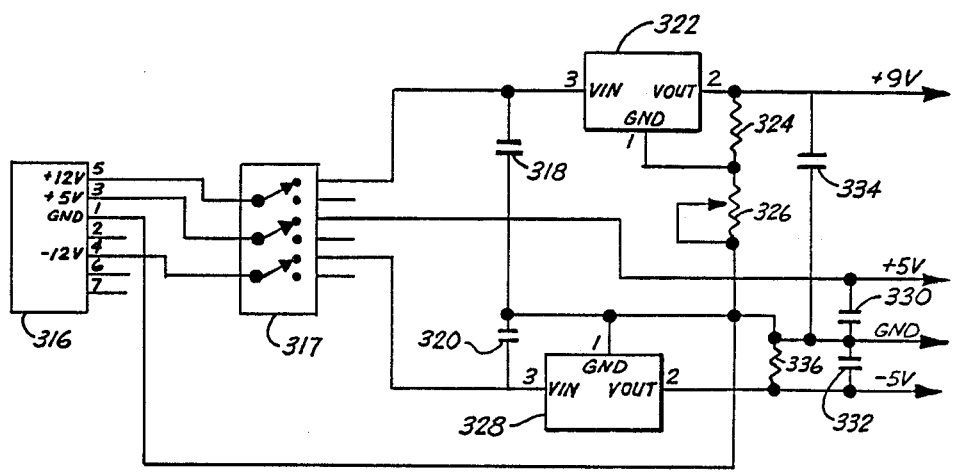

FIG. 3G illustrates the power supply circuitry within base station 10. Transistor 300 in combination with xener diode 302, resistors 304, 306 and 308, transistor 360, diode 312 and battery 314 comprise the auxillary battery power for the real time clock chip 150 and the random access memory chips 158-168. In case of failure of the external power supply or if the unit is not plugged in, this network provides 2.7 volt battery voltage which preserves the data in the random access memory chips 158-168 and keeps the real time clock chip 150 operating.

In FIG. 3GG, connector 316 is the main power connector for the base station 10 and provides power to the main circuit board from an external power supply (not illustrated) which provide voltage of +12, +5 and −12 V. Capacitors 318 and 320 are incoming filter bypass capacitors. Voltage regulator 322 is an adjustable regulator which via resistors 324 and 326 is set to provide the +9 volt power for the RF receiver circuitry (FIG. 3I). Voltage regulator 328 is a fixed regulator which provides a ±5 V power supply for the digital circuitry. Capacitors 330, 332 and 334 are output bypass capacitors for the voltage regulators 322 and 328.

Figure 3H:
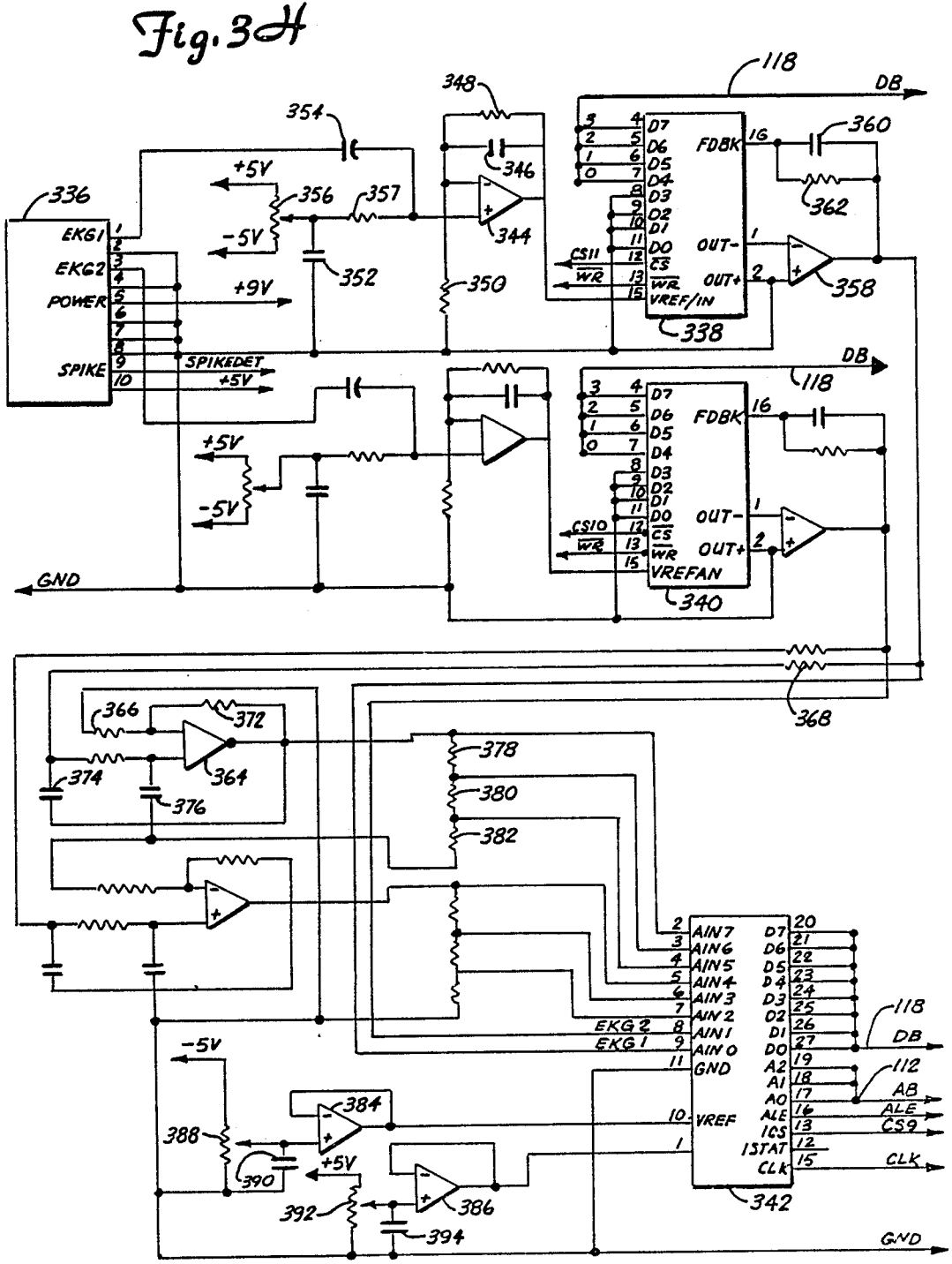
Figure 3J:
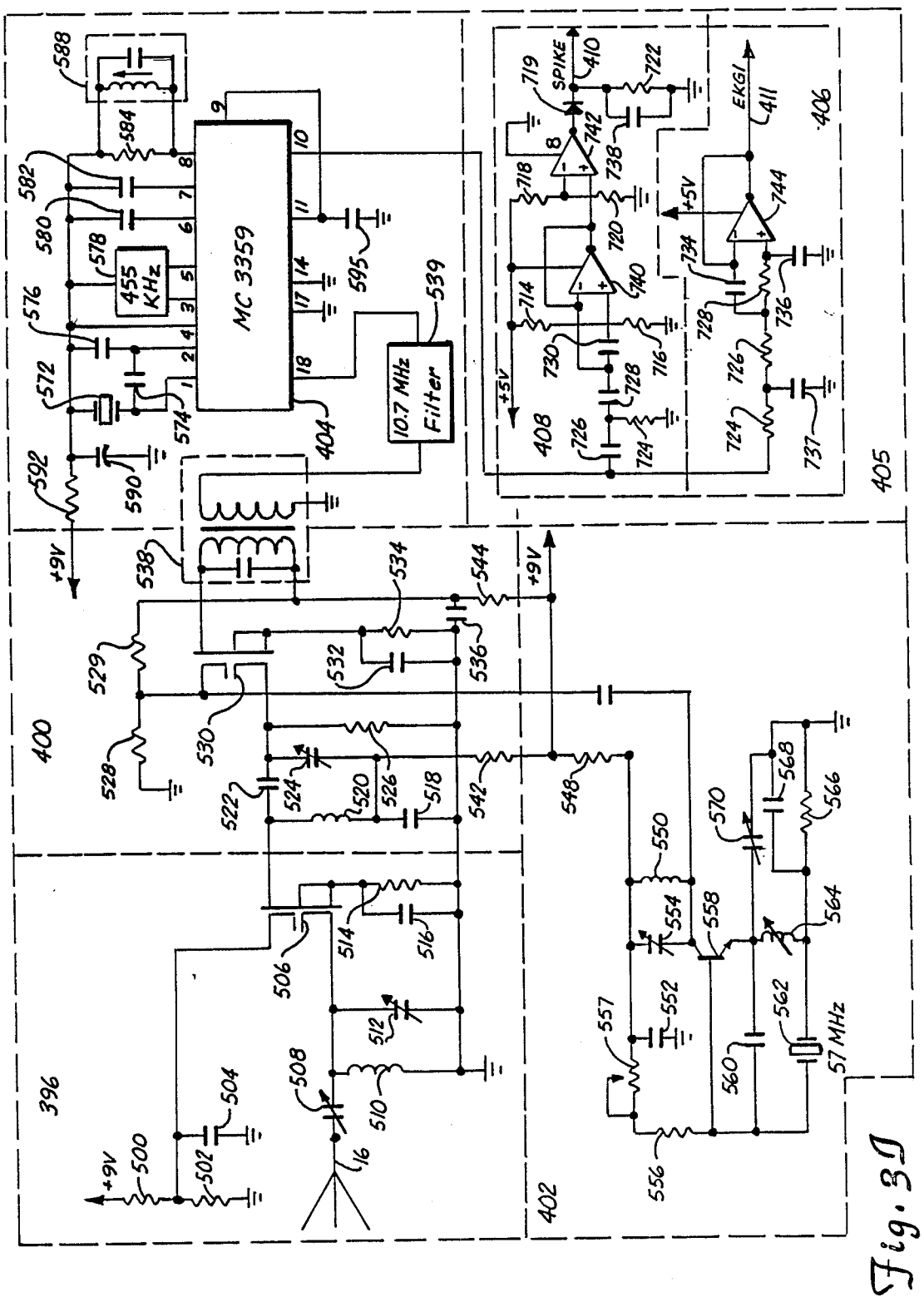
FIG. 3J is a schematic drawing of the circuitry within the patient transmitter.
Figure 37:
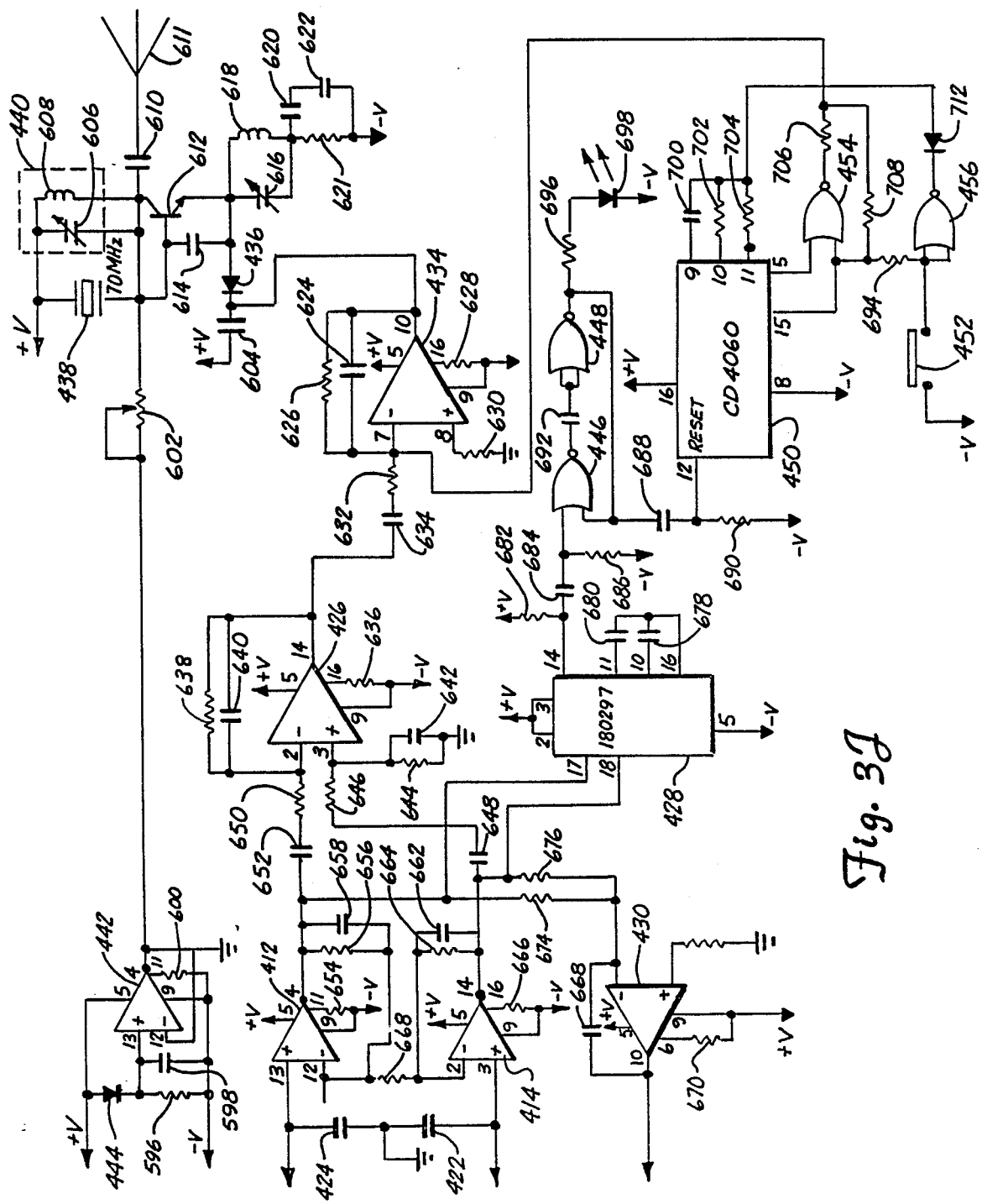

FIG. 3H illustrates the analog ECG processing circuitry of the base station 10. Connector 336 connects the main circuitry to the RF receiver circuitry (FIG. 3I) which provides EKG and patient indicator signals to the main circuit. Connector 336 also provides the +9, +5 volt and ground power to the RF circuitry.

The ECG processing circuitry is configured as two independent analog ECG channels with independent digitally programmable gain controls 338, 340 and an 8 channel A/D converter chip 342. Each channel provides both filtered and unfiltered ECG signals to microcomputer 100 and thus four complete channels are capable of being processed by microcomputer 100.

The demodulated analog EKG signal enters through amplifier 344, capacitor 346, resistor 348, resistor 350, and capacitor 352. Capacitor 354 provides AC coupling and level shifting for the incoming signal. The incoming signal is typically a one volt peak to peak analog ECG level shifted at a positive 2½ volts. Resistor 356 provides a set level shift to allow the output of amplifier 344 to be referenced back to the 0 volt ground reference of the system. Chip 338 is a digital to analog converter chip configured as a digital gain control. Sixteen gain steps are provided. Gain control chip 338 connects directly to the Data Bus 18. Amplifier 358 is the output amplifier of the digital gain control section. Capacitor 360 and resistor 362 provide feedback and filtering. The output of amplifier 358 is fed directly into the EKG 1 input (pin 9) of the A/D converter chip 342, and fed simultaneously into a filter section which provides a 5 Hz to 50 Hz filtered version of the signal through the network comprising amplifier 364, resistors 366, 368, 370, 372 and capacitors 374 and 376. The filtered ECG signal is provided to pin 2 of A/D converter chip 342. The resistor network, comprising resistors 378, 380 and 382, provides various voltage taps into the unused A/D converter channels and allows sampling of the ECG at various amplitude levels. The alternate path from the pin 3 of connector 336 to pins 8 and 5 of A/D converter chip 342 is identical in function to the upper section described earlier. Amplifiers 384 and 386 provide the voltage references for the A/D converter chip 342. Voltages of +5 and −2½ volts are provided. The −2½ volts is provided via resistor 388. Capacitor 390 is used to bypass the input voltage to amplifier 384. Amplifier 384 is used as a unity gain noninverter buffer. Amplifier 386 is also a noninverting buffer and the +5 V reference voltage is provided via resistor 392 bypassed by capacitor 394.

FIG. 3I illustrates the RF receiver section of base station 10. This receiver is a dual superhetradyne 217 MHz RF receiver which takes in the frequency modulated signal from the patient transmitter unit 22 and provides the analog ECG output to connector 336 (FIG. 3H). The circuit employs a telescoping RF antenna 16 followed by an amplifier 396 and filter section 398 and a mixer 400 from its own internal first oscillator 402. Because the circuitry herein is conventional, no detailed description of its operation is believed necessary. Local oscillator 402 provides a 57 MHz signal. The signal is fed to the FM demodulator 404 which has its own 10.245 MHz fundamental crystal source 572 and a 455 KHz local oscillator. In conjunction with its external components, demodulator 404 demodulates the FM signal and produces a data out signal which contains the analog ECG signal with 2 KHz patient alert signals and pacer spike signals superimposed. The data out signal is fed to a filter section 405 including low pass filter 406. Schmitt trigger 408 produces a TTL compatible signal on output 410. Low pass filter 406 separates the ECG signal (0–200 Hz) from the 2 KHz spike/patient alert signals. ECG signals on line 411 are provided to pin 1 of connector 336 and the spike/patient alert signals are provided to pin 9 of connector 336.

FIG. 3K illustrates the circuitry of the transmitter 22 which the patient wears. Operational amplifiers 412, 414 are used as a dual differential amplifier which amplifies a signal from the two patient electrodes 418 and 420. The electrodes are bypassed to ground by capacitors 422 and 424. Amplifiers 412, 414 are used as unity gain buffers which are then fed into amplifier 426 which provides an overall gain of 20. The amplified EKG signal from each electrode is fed in parallel to a Medtronic 180297 Teletrace TM chip 428 manufactured by Micro-Rel, Inc., Tempe, Ariz., which is used in this application simply as an EKG spike detector. The circuitry andoperation of this chip are similar to that described in U.S. Pat. No. 4,226,245, issued to Bennet, and incorporated herein by reference in its entirety. Chip 428 has internal circuitry which provides amplification and edge sense triggering and provides an output at pin 14 when a pacemaker spike is present on the skin. Amplifier 430 provides the drive current to the reference electrode 432 of the unit which is the algebraic sum of the signals created on two electrodes 418 and 420 and is used to drive the patient's skin to a common reference voltage to increase common mode rejection. The amplified ECG out of amplifier 426 is fed to an additional amplifier 434. This unit level shifts the ECG signal and drives the RF oscillator circuit via diode 436. The transmitter circuit uses a 70 MHz crystal 438 in conjunction with a tank oscillator 440 and provides frequency modulated signals centered about 216 MHz. Amplifier 442 provides a reference voltage for the system. A 560 microamp constant current diode 444 is used via the feedback loop of amplifier 442 and provides a regulated bias supply for the FM transmitter section. This circuit provides constant transmitter modulation and output regardless of the internal battery voltage.

The output of the pacing spike detector chip 428 is fed through NOR gates 446 and 448 which are configured as a one-shot and provide a 10 msec. squarewave signal. This 10 msec. squarewave is fed into the EKG path via counter 450. If a pacing spike occurs, counter 450 is started and a 10 msec. burst of 3 KHz is sent to the FM modulator. When the patient alert button 452 is pushed, a minimum 60 msec. burst of 3 KHz is provided to the FM modulator. The two signal sources are interlocked by NOR gates 454 and 456 such that a pacing spike via NOR gates 446 and 448 shuts off automatically at 10 msec. The patient alert button 452 uses a separate output path and oscillates for the 60 msec. period of time, providing absolute differentiation between pacer spike outputs and patient alert button pushes.

| COMPONENT LIST | |
| --- | --- |
| Integrated Circuits | Type |
| 100 | 80C85 Microprocessor |
| 104,106,140,142 | 74HC14 Inverters |
| 120,136,138 | 74HC132 Hysteresis NAND Gate |

-continued

| COMPONENT LIST | |
|---|---|
| 126,128,130,228 | 74HC08 AND Gates |
| 110 | 74HCT573 Octal Bus Driver |
| 114 | 74HCT541 Octal Bus Driver |
| 116,202 | 74HC245 Octal Buffer |
| 122,124 | 74HC138 Decoder |
| 144 | 81C55 I/O RAM Timer |
| 146 | 82C53 Timer |
| 148 | 27C256 ROM |
| 158,160,162,164,166,168 | TC5565 RAM |
| 150 | MM58167 Clock |
| 200 | XE1203 Modem |
| 258 | M981 Detector |
| 234,236,238,446,448,454,456 | 74HC02 NOR Gate |
| 274,344,358,364,384,386 | CA3240 Amplifier |
| 250,260 | LDA200 Opto-Isolator |
| 338,340 | AD7524 D/A Converter |
| 328 | LM320 Regulator |
| 322 | LM317 Regulator |
| 342 | AD7581 A/D Converter |
| 412,414,426,430,434,442 | 8023 Amplifier |
| 740,742,744 | 7631 Amplifier |
| 450 | CD4060 Counter |
| 404 | MC3359 Demodulator |

| Transistors | Type |
|---|---|
| 174,188,220,235,300 | 2N2222 |
| 224,310 | 2N2907 |
| 240,242 | 4N15 |
| 506 | 3N211 |
| 530 | 3N212 |
| 558 | 2N918 |
| 612 | 2N2857 |

| Diodes | Type |
|---|---|
| 107,233,253,312,712 | 1N4148 |
| 444 | 1N5291 |
| 436 | 1N832 |
| 302 | LM103 - Zener |
| 719 | 1N914 |

| Capacitors | Value |
|---|---|
| 108,334 | 22 uF |
| 154,156 | 200 pF |
| 226,268,604,726,728,730,734 | .001 uF |
| 265 | 1 uF |
| 354 | 22 uF |
| 346,352,390,394,318,320,580, 582,738 | .1 uF |
| 360 | .015 uF |
| 374,376,332 | .33 uF |
| 330,590 | 47 uF |
| 504,518,532,536,552,568,620, 622,684 | .01 uF |
| 508 | 1.8–6 uF Adjustable |
| 512,554 | 2.8–12 uF Adjustable |
| 516 | .01 uF |
| 522 | 33 pF |
| 524,554 | 2.8–12 pF Adjustable |
| 546 | 5 pF |
| 560,614,736 | 68 pF |
| 570 | 9–50 pF Adjustable |
| 574 | 150 uF |
| 576 | 68 uF |
| 586,688,700,678,595 | 150 pF |
| 598,680,692 | .1 uF |
| 592 | 10 mF |
| 606 | 3–12 pF Adjustable |
| 610 | 5 pF |
| 616 | 4–40 pF Adjustable |
| 624 | 100 pF |
| 634,652,648 | .47 uF |
| 640,642 | .0033 uF |
| 658,662,688 | 150 pF |
| 424,422,732 | 470 pF |
| 668 | .68 uF |

| Inductors | Value |
|---|---|
| 206,210 | 10 uH |
| 520 | .024 uH |
| 550 | .1 uH |
| 564,618 | .47 uH |

-continued

| COMPONENT LIST | |
|---|---|
| 608 | .047 uH |
| 510 | .035 uH |

| Transformers | Type |
|---|---|
| 538 | 10 MHz IF (Green) |
| 588 | 455 KHz IF (Yellow) |

| Resistors | Value (ohms) |
|---|---|
| 109 | 15K |
| 132,134,176,178,182,192 | 10K |
| 180,190 | 270 |
| 145,147,149,155,230,226 | 10K |
| 247,222 | 2K |
| 248,244,237,252,368,370,556 | 10K |
| 246,514 | 120 |
| 284,264,262,263 | 5K |
| 276,270,272 | 499K |
| 278 | 57.5K |
| 280 | 49.5K |
| 203,204 | 22 |
| 356,388,392 | 20K Adjustable |
| 357 | 180K |
| 350 | 7.5K |
| 348 | 15K |
| 362 | 110K |
| 366 | 39.2K |
| 372 | 22K |
| 378,380,382 | 300 |
| 308 | 10K |
| 304 | 1K |
| 306,336 | 4.7K |
| 326 | 1K Adjustable |
| 324 | 120 |
| 500,502,526,528,584 | 100K |
| 534,542,544,548,592 | 100 |
| 566 | 470 |
| 596 | 5.1K |
| 602,557 | 200K Adjustable |
| 626,638,644 | 470K |
| 628,636,656,666,670,654 | 8.2 M |
| 630 | 62K |
| 623,646,650 | 91K |
| 656,664,720,722 | 100K |
| 676,674 | 110K |
| 660,694 | 10K |
| 672 | 56K |
| 682,686 | 75K |
| 690,724 | 47K |
| 702 | 20K |
| 704 | 270K |
| 706,724,726,728 | 2.2 M |
| 708 | 4.3 M |
| 714 | 1.8 M |
| 716 | 1.5 M |
| 718 | 82K |

DETAILED FUNCTIONAL DESCRIPTION

The operation of the telemetry base station can most conveniently be described in terms of a finite state machine. FIG. 4 illustrates the various functional states of the machine, and summarizes the conditions for changing from one state to another. Understanding of the functioning of base station 10 may be facilitated by referring to FIG. 4 in conjunction with the following detailed description of the states and transitions between states of the base station. The function of the base station in each state, as well as the conditions for changing states and the operations involved in changing states are all controlled by the program stored in the read only memory 146 (FIG. 3A). The source code for the program stored in read only memory 146 is set forth below. The program as set forth is written in Pascal and in assembly language. Compilaton and assembly of the program for loading into read only memory 146 is accomplished via a Hewlett-Packard 64000 Microcomputer Development System.

STATE X

State X, as illustrated in FIG. 4, is the initialization state. During the initialization procedure, all interrupts to microcomputer 100 are disabled. The I/O chip 144 is then started up, and the output states of gates PC0, PC1 and PC2, at pins 37-39, are set to control the operation of timer chip 146. Timer chip 146 is then set to provide a 300 Hz (3.3 msec.) signal on line INT 75 which functions as the basic sampling frequency signal and is provided as an interrupt to the microcomputer 100. In addition, timer chip 146 is programmed to provide a 20 Hz signal on the 20 HERTZ line from pin 17. This 20 Hz signal is used for a variety of functions including as a clock input to pin 9 of chip 146. Subsequently, the input latch (pin 7) to microcomputer 100 from interrupt line INT 7.5 is reset, and the interrupt function of this latch is masked. All other interrupts are enabled. Following this, timer chip 146 is set to provide a one second time out signal on line INT-55 (pin 10). This one second interval is used to time all intervals measured in multiples of one second. Following set-up of the timing intervals, the variables RING NURSE, PT CALLING, and PT GAVEUP are all set false. The amplifier gain is adjusted to an initial setting by gain control 338, the Call Nurse light is turned on, and NEXT STATE is set to A.

TRANSITION TO STATE A

Upon determining that the NEXT STATE=A, and that STATE, indicative of the present state of the machine, is not equal to A, the transition to state A begins. This transition begins by turning on Active light 172, and turning off the Call Nurse light 186. In addition, the one second timer is set to time a period of one second. After this one second interval, reset of the modem chip 200 begins.

Reset of the modem chip 200 includes hanging up the internal phone hook within the modem 200, and subsequently setting the modem to operate in an asynchronous data transfer mode, with parity disabled. In this mode, the modem provides 10-bit asynchronous signals consisting of a first start bit, eight data bits, and a final stop bit. The 8-bit data words may signify an amplitude, if the modem 200 is transmitting digitized EKG signals, or may be a command or indicator code. Finally, the modem 200 is enabled to receive and transmit data by entering appropriate commands through pins 27-34. Following the reset of the modem 200, the Call Nurse light 186 is turned on, and the Active light 172 is turned off.

Next, the telephone 12 coupled to the base station via phone jack 214 is coupled directly to the telephone line jack 204 by means of relay 218. Subsequently, the one second interrupt via line INT 5.5 to pin 9 of microcomputer 100 is masked. The PSEUDORINGER, RING THE BELL, and RING RELAY lines from I/O chip 144 are then all set low, disabling the ringing and pseudo ringing functions. The RING STATE, MODEMCONNECTFAIL, MODEMCONNECTED, and SPIKEENABLED variables are all set false. The Call Nurse light 186 and Active light 172 are then turned off and STATE is set to equal NEXT STATE. The base station 10 has now entered state A.

STATE A

In state A, the base station 10 merely waits and checks to see whether the variable ELITEOFFHOOK is true, indicating that the external telephone 12 has gone off hook. If the external telephone 12 goes off hook, the NEXT STATE is set to "0", which begins the transition to state O. Telephone 12 is coupled directly to the phone line and functions normally.

TRANSITION TO STATE O

During the transition to state O, a time period of twenty seconds is initiated, and interrupt port RST 5.5 (pin 9) of the microcomputer 100 is unmasked to allow counting of the one second interrupts from timer chip 146. The STATE is set to equal NEXT STATE variable, and the device enters state O.

STATE O

During state O, the twenty-second timer functions by decrementing SECONDS LEFT by one with each one second interrupt from timer chip 146 on line INT 55. During state O, the variables ELITEONHOOK which is true when the telephone 12 is on hook, CALLNURSEPRESS, which is true when the Call Nurse button 184 is pressed, as well as SECONDSLEFT are all monitored. If telephone 12 goes on hook prior to either the Call Nurse button 184 being pressed or the time-out of the twenty second interval, NEXT STATE is set to "A", and the transition to A, as described above, begins again. If either the Call Nurse button 184 is pressed or the twenty second interval times out (SECONDSLEFT=0) prior to the telephone 12 going on hook, the NEXT STATE is set to "C", and the transition to state C begins.

TRANSITION TO STATE C

During the transition to state C, the 3.3 msec. interrupt port, RST 7.5 (pin 7), of microcomputer 100 is masked. Subsequently, the command register of modem 200 is reloaded to enable the receiver and transmitter therein. Modem 200 is then placed on hold and data buffer 202 is cleared. Modem 200 is then set to receive and placed in DTMF receive mode so that it will recognize DTMF codes as data. The variable WRITEENABLED is set false, and STATE is set to equal NEXT STATE. The base station now enters state C.

STATE C

During state C, ELITEONHOOK is monitored. If this variable goes true, indicating that the external telephone 12 has gone on hook, NEXT STATE is set to equal "A". Otherwise, the Call Nurse light 186 goes on, and base station 10 waits for receipt of data from modem 200 indicating the receipt of a DTMF A tone by modem 200. The base station then continues to wait for the receipt of a DTMF B tone from the physician's monitoring station. If the DTMF A and B tones are received in their proper order, NEXT STATE is set to "D". Base station 10 will continue to wait for receipt of the properly ordered A and B tones until the external phone 12 goes on hook. As discussed above, if the external phone 12 goes on hook, NEXT STATE is set to "A", and the transition to state A, discussed above, is once again initiated.

TRANSITION TO STATE D

During the transition to state D, modem 200 attempts to establish communication with an identical modem in the physician's monitoring station. The Call Nurse light 186 is turned off, and the data link attempt is begun. The bell ringing circuitry is disabled and the external phone 12 is disconnected from the jack 204 by relay 218. The data register of modem 200 is then loaded with the character "A", which allows the modem to transmit modem answer tone. If modem 200 receives a proper modem response carrier frequency from the physician's monitoring station, the modem 200 assembles a "—" in its data register. The data register of modem 200 is read, and if it contains a "—", the microcomputer 100 enables modem 200 for two-way transmission by writing appropriate command bits in to its data register. If the connect attempt was successful, MODEMCONNECTED is set true. If not, then MODEMCONNECTFAIL is set true. The data queue for the 8-bit EKG data from A/D converter 342 is reinitialized, and RST 75 interrupt (pin 7) of microcomputer 100 is unmasked to allow for sampling of data from A/D converter 342. STATE is set equal to NEXT STATE, and the base station enters state D.

STATE D

In state D, the base station checks to see whether the previously attempted modem connection to the doctor's monitoring station was successful. If this connection was successful, as indicated by MODEMCONNECTED being true, then NEXT STATE is set to equal "E". If MODEMCONNECTFAIL is true, then NEXT STATE is set to equal "J". Transition to state E or J then begins.

TRANSITION TO STATE E

In the transition to state E, the Active light 172 is turned on. The ringing relay 216 is disabled, and the queue of data for transmission is again reinitialized. STATE is then set equal to NEXT STATE and the base station enters state E. The transition to state E may also be made from state H, discussed below. If so, PTGAVEUP is set true.

STATE E

In state E, the base station transmits digitized values of the ECG signal. The digital value of the ECG signal, as stored in the data register of A/D converter 342, is read each 3.3 msec. in response to the interrupt on line INT 75 from pin 15 of chip 146. With each interrupt on line INT 75, the data present in the output register of the A/D converter 342 is read. Because modem 200 transmits at a maximum rate of 1200 baud, and because the data words transmitted by modem 200 are 10-bits long, modem 200 is not able to transmit each 8-bit byte assembled by the A/D converter 342. For this reason, the interrupt driven SAMPLER subroutine performs an averaging function. Each 10 msec., the sampler routine provides a byte to the modem 200 for transmission. This byte represents the running average of the sampled bytes obtained from the A/D converter 342. In addition, if the spike detection function has been enabled with each 3.3 msec. interrupt, SAMPLER checks to determine whether SPIKE is true. If SPIKE is true, this is indicative of the fact that the SPIKEDETECT line coupled to the radio receiver by pin 9 of connector 336 has gone high. In this case, the SAMPLER routine provides spike indicator code to modem 200 for transmission.

Sampled data presented to the modem for transmission takes several forms. Byte values of 001 hexadecimal (001H) to 0FDH are reserved for indicating EKG amplitude. If the value of the averaged bytes from A/D converter 342 is equal to 0FFH or 0FEH, then the value is modified to 0FDH. If the averaged value is 00H, then it is modified to 001H. This acts as a software filter of extreme EKG values, and allows the use of bytes having values of 00H, 0FFH, and 0FEH as indicators. If SPIKE is true during any one of the three readings of data from A/D converter 342 between modem transmissions, the SAMPLER subroutine will set the data sent by modem 200 to 0FFH. This allows the physician's base station to detect the occurrence of a pacing spike. Similarly, because the pressing of the push button on the patient's transmitter also activates the spike detection circuitry within the receiver, but for a longer time period (60 msec.), it allows the physician's monitoring station to determine that the patient has pressed the alert button 36 on the patient transmitter 22, because sequential 0FFH bytes will be decoded by the physician's monitoring station.

During state E, the base station's own EKG monitoring and analysis software is functional. This software is similar to and derived from the software used to control the operation of the portable EKG acquisition unit described in U.S. Pat. No. 4,360,030, incorporated herein be reference in its entirety. The EKG analysis and processing software in the present application differs in that it has been converted from Intel and NSC 800 assembler format to HP64000 8085 assembler format, the code has been modified to use the base station's I/O capabilities, and some variable names have been changed and features deleted.

The EKG processing and analysis may conveniently be divided into real time and nonreal time functions. Sampling of data from the A/D converter 342 is under the control of the 3.3 msec. interrupt driven SAMPLER subroutine. The SAMPLER subroutine reads the 8-bit data register of A/D converter 342 each 3.3 msec., accumulates five sequential values and maintains a running average of those values. Each 10 msec., the SAMPLER subroutine calls the INBYTE subroutine which determines what information byte will be loaded into the modem for transmission. The SAMPLER subroutine will present either the averaged EKG value or the spike detect code 0FFH. The SAMPLER subroutine is enabled during initiation of the data queue during the transition to state D. Each 10 msec., the INBYTE subroutine determines which of a variety of available information bytes will be transmitted by the modem 200. These data types include command bytes, calibration bytes, and EKG/spike bytes. The INBYTE subroutine prioritizes data transmission in this order. Whenever called, the INBYTE subroutine first checks to see whether a command byte is avaliable for transmission, then checks to see whether the calibration generation routine (discussed below) is functioning and, in default, loads and transmits the EKG/spike detect information from the SAMPLER subroutine.

During state E, a number of variables are monitored to determine whether commands, rather than EKG data are to be sent by modem 200 to the physician's monitoring station. If the PTCALLING variable is true, the command 002H will be loaded into the modem for transmission. If the RING NURSE variable is true, then the command 001H will be loaded into the modem for transmission. If the variable PTGAVEUP is true, 006H will be loaded into the modem for transmission. Transmission of such command bytes is always preceded by a 0FEH byte, which indicates to the physician's monitoring station that the following byte is a command byte. As such, each command is a two byte transmission.

PTCALLING indicates that the patient has lifted the receiver of the external telephone 12 in order to contact the physician. RING NURSE goes true when the patient presses Call Nurse button 184. If both of these codes are transmitted, the physician's monitoring station is informed that the patient desires to use the intercom function of the base station, as described in the description of state F, below. The PTGAVEUP variable goes true when the patient hangs up the external telephone 12. The significance of these transmissions is discussed below.

PTALERT indicates that the base station 10 has decoded the occurrence of a string of sequential spike detects. During sampling of the incoming signal by the SAMPLER subroutine, a running count is kept of the number of times that SPIKE has been true during the previous 10 3.3 msec. interrupts. If SPIKE has been true for five of the previous ten 3.3 msec. interrupt cycles, PTALERT is set true. In this case, the INBYTE subroutine will select the command 001H (same as RING NURSE) for transmission. This feature allows the patient to inform the physician's monitoring station of a problem, without being in the immediate vicinity of the base station 10.

CALGENCOUNT indicates the status of calibration signal generation. If calibration signal generation is underway, indicated by CALGENCOUNT not equal 0, then the INBYTE subroutine will transmit an appropriate calibration signal value. The calibration signal generation activity is triggered by the receipt of a command by the modem 200, and is discussed below.

SEND RATE indicates that the modem 200 has previously received a command to transmit the patient's heart rate. If SEND RATE is true, the modem initiates a command transmission consisting of a first 0FEH byte and a subsequent byte, RATE TO SEND, between 40H and 255H, indicating the patient's heart rate. RATE TO SEND is generated by the nonreal time portion of the EKG signal processing. Although this function is described in more detail in the above-referenced Citron et al patent, the basic functions can be summarized as follows. During real time sampling of the EKG signal bytes from A/D converter 342, the amplitude and slope of the EKG signal are monitored. In the event that a particular string of EKG bytes are likely candidates to be QRS complexes, indicative of hearbeat, such data is loaded into RAM, for analysis by the RSENSE subroutine. This subroutine determines whether the QRS candidates are, in fact, QRS complexes. The time differential between detected QRS complexes is stored. After four QRS intervals have been detected and validated, an average interval is calculated, which is translated into an average heartbeat rate. This is the RATE TO SEND byte. If this byte is available and the modem 200 has received a request for rate information from the physician's monitoring station, the 0FEH byte, followed by the RATE TO SEND byte will be transmitted by the modem 200.

In addition to transmitting data commands during state E, the base station monitors the modem 200 for incoming commands from the physician's base station. Modem 200 is a full duplex modem, so receipt of incoming commands delays transmissions out for a few milliseconds, but does not prevent their transmission. If the modem 200 has received a command and that command is available and assembled in the data register of the modem 200, the base station will then read the command to determine whether it is one of a number of predetermined command bytes.

If the GAINUP command 00AH is received, microcomputer 100 performs a subroutine which increases the gain of the EKG signal as applied to the A/D converter 342. This function is controlled by chip 338 which functions as a digital gain control for the analog EKG signal. Similarly, if the GAINDWN command 00BH is received, microcomputer 100 decrements the gain of the EKG signal. This allows the physician's monitoring station to adjust the gain of the telemetry system in order to optimize the EKG signal. If the command 005H is received, the spike detect function of microcomputer 100 via pin 5 is enabled, if the command 06 is received, the spike detect function is disabled.

An additional command which may be received by modem 200 is the GO TO INTERCOM command 002H which, in conjunction with a determination of whether telephone 12 is on hook, initiates a change to either state G or state F. If GO TO INTERCOM is received and the telephone 12 is on hook, then NEXT STATE is set to "G". But if the telephone 12 is off hook, then NEXT STATE is set to "F".

If the command 0FEH is received, the calibration signal generation routine is begun. This routine is driven by the INBYTE subroutine which transmits, sequentially, two bytes indicating the precalibration value (PRECALVAL), ten bytes at a value equal to the precalibration value multiplied by the amplifier gain setting provided to the digital gain control 338 (STEPCALVAL) and two bytes indicating the post-calibration value (POSTCALVAL), which is equal to the precalibration value. This allows the physician's monitoring station to calibrate its own EKG analysis circuitry. As discussed above, transmission of the PRECALVAL, STEPCALVAL, and POSTCALVAL bytes takes precedence over EKG and spike detect transmission, but will be interrupted by command transmissions to the physician's monitoring station. If the command 007H is received by the modem, then SEND RATE is set true, triggering transmission of the RATE TO SEND byte, if available.

If a command is indicated as having been received by the modem 200, but is not a valid byte or cannot be read, the command received is set to 00H, clearing the register and allowing transmission of data out. At any time during state E, if the patient lifts the receiver of the telephone 12 off hook and presses Call Nurse button 184, then NEXT STATE is set to "H", triggering the transition to state H.

TRANSITION TO STATE H

Transition to state H begins with turning Call Nurse light 186 on, and setting PTCALLING true. This triggers a transmission of the PTCALLING code to the physician's monitoring station, via modem 200 as described above in conjunction with state E. Because the transmission of data from the modem to the physician's station is interrupt driven, it continues during the transition to state H. The base station then enters a ring back procedure which involves setting RING STATE true and setting RING NURSE true. As discussed above, setting RING NURSE true will initiate a transmission of the code corresponding to RING NURSE to the physician's monitoring station. In addition, the relay 218 is set to couple telephone 12 to jack 204, in parallel with the modem 200. The psuedo ringing circuit is energized to allow the ringing relay 216 to generate a simulated telephone ring, which the patient will hear through the earphone of the telephone 12. This simulated ringing, however, does not interfere with the continued transmission by modem 200 of EKG and other data to the physician's monitoring station. At the same time, it simulates normal telephone function, and indicates to the patient that he has contacted the doctor's monitoring station. After the pseudo ringing procedure is initiated, STATE is set to equal NEXT STATE, and the base station enters state H.

STATE H

In state H, microcomputer 100 waits for the nurse or physician at the physician's monitoring station to pick up the phone in order to initiate voice contact. During state H, the simulated ring is allowed to stay on for one second, and is then turned off for three seconds by setting the PSEUDORINGER line high and low, sequentially. This procedure continues until and unless the modem 200 receives the GO TO INTERCOM command 002H. In this case, NEXT STATE is set to "F". If the patient simply hangs up the phone, NEXT STATE is set to "E" and the base station enters the transition to state E, as described above. As noted in the discussion of the transition to state E, the fact that the previous state was H will set PTGAVEUP true, triggering transmission of the command byte 006H. This will alert the physician's monitoring station that the patient no longer desires voice contact. While the base station is in state H, during the psuedo ringing procedure, the RING NURSE variable is alternately set true and false, initiating spaced transmissions of the RING NURSE code to the physician's monitoring station. The overall result of this is that the RING NURSE code is sent to the physician's monitoring station once every six seconds signaling the patient's desire for voice communication.

TRANSITION TO STATE F

Transition to state F begins with the turn off of the Call Nurse light 186 and the Active light 172. The bell ringing functions are disabled, and the procedure of entering the intercom state is begun by masking of the 3.3 msec. interrupts to microcomputer 100, via pin 7. Because the 3.3 msec. interrupts are necessary in order to transmit digital data via the modem, this disables the modem from transmitting although it remains connected to jack 204. Modem 200 is on hold temporarily while the data buffer 202 associated with modem 200 is cleaned out. Modem 200 is then enabled to receive and switched to DTMF mode to enable recognition of DTMF tones as data. The external phone 12 is then coupled to the phone lines via relay 218. STATE is set equal to NEXT STATE, and the base station enters state F. It is important to note that until and unless the intercom function is achieved, data transmission continues.

STATE F

In state F, the telephone 12 is connected to the phone line, allowing the telephone 12 to function as an intercom between the patient and the physician. During state F, the base station 10 behaves as during state C, and looks for a DTMF A tone followed by a DTMF B tone. Although modem 200 is disabled from transmission, it is still capable of receiving and decoding the DTMF tones. In the event that a DTMF A followed by a DTMF B is received, NEXT STATE is set to I, and the transition to state I is initiated.

TRANSITION TO STATE I

During the transition to state I, an attempt is made to link modem 200 to the modem in the physician's monitoring station, precisely as discussed above in conjunction with the transition to state D. After the attempt to link has been made, STATE is set to equal NEXT STATE, and the base station enters state I.

STATE I

State I is virtually identical to state D, discussed above. In state I, the base station checks to see whether the attempted connection to the modem at the physician's base station was successful. If the connection was successful, then NEXT STATE is set to equal "E". If unsuccessful, then NEXT STATE is set to equal J, triggering the transitions to those states. The transition to state E has been discussed above.

TRANSITION TO STATE J

During the transition to state J, the 3.3 msec. interrupt to pin 7 of microcomputer 100 is first masked. Relay 218 is then commanded to disconnect telephone 12 from jack 204. The modem 200 is then reset, as described above in conjunction with the transition to state A, and is enabled to transmit and receive. The Active light 172 and the Call Nurse light are turned off, and the bell ringing functions are disabled. MODEMCONNECTED and MODEMCONNECTFAIL are both set false, the Active light 172 is turned on, and AUTOATOG is set true. A one second time interval is begun, and STATE is set equal to NEXT STATE. The base station 10 now enters state J.

STATE J

In state J, the base station 10 waits for a reconnect attempt via a new phone call from the physician's base station. During state J, the modem 200 is monitored to determine whether ring signals are present on the phone line. If so, NEXT STATE is set to "K". Otherwise, the Active light 172 is flashed on and off at one second intervals, while waiting for ring signals.

TRANSITION TO STATE K

During the transition to state K, the Active light 172 and the Call Nurse light 186 are first turned off. A data link connection between modem 200 and the modem at the physician's base station is then attempted. This data link attempt corresponds to the data linking attempt described in conjunction with state D, above, and includes disabling of the ring back and bell generators by setting a RINGTHEBELL line and PSEUDORINGER lines low and the ELITERELAY line high, via I/O chip 144. The modem 200 is then set to have a command written into it, and the modem 200 is commanded to enter the answer mode. The modem 200 transmits a modem answer tone, and waits for a response from the modem in the physician's monitoring station. If a proper modem carrier response is detected, then MODEMCONNECTED is set true. If the response is anything else, then MODEMCONNECT-FAIL is set true. The data queue is then initialized, and STATE is set to equal NEXT STATE. The base station 10 then enters state K.

STATE K

State K corresponds to state D, and simply checks for a successful data link to the modem of the physician's base station. If MODEMCONNECTED is true, then NEXT STATE is set to "E". If MODEMCONNECT-FAIL is set true, then NEXT STATE is set to "J". The transitions to states E and J have been discussed previously.

TRANSITION TO STATE G

As discussed above, in the event that the GO TO INTERCOM command is received during state E, and the telephone 12 is on hook, NEXT STATE was set to "G". During the transition to state G, the Active light 172 and the Call Nurse light 186 are turned off. The procedure for connecting external telephone 12 as an intercom telephone is then begun. First, the 3.3 msec. interrupt to pin 7 of microcomputer 100 is masked. Modem 200 is then placed oh hold and the data buffer 202 is then cleaned out. Modem 200 is then placed in DTMF mode to enable recognition to DTMF tones as data and then is enabled for transmission and receiving. Because the 3.3 msec. interrupt to pin 7 of microcomputer 100 has been masked, no data transmissions from modem 200 to the physician's base station may occur. Relay 218 connects telephone 12 to the phone line. Finally, the relay 216 is activated in order to initiate the ringing of the bell. STATE is set to equal NEXT STATE, and the base station 10 enters state G.

STATE G

During state G, the bell of telephone 12 is rung in order to signal the patient that the physician desires to enter the intercom function (state F). During state G, the bell is sequentially turned on and off for three second time periods, until one of two events occurs. The first event is the expected response that the patient lifts the hook of telephone 12. If this occurs, NEXT STATE is set to "F", and the transition to sate F begins. This transition has been discussed above. Alternatively, if the patient does not respond to the ringing telephone 12, the physician's base station may send a DTMF tone equal to the character "a" or "*". During state g, the modem 200 is monitored to determine whether a data transmission from the physician's base station has been received. If so, the command received is checked to determine whether it is one of the two previously denoted characters. If so, then NEXT STATE is set to L. Otherwise, buffer 202 is cleared, and the base station continues to wait for either a valid command from the physician's base station or for the patient to lift the phone.

TRANSITION TO STATE L

The transition to state L corresonds exactly to the previously described transition to state K and to state D. This transition includes an attempt to establish a data link between modem 200 and the modem in the physician's monitoring station. After the attempt, NEXT STATE is set to "L", and the base station 10 enters state L.

STATE L

State L corresponds to states D and K described above. In state L, the base station 10 checks to determine whether the attempted data link which previously occurred has been successful. If MODEMCONNECTED is true, then NEXT STATE is set to "E". If MODEMCONNECTFAIL is true, then NEXT STATE is set to "J". The transitions to states E and J have been described above.

The software listing describing the function of the base station 10 in more detail follows below.

```
FILE: SH3:BOBBS1        HP 64000 - Pascal     "8085 Code Generator 1  0001  1  "8085"
2  0000  1  $EXTENSIONS ON$
3  0000  1  $SEPARATE ON$
4  0000  1  $OPTIMIZE OFF$
5  0000  1  PROGRAM SM;
6  0000  1
7  0001  1  CONST
8  0000  1      PTCALLINGNURSE = 02H;
9  0000  1      TIME_GOES_BY = TRUE;
10 0000  1
11 0000  1  TYPE
12 0000  1                (0 1 2 3 4 5 6 7 8 9 A B C D E F)
13 0000  1      STATE_TYPE = (A,B,C,D,E,F,G,H,I,J,K,L,M,N,O,X);
14 0000  1      RM_STATE_TYPE = (RESET,WAIT,SETUP,MNTR); (see module MONITOR)
15 0001  1      BITS       = (D0,D1,D2,D3,D4,D5,D6,D7);
16 0000  1  VAR
17 0000  1
18 0000  1      ID    : INTEGER;
19 0002  1      JUNK  : BYTE;
20 0003  1      COUNT : INTEGER;
21 0005  1
```

```
22 0005  1  $GLOBVAR ON$
23 0005  1     STACK_AREA  (64): ARRAY[0..1023] OF BYTE;    (allocates space)
24 0405  1     STACK_       (65): BYTE;                      (init value for compile )
25 0406  1     WORKVAR       : BYTE;
26 0407  1     AUTOATOG      : BOOLEAN;                      (ff for auto answer blink)
27 0408  1     SEND_RATE     : BOOLEAN; (Controls the sending of the rate pair)
28 0409  1  $GLOBVAR OFF$
29 0409  1
30 0409  1  $EXTVAR ON$
31 0409  1     RM_STATE       : RM_STATE_TYPE;               (module MONITOR)
32 0409  1     NEXT_RM_STATE  : RM_STATE_TYPE;               (module MONITOR)
33 0409  1     RATE_TO_SEND   : BYTE;                        (module MONITOR)
34 0409  1     SAMPLE_ON      : BOOLEAN;                     (module MONITOR)
35 0409  1     SPIKE_ENABLED  : BOOLEAN;
36 0409  1     RING_STATE     : BOOLEAN;
37 0409  1     RINGNURSE,
38 0409  1     PTCALLING,
39 0409  1     PTGAVEUP       : BOOLEAN;                     (AUX - Serviced & reset by ISR)
40 0409  1     COMMAND_RCVD   : BYTE;                        (AUX)
41 0409  1     SECONDS_LEFT   : INTEGER;                     (AUX)
42 0409  1     RESULT         : BYTE;
43 0409  1     XECOM_COMMAND  : SET OF BITS;
44 0409  1     XECOM_DATA     : BYTE;
45 0409  1     A8155          : BYTE;
46 0409  1     TIMER_LO       : BYTE;
47 0409  1     TIMER_HI       : BYTE;
48 0409  1     PORT_A         : SET OF BITS;
49 0409  1     PORT_B         : SET OF BITS;
50 0409  1     PORT_C         : SET OF BITS;
51 0409  1     CTC_MODE       : BYTE;
52 0409  1     CTC_0          : BYTE;
53 0409  1     CTC_1          : BYTE;
54 0409  1     CTC_2          : BYTE;
55 0409  1     A_GAIN,
56 0409  1     A_AMP          : BYTE;
57 0409  1     RING_COUNT     : BYTE;        (Number of uninterrupted rings)
58 0409  1     CONNECT_RESULT : CHAR;        (RESULT OF MODEM CONNECT FUNCTION)
59 0409  1     MODEMCONNECTED : BOOLEAN;
60 0409  1     MODEMCONNECTFAIL : BOOLEAN;
61 0409  1     PHYSCONNECTED  : BOOLEAN;
62 0409  1     PHYSCONNECTFAIL : BOOLEAN;
63 0409  1     XE_CMD : SET OF BITS;
64 0409  1     VOICEHOOKFLAG  : BOOLEAN;
65 0409  1
66 0409  1  $EXTVAR OFF$
67 0409  1
68 0409  1  $GLOBVAR ON$
69 0409  1
70 0409  1     I_FLG,D_FLG,T_FLG            : BOOLEAN;
71 040C  1     I_BYTE, D_BYTE               : BYTE;
72 040E  1
73 040E  1     INTRMSK        : SET OF BITS;
74 040F  1     INTRSTS        : SET OF BITS;
75 0410  1
76 0411  1     STATE          : STATE_TYPE;
77 0411  1     NEXT_STATE     : STATE_TYPE;
78 0412  1     MINISTATE      : BYTE;
```

```
 79 0413 1
 80 0413 1     SECOND_1      : INTEGER;      (Used in split time)
 81 0415 1     XECOM_RESULT  : CHAR;
 82 0416 1     GTD_CMD       : SET OF BITS;
 83 0417 1     GTD_DATA      : BYTE;
 84 0418 1
 85 0418 1     KINDEX        : BYTE;
 86 0419 1     OK            : BOOLEAN;
 87 041A 1
 88 041A 1     $PAGE$
 89 0000 1     (Imported procedures/functions)
 90 0000 1     PROCEDURE DISABLE_75;                    EXTERNAL;
 91 0000 1     PROCEDURE ENABLE_75;                     EXTERNAL;
 92 0000 1     PROCEDURE CURRENT_RMS_OPS;               EXTERNAL; (module MONITOR)
 93 0000 1     PROCEDURE CHANGE_RMS;                    EXTERNAL; (module MONITOR)
 94 0000 1     PROCEDURE CLEARDISP;                     EXTERNAL;
 95 0000 1     PROCEDURE DISPSTATE;                     EXTERNAL;
 96 0000 1     FUNCTION CALLNURSEPRESS    : BOOLEAN;    EXTERNAL;
 97 0000 1     FUNCTION CALGEN: BOOLEAN;                EXTERNAL;
 98 0000 1     FUNCTION GOTOINTERCOM      : BOOLEAN;    EXTERNAL;
 99 0000 1     FUNCTION CANCELINTERCOM    : BOOLEAN;    EXTERNAL;
100 0000 1     FUNCTION RELEASEBASE       : BOOLEAN;    EXTERNAL;
101 0000 1     FUNCTION NURSECALLING : BOOLEAN;         EXTERNAL;
102 0000 1     FUNCTION GAINUP : BOOLEAN;               EXTERNAL;
103 0000 1     FUNCTION GAINDWN : BOOLEAN;              EXTERNAL;
104 0000 1     PROCEDURE ISR55;                         EXTERNAL;
105 0000 1     PROCEDURE ENABLE;                        EXTERNAL;
106 0000 1     PROCEDURE DISABLE;                       EXTERNAL;
107 0000 1     PROCEDURE SMASK;                         EXTERNAL;
108 0000 1     PROCEDURE RMASK;                         EXTERNAL;
109 0000 1     PROCEDURE TICK;                          EXTERNAL;
110 0000 1     PROCEDURE SETCLOCK(SECONDS:INTEGER);     EXTERNAL;
111 0000 1     PROCEDURE STOPCLOCK;                     EXTERNAL;
112 0000 1     PROCEDURE SENDBYTEUP(B:BYTE);            EXTERNAL;
113 0000 1     PROCEDURE SENDTOCASPER(A:BYTE);          EXTERNAL;
114 0000 1     PROCEDURE INIT_QUEUE;                    EXTERNAL;
115 0000 1     FUNCTION  GOTODATA         : BOOLEAN;    EXTERNAL;(telephone)
116 0000 1     FUNCTION  BEING_CALLED     : BOOLEAN;    EXTERNAL;
117 0000 1     PROCEDURE SENDFUNC(A:CHAR;VAR B:CHAR);   EXTERNAL;
118 0000 1     FUNCTION  ELITEONHOOK      : BOOLEAN;    EXTERNAL;
119 0000 1     FUNCTION  ELITEOFFHOOK     : BOOLEAN;    EXTERNAL;
120 0000 1     PROCEDURE ELITEONLINE;                   EXTERNAL;
121 0000 1     PROCEDURE ELITEOFFLINE;                  EXTERNAL;
122 0000 1     PROCEDURE XECOM_INIT;                    EXTERNAL;
123 0000 1     PROCEDURE HANGUPLINE;                    EXTERNAL;
124 0000 1     PROCEDURE ENABLE_XECOM;                  EXTERNAL;
125 0000 1     PROCEDURE DISABLE_XECOM;                 EXTERNAL;
126 0000 1     PROCEDURE ENABLE_INOUT;                  EXTERNAL;
127 0000 1     PROCEDURE ENABLE_TXRX;                   EXTERNAL;
128 0000 1     PROCEDURE DISABLE_TXRX;                  EXTERNAL;
129 0000 1     PROCEDURE PHYSCHECK;                     EXTERNAL;
130 0000 1     PROCEDURE STARTBELL;                     EXTERNAL;
131 0000 1     PROCEDURE STOPBELL;                      EXTERNAL;
132 0000 1     PROCEDURE SERVICEBELL;                   EXTERNAL;
133 0000 1     PROCEDURE STARTRINGBACK;                 EXTERNAL;
134 0000 1     PROCEDURE STOPRINGBACK;                  EXTERNAL;
135 0000 1     PROCEDURE SERVICERINGBACK;               EXTERNAL;
```

```
136 0000  1  PROCEDURE MODEMCHECK;                              EXTERNAL;
137 0000  1  PROCEDURE XECOM_TO_DATA;                           EXTERNAL;
138 0000  1  PROCEDURE LOOK_FOR_COMMAND;                        EXTERNAL;
139 0000  1  PROCEDURE XECOM_TO_DTMF;                           EXTERNAL;
140 0000  1  PROCEDURE XECOM_RESET;                             EXTERNAL;     (XET -- hardwar)
141 0000  1  PROCEDURE INTERCOM;                                EXTERNAL;     (XET -- sets ev)
142 0000  1  FUNCTION DATALINK : BYTE;                          EXTERNAL;     (XET -- sets up)
143 0000  1  PROCEDURE XECOM_DO(B:BYTE;C:BOOLEAN);              EXTERNAL;
144 0000  1  PROCEDURE GETDATA(VAR INFO_FLAG: BOOLEAN; (Does it have an information byte fro)
145 0002  2                    VAR DATA_FLAG: BOOLEAN; (Does it have data?)
146 0004  2                    VAR TXRDY_FLG: BOOLEAN; (Does it see TXRDY at time of procedu)
147 0006  2                    VAR INFO_BYTE: BYTE;    (Information byte from XeCOM valid on)
148 0008  2                    VAR DATA_BYTE: BYTE     (Data byte from XeCOM; valid only if )
149 000A  2                   );                               EXTERNAL;
150 0000  1  PROCEDURE ENABLE_EKG;                              EXTERNAL;
151 0000  1  PROCEDURE DISABLE_EKG;                             EXTERNAL;
152 0000  1  PROCEDURE INCREASE_GAIN;                           EXTERNAL;
153 0000  1  PROCEDURE DECREASE_GAIN;                           EXTERNAL;
154 0000  1  PROCEDURE GEN_CALSIG;                              EXTERNAL;
155 0000  1  PROCEDURE ACTIVELITEON;                            EXTERNAL;
156 0000  1  PROCEDURE ACTIVELITEOFF;                           EXTERNAL;
157 0000  1  PROCEDURE CNLITEON;                                EXTERNAL;
158 0000  1  PROCEDURE CNLITEOFF;                               EXTERNAL;
159 0000  1  PROCEDURE BLINKA;                                  EXTERNAL;
160 0000  1  PROCEDURE BLINKB;                                  EXTERNAL;
161 0000  1  PROCEDURE START_UP;                                EXTERNAL;
162 0000  1  PROCEDURE FLUSHBYTE;                               EXTERNAL;
163 0000  1  PROCEDURE VOICE_OFFHOOK;                           EXTERNAL;
164 0000  1  PROCEDURE VOICE_ONHOOK;                            EXTERNAL;
165 0000  1
166 0000  1  $PAGES
167 0000  1    PROCEDURE EVALUATE_TRIGGERS;
168 0000  2      (Here we evaluate the possible triggers to new states)
169 0000  2    BEGIN
170 0000  2      CASE STATE OF
171 0006  2      A: BEGIN
172 0006  2         (7AUG1985 VERSION)
173 0006  2         (This is the POTS onhook state)
174 0006  2         IF ELITEOFFHOOK THEN NEXT_STATE := 0;        (20 seconds with Xecom off!)
175 0011  2         END;
176 0014  2
177 0014  2      C: BEGIN
178 0014  2         (15AUG1985 VERSION)
179 0014  2         (This is the 'Ready for 1st DTMF A' state)
180 0014  2
181 0014  2         IF ELITEONHOOK   THEN NEXT_STATE := A;
182 001F  2
183 001F  2         CNLITEON;
184 0022  2
185 0022  2         WORKVAR := BYTE(XECOM_COMMAND * [D7,D1]);
186 002A  2         CASE WORKVAR OF
187 002D  2            130  : COMMAND_RCVD := XECOM_DATA;
188 0036  2            128  : COMMAND_RCVD := 0;
189 003E  2            2    : BEGIN
190 003E  2                     COMMAND_RCVD := XECOM_DATA;
191 0044  2                     COMMAND_RCVD := 0;
192 0049  2                   END;
```

```
193 004C  2         0        : COMMAND_RCVD := 0;
194 0054  2       END; (CASE)
195 006B  2
196 006B  2       IF (COMMAND_RCVD = 'a') THEN
197 0073  2       (Here we wait for 1 second and then look for a DTMF B)
198 0073  2       BEGIN
199 0073  2         SETCLOCK(1);
200 0078  2         REPEAT UNTIL (SECONDS_LEFT = 0);
201 0084  2         WORKVAR := BYTE(XECOM_COMMAND * [D7,D1]);
202 008C  2         CASE WORKVAR OF
203 008F  2           130    : COMMAND_RCVD := XECOM_DATA;
204 0098  2           128    : COMMAND_RCVD := 0;
205 00A0  2           2      : BEGIN
206 00A0  2                     COMMAND_RCVD := XECOM_DATA;
207 00A6  2                     COMMAND_RCVD := 0;
208 00AB  2                   END;
209 00AE  2           0      : COMMAND_RCVD := 0;
210 00B6  2         END; (CASE)
211 00CD  2         IF (COMMAND_RCVD = 'b') THEN
212 00D5  2            NEXT_STATE := D;
213 00DA  2       END;
214 00DA  2     END;     (Selector C)
215 00DD  2
216 00DD  2   D: BEGIN
217 00DD  2     (7AUG1985 VERSION)
218 00DD  2     (Here the modem is attempting a 212A handshake on initial connect)
219 00DD  2     (It is generating answer tones)
220 00DD  2     MODEMCHECK;
221 00E0  2     IF MODEMCONNECTED THEN NEXT_STATE := E;
222 00EC  2     IF MODEMCONNECTFAIL THEN NEXT_STATE := J;
223 00FB  2   END;
224 10FB  2
225 00FB  2   E: BEGIN
226 00FB  2     (7AUG1985 VERSION)
227 00FB  2     (Here the modem is transmitting the EKG data)
228 00FB  2     IF (XECOM_COMMAND * [D7] = []) THEN NEXT_STATE := J ELSE (DSR has dropped)
229 010D  2     IF (XECOM_COMMAND * [D1] = [D1]) THEN                  (If RxRDY)
230 0117  2        IF (XECOM_COMMAND * [D7] = [D7]) THEN               (DSR is HI)
231 0121  2        BEGIN                              (A valid byte)
232 0121  2          MINISTATE := 1;
233 0126  2          COMMAND_RCVD := XECOM_DATA;
234 012C  2          IF GAINUP                      THEN INCREASE_GAIN ELSE
235 0138  2          IF GAINDWN                     THEN DECREASE_GAIN ELSE
236 0144  2          IF (COMMAND_RCVD = -2)         THEN GEN_CALSIG    ELSE (0FEH)
237 0152  2          IF (GOTOINTERCON AND ELITEONHOOK)  THEN NEXT_STATE := G ELSE
238 0166  2          IF (GOTOINTERCON AND ELITEOFFHOOK) THEN NEXT_STATE := F ELSE
239 017A  2          IF (COMMAND_RCVD = 05)         THEN SPIKE_ENABLED := TRUE ELSE
240 016A  2 (        IF (COMMAND_RCVD = 06)         THEN SPIKE_ENABLED := FALSE ELSE)
241 018A  2          IF (COMMAND_RCVD = 06)         THEN SPIKE_ENABLED := FALSE;
242 0197  2          IF (COMMAND_RCVD = 07)         THEN SEND_RATE := TRUE;
243 11A4  2        END (If a valid byte)
244 01A7  2        ELSE FLUSHBYTE                 (An info byte left from ??)
245 01AD  2     ELSE COMMAND_RCVD := 00H;         (If nothing is there)
246 01B2  2     IF (NEXT_STATE = E) THEN
247 01BA  2        IF CALLNURSEPRESS THEN
248 01C0  2          IF ELITEOFFHOOK THEN
249 01C6  2            NEXT_STATE := H;           (Pt wants intercom)
```

```
250 01CB  2
251 01CB  2          END;
252 01CE  2      F: BEGIN
253 01CE  2          {15AUG1985 VERSION}
254 01CE  2          {This is the INTERCOM mode}
255 01CE  2          {This is a two stage GO TO INTERCOM DTMF command interpreter}
256 01CE  2          {It looks for a DTMF A followed within 1 second by a DTMF B}
257 01CE  2
258 01CE  2          WORKVAR := BYTE(XECOM_COMMAND * [D7,D1]);
259 01D6  2          CASE WORKVAR OF
260 01D9  2             130    : COMMAND_RCVD := XECOM_DATA;
261 01E2  2             128    : COMMAND_RCVD := 0;
262 01EA  2             2      : BEGIN
263 01EA  2                         COMMAND_RCVD := XECOM_DATA;
264 01F0  2                         COMMAND_RCVD := 0;
265 01F5  2                     END;
266 01F8  2             0      : COMMAND_RCVD := 0,
267 0200  2          END; {CASE}
268 0217  2
269 0217  2          IF (COMMAND_RCVD = 'a') THEN
270 021F  2          {here we wait for 1 second and then look for a DTMF b}
271 021F  2          BEGIN
272 021F  2             SETCLOCK(1);
273 0224  2             REPEAT UNTIL (SECONDS_LEFT = 0);
274 0230  2             WORKVAR := BYTE(XECOM_COMMAND * [D7,D1]);
275 023B  2             CASE WORKVAR OF
276 023B  2                130    : COMMAND_RCVD := XECOM_DATA;
277 0244  2                128    : COMMAND_RCVD := 0;
278 024C  2                2      : BEGIN
279 024C  2                            COMMAND_RCVD := XECOM_DATA;
280 0252  2                            COMMAND_RCVD := 0;
281 0257  2                        END;
282 025A  2                0      : COMMAND_RCVD := 0,
283 0262  2             END; {CASE}
284 0279  2             IF (COMMAND_RCVD = 'b') THEN
285 0281  2                NEXT_STATE := 1;
286 0286  2          END; {IF}
287 0286  2
288 0286  2      END; {State F}
289 0289  2      G: BEGIN
290 0289  2          {7AUG1985 VERSION}
291 0289  2          {Here we are waiting for patient to pick up phone}
292 0289  2          {The bell is ringing on the basestation}
293 0289  2          {No data is being transmitted--the xecom is offhook in DTMF receive}
294 0289  2          {The ring generator is supplying audio to the line for the nurse}
295 0289  2
296 0289  2          {DTMF receiver code ****************************}
297 0289  2          SERVICEBELL;
298 028C  2          IF (D1 IN XECOM_COMMAND) THEN                    {Look for RxRDY}
299 0298  2          BEGIN
300 0298  2             IF (D7 IN XECOM_COMMAND) THEN
301 02A0  2             BEGIN
302 02A0  2                COMMAND_RCVD := XECOM_DATA                 {This is valid }
303 02A6  2             END
304 02A9  2             ELSE
305 02A9  2             BEGIN
306 02A9  2                COMMAND_RCVD := XECOM_DATA,                {Clean the buff}
```

```
307 02AF  2              COMMAND_RCVD := 00H;                                  (A dummy value)
308 02B4  2            END
309 02B4  2          END
310 02B7  2          ELSE
311 02B7  2              COMMAND_RCVD := 00H;                                  (Nothing receiv)
312 02BC  2          (*******************************************)
313 02BC  2
314 02BC  2          IF ((COMMAND_RCVD = 'a') OR (COMMAND_RCVD = '*')) THEN    (GOTO DATA comm)
315 02DE  2              NEXT_STATE := L;                                      (...try to conn)
316 02E3  2
317 02E3  2          (MUST BE FALSE BECAUSE HOOKSWITCH ONLY WORKS THERE)
318 02E3  2          IF (ELITEOFFHOOK AND (RING_STATE = FALSE)) THEN NEXT_STATE := F;
319 02FF  2          END;
320 0302  2      H: BEGIN
321 0302  2          (7AUG1985 VERSION)
322 0302  2          (Here we are waiting for nurse to pick up phone)
323 0302  2          (Data is being transmitted)
324 0302  2
325 0302  2          (Casper command receiver code *********************)
326 0302  2          SERVICERINGBACK;
327 0305  2          IF (XECOM_COMMAND * [D7] = []) THEN NEXT_STATE := J;       (DSR has dropped)
328 0314  2          IF (XECOM_COMMAND * [D1] = [D1]) THEN                      (IF RXRDY)
329 031E  2              IF (XECOM_COMMAND * [D7] = [D7]) THEN                  (DSR is HI)
330 0328  2                                          BEGIN                      (A valid byte)
331 0328  2                                          MINISTATE := 1;
332 032D  2                                          COMMAND_RCVD := XECOM_DATA;
333 0333  2                                          END
334 0336  2              ELSE FLUSHBYTE
335 033C  2          ELSE
336 033C  2              COMMAND_RCVD := 00H;
337 0341  2          (*******************************************************)
338 0341  2
339 0341  2          IF GOTOINTERCOM THEN NEXT_STATE := F;
340 034C  2      (   IF ELITEONHOOK THEN NEXT_STATE := E;   )
341 034C  2
342 034C  2          END;
343 034F  2      I: BEGIN
344 034F  2          (7AUG1985 VERSION)
345 034F  2          (Here the modem is attempting a 212A handshake reconnect)
346 034F  2          (It is generating answer tones)
347 034F  2          MODEMCHECK;
348 0352  2          IF MODEMCONNECTED THEN NEXT_STATE := E;
349 035E  2          IF MODEMCONNECTFAIL THEN NEXT_STATE := J;
350 036A  2          END;
351 036D  2      J: BEGIN
352 036D  2          (7AUG1985 VERSION)
353 036D  2          (Here we look at the DET pin of the Xecom and GO TO K if detected)
354 036D  2          IF (D6 IN XECOM_COMMAND) THEN
355 0379  2          IF (D6 IN XECOM_COMMAND) THEN
356 0381  2          IF (D6 IN XECOM_COMMAND) THEN
357 0389  2          IF (D6 IN XECOM_COMMAND) THEN
358 0391  2          IF (D6 IN XECOM_COMMAND) THEN
359 0399  2          IF (D6 IN XECOM_COMMAND) THEN
360 03A1  2          IF (D6 IN XECOM_COMMAND) THEN
361 03A9  2          IF (D6 IN XECOM_COMMAND) THEN
362 03B1  2          IF (D6 IN XECOM_COMMAND) THEN
363 03B9  2              BEGIN
```

```
364 03B9  2              FOR COUNT := 0 TO 30000 DO ;  (1.2 SEC PAUSE)
365 03DB  2              NEXT_STATE := K;
366 03E0  2              END;
367 03E0  2           IF (NEXT_STATE = J) THEN
368 03E6  2             IF (SECONDS_LEFT = 0) THEN
369 03F4  2                CASE AUTOATOG OF
370 03FA  2                  TRUE: BEGIN
371 03FA  2                          ACTIVELITEOFF;
372 03FD  2                          FOR COUNT := 0 TO 15000 DO ;
373 041F  2                          AUTOATOG := FALSE;
374 0424  2                          END;
375 0427  2                  FALSE: BEGIN
376 0427  2                          ACTIVELITEON;
377 042A  2                          FOR COUNT := 0 TO 15000 DO ;
378 044C  2                          AUTOATOG := TRUE;
379 0451  2                          END;
380 0454  2                  END;
381 0461  2           END;
382 0464  2        K: BEGIN
383 0464  2           (7AUG1985 VERSION)
384 0464  2           (Here we are waiting for modem connect on autoanswer)
385 0464  2           (It is generating answer tones)
386 0464  2           MODEMCHECK;
387 0467  2           IF MODEMCONNECTED  THEN
388 046E  2           BEGIN
389 046E  2             REPEAT UNTIL (D7 IN XECOM_COMMAND);
390 047A  2             NEXT_STATE := E;
391 047F  2           END;
392 047F  2           IF MODEMCONNECTFAIL THEN NEXT_STATE := J;
393 048B  2           END;
394 048E  2        L: BEGIN
395 048E  2           (7AUG1985 VERSION)
396 048E  2           (Here we are waiting for modem reconnect from basestation ringing)
397 048E  2           (It is generating answer tones)
398 048E  2           MODEMCHECK;
399 0491  2           IF MODEMCONNECTED THEN NEXT_STATE := E;
400 049D  2           IF MODEMCONNECTFAIL THEN NEXT_STATE := J;
401 04A9  2           END;
402 04AC  2        O: BEGIN
403 04AC  2           (7AUG1985 VERSION)
404 04AC  2           (Here we are waiting 20 seconds for call nurse button
405 04AC  2            depression. The XeCOM is off the line allowing the
406 04AC  2            Elite to dial. At the end of 20 seconds or at call nurse
407 04AC  2            depression, the XeCOM will come online and will be ready
408 04AC  2            to accept the DTMF a from Casper to go to data)
409 04AC  2           IF ELITEONHOOK        THEN NEXT_STATE := A;
410 04B7  2           IF CALLNURSEPRESS     THEN NEXT_STATE := C;
411 04C2  2           IF (SECONDS_LEFT = 0) THEN NEXT_STATE := C;
412 04D3  2           END;
413 04D6  2        X: BEGIN
414 04D6  2           (7AUG1985 VERSION)
415 04D6  2           (This is a special initialization state that starts everything)
416 04D6  2           START_UP;
417 04D9  2           SAMPLE_ON := FALSE;
418 04DE  2           SEND_RATE := FALSE;
419 04E3  2           RATE_TO_SEND := 40;
420 04E8  2           BLINKA;
```

```
421 04EB  2  (     NEXT_STATE := A;  --replaced for AutoAnswer on initial CN press)
422 04EB  2                          (see lead-in code in main loop)
423 04EB  2        IF CALLNURSEPRESS THEN  NEXT_STATE := J  ELSE NEXT_STATE := A;
424 04FE  2        END;
425 0501  2      OTHERWISE
426 0501  2        (FAULT)
427 0501  2        NEXT_STATE := X;
428 0506  2      END; (CASE)
429 0549  2    END; (EVALUATE_TRIGGERS)
430 0000  1  $PAGE$
431 0000  1  PROCEDURE TRANSFORM_MACHINE;
432 054C  2    (The state of the new states are setup here)
433 054C  2    BEGIN
434 054C  2      CASE NEXT_STATE OF
435 0552  2        A: BEGIN
436 0552  2             (7AUG1985 VERSION)
437 0552  2             (Going into POTS onhook)
438 0552  2             BLINKB;
439 0555  2             XECOM_RESET;                      (Hardware reset of the Xecom an)
440 0558  2             BLINKA;
441 055B  2
442 055B  2             ELITEONLINE;
443 055E  2
444 055E  2             STOPBELL; STOPRINGBACK;
445 0564  2
446 0564  2             MODEMCONNECTFAIL := FALSE;
447 0569  2             MODEMCONNECTED := FALSE;
448 056E  2             PHYSCONNECTED := FALSE;
449 0573  2             PHYSCONNECTFAIL := FALSE;
450 0578  2
451 0578  2             SPIKE_ENABLED := FALSE;
452 057D  2             CNLITEOFF;
453 0580  2             ACTIVELITEOFF;
454 0583  2           END;
455 0586  2        B: BEGIN
456 0586  2             (7AUG1985 VERSION)
457 0586  2             (SETUP TO COUNT RINGS AND LOOK FOR ELITEOFFHOOK)
458 0586  2             RING_COUNT := 1;
459 058B  2           END;
460 058E  2        C: BEGIN
461 058E  2             (7AUG1985 VERSION)
462 058E  2             (Going into ready for 1st DTMF mode)
463 058E  2             INTERCOM;                         (Eliteonline, DTMF receive, in0)
464 0591  2             ACTIVELITEOFF;
465 0594  2           END;
466 0597  2        D: BEGIN
467 0597  2             (7AUG1985 VERSION)
468 0597  2             (Going into 1st connect attempt)
469 0597  2             CNLITEOFF;
470 059A  2             CONNECT_RESULT := DATALINK;       (DATALINK sets up answer mode a)
471 05A0  2                                               (This also will enable interrup)
472 05A0  2           END;
473 05A3  2        E: BEGIN
474 05A3  2             (7AUG1985 VERSION)
475 05A3  2             (Going into Data Transmitting)
476 05A3  2             ACTIVELITEON;                     (Turn on lite to let user know )
477 05A6  2             STOPBELL; STOPRINGBACK;
```

```
478 05AC  2          INIT_QUEUE;
479 05AF  2          IF (STATE = H) THEN PTGAVEUP := TRUE; (Serviced & reset by ISR)
480 05BC  2        END;
481 05BF  2      F: BEGIN
482 05BF  2        (7AUG1985 VERSION)
483 05BF  2        (Going into INTERCOM)
484 05BF  2          CNLITEOFF;
485 05C2  2          ACTIVELITEOFF;
486 05C5  2          STOPBELL; STOPRINGBACK;
487 05CB  2          INTERCOM;
488 05CE  2        END;
489 05D1  2
490 05D1  2      G: BEGIN
491 05D1  2        (7AUG1985 VERSION)
492 05D1  2        (Going into BASESTATION RINGING)
493 05D1  2        (BASESTATION RINGING doesn't send data in this revision)
494 05D1  2          CNLITEOFF;
495 05D4  2          ACTIVELITEOFF;
496 05D7  2          INTERCOM;                    (Eliteonline, DIM receive, ino)
497 05DA  2          STARTBELL;
498 05DD  2        END;
499 05E0  2
500 05E0  2      H: BEGIN
501 05E0  2        (7AUG1985 VERSION)
502 05E0  2        (Going into WAITING FOR NURSE (data transmitting))
503 05E0  2          JUNK := XECOM_DATA;
504 05E6  2          CNLITEON;
505 05E9  2          PTCALLING := TRUE; (This is serviced and reset by the ISR)
506 05EE  2          STARTRINGBACK;
507 05F1  2        END;
508 05F4  2
509 05F4  2      I: BEGIN
510 05F4  2        (7AUG1985 VERSION)
511 05F4  2        (Going into modem connect from intercom)
512 05F4  2          CONNECT_RESULT := DATALINK;
513 05FA  2        END;
514 05FD  2
515 05FD  2      J: BEGIN
516 05FD  2        (15AUG1985 VERSION)
517 05FD  2        (Going into AutoAnswer)
518 05FD  2          DISABLE_75; (17 Sept 85 update for late_sense)
519 0600  2
520 0600  2          ELITEOFFLINE;
521 0603  2
522 0603  2          (This does both a hardware and software reset)
523 0603  2          XECOM_RESET;
524 0606  2
525 0606  2
526 0606  2          ACTIVELITEOFF;
527 0609  2          CNLITEOFF;
528 060C  2
529 060C  2          STOPBELL; STOPRINGBACK;
530 0612  2
531 0612  2          (About a 1.2 second pause)
532 0612  2          FOR ID := 1 TO 30000 DO;
533 0634  2
534 0634  2          MODEMCONNECTFAIL := FALSE;
```

```
535 0639  2            MODEMCONNECTED := FALSE;
536 063E  2            PHYSCONNECTED := FALSE;
537 0643  2            PHYSCONNECTFAIL := FALSE;
538 0648  2
539 0648  2            ACTIVELITEON,
540 064B  2            AUTOATOG := TRUE; (Lite is on)
541 0650  2            SETCLOCK(1);
542 0655  2
543 0655  2          END;
544 0658  2     K: BEGIN
545 0658  2          (7AUG1985 VERSION)
546 0658  2          (Going into modem connect from autoanswer)
547 0658  2
548 0658  2          ACTIVELITEOFF;
549 065B  2          CNLITEOFF,
550 065E  2
551 065E  2          CONNECT_RESULT := DATALINK;
552 0664  2            ( IS INFORMATION PRESENT ? )
553 0664  2          IF (NOT(D7 IN XECOM_COMMAND) AND (D1 IN XECOM_COMMAND))
554 0679  2            THEN CONNECT_RESULT := XECOM_DATA;
555 067F  2          END;
556 0682  2     L: BEGIN
557 0682  2          (7AUG1985 VERSION)
558 0682  2          (Going into modem connect from basestation ringing)
559 0682  2          CONNECT_RESULT := DATALINK;
560 0688  2          END;
561 068B  2     O: BEGIN
562 068B  2          (7AUG1985 VERSION)
563 068B  2          (Setup for a 20 second pause for normal POTS w/o Xecom online)
564 068B  2          SETCLOCK(20);
565 0690  2          END;
566 0693  2
567 0693  2        OTHERWISE
568 0693  2          (FAULT)
569 0693  2          NEXT_STATE := X;
570 0698  2        END; (CASE)
571 06D9  2      END; (TRANSFORM_MACHINE)
572 0000  1  $PAGE$
573 06DE  1  BEGIN (Main procedure)
574 06DE  1
575 06DE  1    (Initialization)
576 06DE  1    STATE := X;
577 06E6  1    (NEXT_STATE := A;     -- replaced for AutoAnswer on CN press)
578 06E6  1    RM_STATE := RESET;
579 06EB  1    NEXT_RM_STATE := WAIT;
580 06F0  1
581 06F0  1    (Mainloop)
582 06F0  1    WHILE TIME_GOES_BY DO BEGIN
583 06F0  1
584 06F0  1      (Rate monitor operation background tasks)
585 06F0  1      CURRENT_RMS_OPS;
586 06F3  1      IF RM_STATE () NEXT_RM_STATE
587 06FD  1        THEN BEGIN
588 06FD  1          CHANGE_RMS;
589 0700  1          RM_STATE := NEXT_RM_STATE;
590 0706  1          END;
591 0706  1
```

```
592 0706  1     (Basestation operation background tasks)
593 0706  1     (DISPSTATE;                                    )
594 0706  1
595 0706  1     IF CALLNURSEPRESS THEN
596 070C  1         BEGIN
597 070C  1         IF (SECONDS_LEFT=0) THEN
598 0718  1             BEGIN
599 0718  1             IF VOICEHOOKFLAG=TRUE THEN
600 0720  1                 BEGIN
601 0720  1                 SETCLOCK(1);
602 0725  1                 VOICEHOOKFLAG:=FALSE;
603 072A  1                 VOICE_ONHOOK;
604 072D  1                 CALLITEOFF;
605 0730  1                 END
606 0733  1                 ELSE BEGIN
607 0733  1                     SETCLOCK(1);
608 0738  1                     VOICEHOOKFLAG:=TRUE;
609 073D  1                     VOICE_OFFHOOK,
610 0740  1                     CALLITEON,
611 0743  1                     END;
612 0743  1             END;
613 0743  1         END;
614 0743  1     EVALUATE_TRIGGERS;
615 0746  1     IF STATE () NEXT_STATE
616 0750  1     THEN BEGIN
617 0750  1         TRANSFORM_MACHINE;
618 0753  1         STATE := NEXT_STATE,
619 0759  1         END;
620 0759  1
621 0759  1     END;
622 075C  1
623 075C  1 END.
624 0000  1 $GLOBPROC OFF$ end of compilation, number of errors=    0

FILE AUX3;BOPRO:     H. 64000 - Pascal     "8085" Code Generator 1 0000  1  "8085"
 2 0000  1  $EXTENSIONS ON$
 3 0000  1  $SEPARATE ON$
 4 0000  1  $OPTIMIZE OFF$
 5 0000  1  PROGRAM AUX;
 6 0000  1  (This code provides various auxilary functions for the system.)
 7 0000  1  (It also includes the startup code)
 8 0000  1  TYPE
 9 0000  1              (0 1 2 3 4 5 6 7 8 9 A B C D E F)
10 0000  1     STATE_TYPE = (A,B,C,D,E,F,G,H,I,J,K,L,M,N,O,X);
11 0000  1     BITS       = (D0,D1,D2,D3,D4,D5,D6,D7);
12 0000  1  VAR
13 0000  1
14 0000  1  $EXTVAR ON$
15 0000  1  XECOM_DATA    : BYTE;
16 0000  1  A8155         : BYTE;
17 0000  1  TIMER_LO      : BYTE;
18 0000  1  TIMER_HI      : BYTE;
19 0000  1  PORT_A        : SET OF BITS;
```

```
20 0000  1  PORT_B            : SET OF BITS;
21 0000  1  PORT_C            : SET OF BITS;
22 0000  1  CTC_MODE          : BYTE;
23 0000  1  CTC_0             : BYTE;
24 0000  1  CTC_1             : BYTE,
25 0000  1  CTC_2             : BYTE,
26 0000  1  A_GAIN,
27 0000  1  A_AMP             : BYTE;
28 0000  1  STATE             : STATE_TYPE;
29 0000  1  NEXT_STATE        : STATE_TYPE;
30 0000  1  MINISTATE         : BYTE;
31 0000  1  INTRMSK           : SET OF BITS;
32 0000  1  $EXTVAR OFF$
33 0000  1
34 0000  1  $GLOBVAR ON$
35 0000  1  VOICEHOOKFLAG     : BOOLEAN;
36 0000  1  SECONDS_LEFT      : INTEGER;    (This is a generalized 1 sec countdown)
37 0003  1  COMMAND_RCVD      : BYTE;
38 0004  1
39 0004  1  (Here are flags that are set and used for generation of special)
40 0004  1  (codes embedded in the data stream)
41 0004  1
42 0004  1     RINGNURSE,
43 0004  1     PTCALLING,
44 0004  1     PTWANTSDT,
45 0004  1     PTREADY,
46 0004  1     PTGAVEUP        : BOOLEAN;
47 0009  1
48 0009  1
49 0009  1  (Variables for the calibration signal generator)
50 0009  1  (Set in GEN_CALSIG here)
51 0009  1     PRECALVAL      : BYTE;     (Prestep value -- raw A/D value)
52 000A  1     STEPCALVAL     : BYTE;     (The step value)
53 000B  1     POSTCALVAL     : BYTE;     (Poststep value)
54 000C  1     PRECOUNT       : BYTE;     (Number of 10 ms ticks for prestep)
55 000D  1     STEPCOUNT      : BYTE;     (Number on the step)
56 000E  1     POSTCOUNT      : BYTE;     (Number after the step)
57 000F  1     CALGENCOUNT    : BYTE;     (Total calibration routine tick count)
58 0010  1
59 0010  1  $ORG 0C100H$
60 0010  1  DISPCURSOR        : BYTE;
61 0010  1  $END_ORG$
62 0010  1
63 0010  1  $ORG 0C104H$
64 0010  1  DISP1             : BYTE;
65 0010  1  DISP2             : BYTE;
66 0010  1  DISP3             : BYTE;
67 0010  1  DISP4             : BYTE;
68 0010  1  $END_ORG$
69 0000  1  PROCEDURE DISABLE_75;        EXTERNAL; (Rate sense stuff)
70 0000  1  PROCEDURE XECOM_RESET;       EXTERNAL;
71 0000  1
72 0000  1  $PAGE$
73 0000  1  $GLOBPROC ON$
74 0000  1  (These procedures manipulate the 'front panel' display)
75 0000  1  PROCEDURE CLEARDISP;
76 0000  2    (This routine clears a display resident in the unused RAM socket)
```

```
 77 0000 2 BEGIN
 78 0000 2   DISPCURSOR := 00H;
 79 0005 2   DISP1 := 20H;
 80 000A 2   DISP2 := 20H;
 81 000F 2   DISP3 := 20H;
 82 0014 2   DISP4 := 20H;
 83 0019 2 END;
 84 0000 1
 85 0000 1 PROCEDURE DISPSTATE;
 86 0000 2 (This procedure displays the state in ASCII on the RAM socket disp)
 87 0000 2 (STATE is displayed in the 2nd digit; NEXT_STATE in the 4th)
 88 0000 2 VAR
 89 0000 2   DISP : BYTE;
 90 001A 2 BEGIN
 91 001A 2   CLEARDISP;
 92 001D 2   CASE STATE OF
 93 0023 2     A: DISP := 'A';
 94 002B 2     B: DISP := 'B';
 95 0033 2     C: DISP := 'C';
 96 003B 2     D: DISP := 'D';
 97 0043 2     E: DISP := 'E';
 98 004B 2     F: DISP := 'F';
 99 0053 2     G: DISP := 'G';
100 005B 2     H: DISP := 'H';
101 0063 2     I: DISP := 'I';
102 006B 2     J: DISP := 'J';
103 0073 2     K: DISP := 'K';
104 007B 2     L: DISP := 'L';
105 0083 2     M: DISP := 'M';
106 008B 2     N: DISP := 'N';
107 0093 2     O: DISP := 'O';
108 009B 2     X: DISP := 'X';
109 00A3 2   END; (CASE)
110 00E3 2   DISP3 := DISP;
111 00E9 2   CASE NEXT_STATE OF
112 00EF 2     A: DISP := 'A';
113 00F7 2     B: DISP := 'B';
114 00FF 2     C: DISP := 'C';
115 0107 2     D: DISP := 'D';
116 010F 2     E: DISP := 'E';
117 0117 2     F: DISP := 'F';
118 011F 2     G: DISP := 'G';
119 0127 2     H: DISP := 'H';
120 012F 2     I: DISP := 'I';
121 0137 2     J: DISP := 'J';
122 013F 2     K: DISP := 'K';
123 0147 2     L: DISP := 'L';
124 014F 2     M: DISP := 'M';
125 0157 2     N: DISP := 'N';
126 015F 2     O: DISP := 'O';
127 0167 2     X: DISP := 'X';
128 016F 2   END; (CASE)
129 01AF 2   DISP1 := DISP;
130 01B5 2 END;
131 0000 1
132 0000 1 $PAGE$
```

```
133 0000  1  FUNCTION CALLNURSEPRESS       : BOOLEAN;
134 0001  2  VAR
135 0001  2    I : INTEGER;
136 0003  2    CN_P : BOOLEAN;
137 01B6  2  BEGIN
138 01B6  2    CN_P := FALSE;
139 01BB  2  ( FOR I := 1 TO 20   DO BEGIN                              )
140 01BB  2      IF (PORT_B * [D1] = [D1]) THEN CN_P := TRUE,
141 01CA  2  (   IF CN_P THEN I:= 20  ;                                 )
142 01CA  2  ( END;                                                     )
143 01CA  2    CALLNURSEPRESS := CN_P;
144 01D8  2  END;
145 0000  1  $PAGE$
146 0000  1  (INDICATE IF A COMMAND IS RECEIVED FROM CASPER)
147 0000  1
148 0000  1  FUNCTION CALGEN: BOOLEAN;
149 01D2  2  BEGIN
150 01D2  2    CALGEN := FALSE;
151 01D7  2    IF COMMAND_RCVD = 0FEH THEN CALGEN := TRUE;
152 01EB  2  END;
153 0000  1
154 0000  1  FUNCTION GOTOINTERCOM         : BOOLEAN;
155 01F0  2  BEGIN
156 01F0  2    GOTOINTERCOM := FALSE;
157 01F5  2    IF COMMAND_RCVD = 02H THEN GOTOINTERCOM := TRUE;
158 0202  2  END;
159 0000  1
160 0000  1  FUNCTION CANCELINTERCOM       : BOOLEAN;
161 0207  2  BEGIN
162 0207  2    CANCELINTERCOM := FALSE;
163 020C  2    IF COMMAND_RCVD = 05H THEN CANCELINTERCOM := TRUE;
164 0219  2  END;
165 0000  1
166 0000  1  FUNCTION RELEASEBASE          : BOOLEAN,
167 021E  2  BEGIN
168 021E  2    RELEASEBASE := FALSE;
169 0223  2    IF COMMAND_RCVD = 04H THEN RELEASEBASE := TRUE;
170 0230  2  END;
171 0000  1
172 0000  1  FUNCTION NURSECALLING : BOOLEAN;
173 0235  2  BEGIN
174 0235  2    NURSECALLING := FALSE;
175 023A  2    IF COMMAND_RCVD = 01H THEN NURSECALLING := TRUE;
176 0247  2  END;
177 0000  1
178 0000  1  FUNCTION GAINUP : BOOLEAN;
179 024C  2  BEGIN
180 024C  2    GAINUP := FALSE;
181 0251  2    IF COMMAND_RCVD = 0AH THEN GAINUP := TRUE;
182 025E  2  END;
183 0000  1
184 0000  1  FUNCTION GAINDWN : BOOLEAN;
185 0263  2  BEGIN
186 0263  2    GAINDWN := FALSE,
187 0268  2    IF COMMAND_RCVD = 0BH THEN GAINDWN := TRUE,
188 0275  2  END;
189 0000  1  $PAGE$
```

```
190 0000  1  PROCEDURE ENABLE; EXTERNAL;
191 0000  1  PROCEDURE DISABLE; EXTERNAL;
192 0000  1  PROCEDURE SMASK;  EXTERNAL;
193 0000  1
194 0000  1  $PAGE$
195 0000  1  (1 Second timer countdown procedures -- use the 5.5 interrupt & CTC)
196 0000  1  PROCEDURE TICK;
197 027A  2  BEGIN
198 027A  2    SECONDS_LEFT := SECONDS_LEFT - 1;
199 0287  2    IF (SECONDS_LEFT = 0) THEN BEGIN
200 0290  2      DISABLE;
201 0293  2      INTRMSK := INTRMSK + [D3,D0]; (Mask 5.5 if done)
202 029B  2      SMASK;
203 029E  2      ENABLE;
204 02A1  2    END;
205 02A1  2  END;
206 0000  1
207 0000  1  PROCEDURE SETCLOCK(SECONDS:INTEGER);
208 02AB  2  BEGIN
209 02AB  2    DISABLE;
210 02AE  2    SECONDS_LEFT := SECONDS;
211 02B4  2    INTRMSK := (INTRMSK + [D3]) - [D0],       (Unmask 5.5)
212 02C0  2    SMASK;
213 02C3  2    CTC_0 := 020H;                            (Restart the 1 second timer channel)
214 02C8  2    CTC_0 := 000H;                            (...it takes a 16 bit load...)
215 02CD  2    ENABLE;
216 02D0  2  END;
217 0000  1
218 0000  1  PROCEDURE STOPCLOCK;
219 02D5  2  (This procedure merely masks the 5.5 interrupt which occurs at 1 )
220 02D5  2  (second intervals)
221 02D5  2  BEGIN
222 02D5  2    DISABLE;
223 02D8  2    INTRMSK := INTRMSK + [D3,D0]; (Mask 5.5 if done)
224 02E0  2    SMASK;
225 02E3  2    ENABLE;
226 02E6  2  END;
227 0000  1
228 0000  1  $PAGE$
229 0000  1  PROCEDURE SENDBYTEUP(B:BYTE);
230 02F0  2  BEGIN
231 02F0  2  END;
232 0000  1
233 0000  1  PROCEDURE SENDTOCASPER(A:BYTE);
234 02FE  2  BEGIN
235 02FE  2    SENDBYTEUP(0FEH);
236 0303  2    SENDBYTEUP(A);
237 0308  2  END;
238 0000  1
239 0000  1  $PAGE$
240 0000  1
241 0000  1
242 0000  1  PROCEDURE ENABLE_EKG;
243 030E  2  BEGIN
244 030E  2    (Unmask only the 7.5 & reset the 7.5 FF)
245 030E  2    (The 7.5 unmasks the 6.5)
246 030E  2    INTRMSK := (INTRMSK - [D2]) + [D4,D3,D1,D0];
```

```
247 031B  2    SMASK;
248 031E  2    END;
249 0000  1
250 0000  1  PROCEDURE DISABLE_EKG;
251 031F  2  BEGIN
252 031F  2    (Mask the 7.5 and 6.5)
253 031F  2    ( DISABLE_TXRX; )
254 031F  2    INTRMSK := INTRMSK + [D3,D2,D1];
255 0327  2    SMASK;
256 032A  2  END;
257 0000  1
258 0000  1  $PAGE$
259 0000  1
260 0000  1  PROCEDURE INCREASE_GAIN;
261 032B  2  BEGIN
262 032B  2    A_GAIN := A_GAIN + 1;
263 0333  2    IF A_GAIN > 15 THEN A_GAIN := 15;
264 033F  2    A_AMP := A_GAIN;
265 0345  2  END;
266 0000  1
267 0000  1  PROCEDURE DECREASE_GAIN;
268 0346  2  BEGIN
269 0346  2    A_GAIN := A_GAIN - 1;
270 034E  2    IF A_GAIN < 0 THEN A_GAIN := 0;
271 035A  2    A_AMP := A_GAIN;
272 0360  2  END;
273 0000  1
274 0000  1  PROCEDURE GEN_CALSIG;
275 0361  2  BEGIN
276 0361  2    (This should generated a value representing a 1 mV signal @ electrodes)
277 0361  2    (It should take into account the gain setting)
278 0361  2    PRECALVAL := 127;
279 0366  2    STEPCALVAL := 127 + (2 * A_GAIN);
280 0373  2    POSTCALVAL := PRECALVAL;
281 0379  2    PRECOUNT := 2;
282 037E  2    STEPCOUNT := 10;
283 0383  2    POSTCOUNT := 2;
284 0388  2    DISABLE;
285 038B  2    CALGENCOUNT := PRECOUNT + STEPCOUNT + POSTCOUNT;
286 0399  2    ENABLE;
287 039C  2  END;
288 0000  1
289 0000  1  $PAGE$
290 0000  1  (Procedures to manipulate lights & relays, etc.)
291 0000  1  PROCEDURE ACTIVELITEON;
292 039D  2  BEGIN
293 039D  2    PORT_A := PORT_A + [D1];
294 03A5  2  END;
295 0000  1
296 0000  1  PROCEDURE ACTIVELITEOFF;
297 03A6  2  BEGIN
298 03A6  2    PORT_A := PORT_A - [D1];
299 03B0  2  END;
300 0000  1
301 0000  1  PROCEDURE CALITEON;
302 03B1  2  BEGIN
303 03B1  2    PORT_A := PORT_A + [D0];
304 03B9  2  END;
```

```
305 0000  1
306 0000  1  PROCEDURE CNLITEOFF;
307 03BA  2  BEGIN
308 03BA  2    PORT_A := PORT_A - [D0];
309 03C4  2  END;
310 0000  1
311 0000  1  PROCEDURE BLINKA;
312 03C5  2  BEGIN
313 03C5  2    ACTIVELITEON;
314 03C8  2    CNLITEOFF;
315 03CB  2    SETCLOCK(1);
316 03D0  2    WHILE (SECONDS_LEFT () 0) DO ; (busy waiting, can't go any where till done)
317 03DF  2  END;
318 0000  1
319 0000  1  PROCEDURE BLINKB;
320 03E2  2  BEGIN
321 03E2  2    ACTIVELITEOFF;
322 03E5  2    CNLITEON;
323 03E8  2    SETCLOCK(1);
324 03ED  2    WHILE (SECONDS_LEFT () 0) DO ; (busy waiting, can't go any where till done)
325 03FC  2  END;
326 0000  1
327 0000  1
328 0000  1  PROCEDURE VOICE_OFFHOOK;
329 03FF  2  BEGIN
330 03FF  2    PORT_A := PORT_A + [D5];
331 0407  2  END;
332 0000  1
333 0000  1  PROCEDURE VOICE_ONHOOK;
334 0408  2  BEGIN
335 0408  2    PORT_A := PORT_A - [D5];
336 0412  2  END;
337 0000  1
338 0000  1  $PAGE$
339 0000  1  (This procedure is used for initialization of the box)
340 0000  1  PROCEDURE START_UP;
341 0413  2  BEGIN
342 0413  2    DISABLE;
343 0416  2
344 0416  2    CLEARDISP;
345 0419  2
346 0419  2    (START UP THE 8155)
347 0419  2    TIMER_LO := 03H;
348 041E  2    TIMER_HI := 040H;
349 0423  2    (Port A : output )
350 0423  2    (Port B : input )
351 0423  2    (Port C : output )
352 0423  2    (Port A & B interrupts disabled )
353 0423  2    (Start the timer )
354 0423  2    A8155 := 0CDH;
355 0428  2    PORT_A := [];
356 042D  2    (Port C controls the 8253 gates )
357 042D  2    PORT_C := [D2,D1,D0];
358 0432  2    (START THE 5MS TIMER)
359 0432  2    (This runs off the 1 MHZ clock)
360 0432  2    CTC_MODE := 01110110B;
361 0437  2
```

```
362 0437  2    {190 HZ = 5263 US = 148FH }
363 0437  2    { CTC_1 := 08FH; }
364 0437  2    { CTC_1 := 014H; }
365 0437  2
366 0437  2    {200 HZ = 5000 US = 1388H }
367 0437  2    { CTC_1 := 088H; }
368 0437  2    { CTC_1 := 013H; }
369 0437  2
370 0437  2    {300 HZ = 3333 US = 0D05H }
371 0437  2      CTC_1 := 05H;
372 043C  2      CTC_1 := 0DH;
373 0441  2
374 0441  2    {Test mode -- about 15 Hz}
375 0441  2    { CTC_1 := 0FEH;              }
376 0441  2    { CTC_1 := 0FFH;              }
377 0441  2
378 0441  2      {START THE 20HZ TIMER}
379 0441  2      {This runs off the 1 MHZ clock}
380 0441  2      CTC_MODE := 10110110B;
381 0446  2      CTC_2 := 050H;
382 044B  2      CTC_2 := 0C3H;
383 0450  2
384 0450  2
385 0450  2      {MASK ALL THE INTERRUPTS}
386 0450  2      {MAKE SOD LO}
387 0450  2      {RESET THE 7.5 LATCH}
388 0450  2
389 0450  2    { INTRMSK := [D3,D2,D1,D0, D4, D6];   }
390 0450  2    { SMASK;                              }
391 0450  2    { ENABLE;                             }
392 0450  2
393 0450  2      DISABLE_75;
394 0453  2
395 0453  2      {THE 1 SECOND TIMER IS STARTED IN ISR55}
396 0453  2      {THESE NEED TO BE DONE FIRST TIME TO SETUP}
397 0453  2      {This runs off the 20HZ clock}
398 0453  2      CTC_MODE := 00110000B;
399 0458  2      CTC_0 := 20; {FOR THE 1 SECOND TIME}
400 045D  2      CTC_0 := 0;
401 0462  2
402 0462  2            VOICEHOOKFLAG:=FALSE;
403 0467  2
404 0467  2            RINGNURSE  := FALSE;
405 046C  2            PTCALLING  := FALSE;
406 0471  2            PTWANTSDT  := FALSE;
407 0476  2            PTREADY    := FALSE;
408 047B  2            PTGAVEUP   := FALSE;
409 0480  2
410 0480  2      A_GAIN := 3;
411 0485  2      A_AMP  := 3;
412 048A  2
413 048A  2    END; {of startup}
414 0000  1
415 0000  1  PROCEDURE FLUSHBYTE;
416 048B  2  BEGIN
417 048B  2    COMMAND_RCVD := XECOM_DATA;
```

```
418 0491  2      MINISTATE := 2;
419 0496  2      COMMAND_RCVD := 0H;
420 049B  2    END;
421 0000  1
422 0000  1  .

End of compilation, number of errors=    0

FILE: MIAMIO:BULBS1    HI 64000 - Pascal    "8085" Code Generator 1 0000  1  "8085"
  2 0000  1  $TITLE "MIAMI BASESTATION PROGRAM -- MEMORY MAPPED IO"$
  3 0000  1  PROGRAM MIAMIO;
  4 0000  1
  5 0000  1  $EXTENSIONS ON$
  6 0000  1  $SEPARATE ON$
  7 0000  1
  8 0000  1  CONST
  9 0000  1    EKG1         = 0F800H;
 10 0000  1    EKG2         = 0F801H;
 11 0000  1    FEKG1        = 0F803H;
 12 0000  1    FEKG2        = 0F802H;
 13 0000  1
 14 0000  1  TYPE
 15 0000  1    BITTYPE      = (D0,D1,D2,D3,D4,D5,D6,D7);
 16 0000  1    S8           = SET OF BITTYPE;
 17 0000  1    CHAN_TYPE    = (CHAN_A,CHAN_B);
 18 0000  1    MODE_TYPE    = (MODE_A,MODE_B,MODE_AB);
 19 0000  1    BYTEPTR      = ^BYTE;
 20 0000  1    RINGINDEX    = INTEGER;
 21 0000  1
 22 0000  1
 23 0000  1  VAR
 24 0000  1  $GLOBVAR ON$
 25 0000  1  $PAGE$
 26 0000  1  (-------------------------------------------------------)
 27 0000  1  (****************** MEMORY_MAPPED I/O ******************)
 28 0000  1  (-------------------------------------------------------)
 29 0000  1
 30 0000  1  $ORG 0F100H$
 31 0000  1
 32 0000  1  (-------------------------------------------------------)
 33 0000  1               (THE 8155 PARALLEL I/O TIMER)
 34 0000  1  (-------------------------------------------------------)
 35 0000  1    A8155        : RECORD CASE BOOLEAN OF
 36 0000  2      TRUE : ( STS : BYTE );
 37 0000  2      FALSE: ( CMD : BYTE );
 38 0000  1    END; (RECORD)
 39 0000  1    PORT_A       : S8;
 40 0000  1    PORT_B       : S8;
 41 0000  1    PORT_C       : S8;
 42 0000  1    TIMER_LO     : BYTE;
 43 0000  1    TIMER_HI     : BYTE;
 44 0000  1
 45 0000  1  $END_ORG$
 46 0000  1  $ORG 0F200H$
 47 0000  1
```

```
48 0000  1  {--------------------------------------------------------------}
49 0000  1                  (THIS IS THE 8253 COUNTER/TIMER CHIP)
50 0000  1  {--------------------------------------------------------------}
51 0000  1
52 0000  1  CTC_0           : BYTE;
53 0000  1  CTC_1           : BYTE;
54 0000  1  CTC_2           : BYTE;
55 0000  1  CTC_MODE        : S8;
56 0000  1
57 0000  1  $END_ORG$
58 0000  1  $ORG 0F400H$
59 0000  1
60 0000  1  {--------------------------------------------------------------}
61 0000  1                  (THIS IS THE NS MM58167 REAL TIME CLOCK)
62 0000  1  {--------------------------------------------------------------}
63 0000  1  (THESE ARE COUNTER VALUES)
64 0000  1  C_RTC_MS        : BYTE; (MILLISECONDS)
65 0000  1  C_RTC_CS        : BYTE; (CENTISECONDS)
66 0000  1  C_RTC_S         : BYTE; (SECONDS)
67 0000  1  C_RTC_MIN       : BYTE; (MINUTES)
68 0000  1  C_RTC_HRS       : BYTE; (HOURS)
69 0000  1  C_RTC_DOW       : BYTE; (DAY OF WEEK)
70 0000  1  C_RTC_DOM       : BYTE; (DAY OF MONTH)
71 0000  1  C_RTC_MON       : BYTE; (MONTH)
72 0000  1
73 0000  1  (THESE ARE LATCH VALUES)
74 0000  1  L_RTC_MS        : BYTE; (MILLISECONDS)
75 0000  1  L_RTC_CS        : BYTE; (CENTISECONDS)
76 0000  1  L_RTC_S         : BYTE; (SECONDS)
77 0000  1  L_RTC_MIN       : BYTE; (MINUTES)
78 0000  1  L_RTC_HRS       : BYTE; (HOURS)
79 0000  1  L_RTC_DOW       : BYTE; (DAY OF WEEK)
80 0000  1  L_RTC_DOM       : BYTE; (DAY OF MONTH)
81 0000  1  L_RTC_MON       : BYTE; (MONTH)
82 0000  1
83 0000  1  RTC_INTRSTS     : S8;
84 0000  1  RTC_INTRMSK     : S8;
85 0000  1
86 0000  1  COUNTER_RST     : BYTE; (COUNTER RESET)
87 0000  1  LATCH_RST       : BYTE; (LATCH RESET)
88 0000  1  RTC_STS_BIT     : BYTE;
89 0000  1  GO_COMMAND      : BYTE;
90 0000  1  STANDBY_INTR    : BYTE;
91 0000  1  SECOND_COUNTER  : BYTE;
92 0000  1
93 0000  1  $END_ORG$
94 0000  1  $ORG 0F600H$
95 0000  1
96 0000  1  {--------------------------------------------------------------}
97 0000  1                  (XECOM XE1201/1203 MOSART UART/MODEM)
98 0000  1  {--------------------------------------------------------------}
99 0000  1  XECOM_DATA      : BYTE;
100 0000 1  XECOM_COMMAND   : S8;
101 0000 1
102 0000 1  $END_ORG$
103 0000 1  $ORG 0F800H$
104 0000 1
```

```
105 0000  1  {------------------------------------------------}
106 0000  1               (ANALOG DEVICES AD7581 8 CHANNEL ADC)
107 0000  1  {------------------------------------------------}
108 0000  1  (THIS CHIP LOOKS LIKE 8 MEMORY LOCATIONS)
109 0000  1  CHAN_0 : BYTE;
110 0000  1  CHAN_1 : BYTE;
111 0000  1  CHAN_2 : BYTE;
112 0000  1  CHAN_3 : BYTE;
113 0000  1  CHAN_4 : BYTE;
114 0000  1  CHAN_5 : BYTE;
115 0000  1  CHAN_6 : BYTE;
116 0000  1  CHAN_7 : BYTE;
117 0000  1
118 0000  1  $END_ORG$
119 0000  1  $ORG 0FA00H$
120 0000  1
121 0000  1  {------------------------------------------------}
122 0000  1    (ANALOG DEVICES AD7524 MULTIPLYING DAC (DIG CONTRLD GAIN) #1)
123 0000  1  {------------------------------------------------}
124 0000  1  A_AMP : BYTE;
125 0000  1
126 0000  1  $END_ORG$
127 0000  1  $ORG 0FC00H$
128 0000  1
129 0000  1  {------------------------------------------------}
130 0000  1    (ANALOG DEVICES AD7524 MULTIPLYING DAC (DIG CONTRLD GAIN) #2)
131 0000  1  {------------------------------------------------}
132 0000  1  B_AMP : BYTE;
133 0000  1
134 0000  1  $END_ORG$
135 0000  1  $ORG 0FE00H$
136 0000  1
137 0000  1  {------------------------------------------------}
138 0000  1                (UNUSED CHIP SELECT DECODE LOCATION)
139 0000  1  {------------------------------------------------}
140 0000  1  WHO : BYTE;
141 0000  1
142 0000  1  $END_ORG$
143 0000  1
144 0000  1  .
```

End of compilation, number of errors=    0

FILE: CLOCKIO:BOBBS;    H: 64060 - Pascal    "8085" Code Generator

```
 1 0000  1  "8085"
 2 0000  1  PROGRAM CLOCKIO;
 3 0000  1  $EXTENSIONS ON$
 4 0000  1  $OPTIMIZE ON$
 5 0000  1  $SEPARATE ON$
 6 0000  1
 7 0000  1  (These are the input sampling routines for the Basestation)
 8 0000  1
 9 0000  1  CONST
10 0000  1    SPIKECODE = 0FFH;
11 0000  1    ALARM_TRIP = 4; (# of SID samples out of last 10 for Pt alert)
12 0000  1    ALARM_REFR = 5; (# of seconds refractory for retrip of alarm)
```

```
13 1000  1    SPIKE_REFR = 8; (# of 10 ms ticks before spike retrigger possible)
14 0000  1
15 0000  1  TYPE
16 0000  1    INTRBITS   = (M5,M6,M7,IE,I5,I6,I7,SID);
17 0000  1
18 0000  1  VAR
19 0000  1  $EXTVAR ON$
20 0000  1    INTRMSK       : SET OF INTRBITS;
21 0000  1    CALGENCOUNT   : BYTE;          (AUX)
22 0000  1    PRECALVAL     : BYTE;          (AUX)
23 0000  1    STEPCALVAL    : BYTE;          (AUX)
24 0000  1    POSTCALVAL    : BYTE;          (AUX)
25 0000  1    PRECOUNT      : BYTE;          (AUX)
26 0000  1    STEPCOUNT     : BYTE;          (AUX)
27 0000  1    POSTCOUNT     : BYTE;          (AUX)
28 0000  1    XMIT_ECG      : BYTE;          (SAMPLER)
29 0000  1  $EXTVAR OFF$
30 0000  1
31 0000  1
32 0000  1  $GLOBVAR ON$
33 0000  1    C_BUFFER                  : ARRAY[0..2] OF BYTE;
34 0003  1    COMMAND_INSIDE            : BOOLEAN;    (Whether we're in the
35 0004  1                                            (process of 2 byte xmit)
36 0004  1    COMMAND_PTR               : BYTE;       (Byte #1 or byte #2?)
37 0005  1
38 0005  1    SPIKE_ENABLED : BOOLEAN;
39 0006  1
40 0006  1    TEMP         : BYTE;
41 0007  1
42 0007  1    (Counters for refractory, etc.)
43 0007  1    SID_OF_TEN   : BYTE; (# of SID true in last ten)
44 0008  1    SID_POINTER  : BYTE; (Pointer into current SID value)
45 0009  1    INDEX        : BYTE; (Working index into SID_LINE)
46 000A  1    SID_LINE     : ARRAY[1..11] OF BYTE; (Sts of SID for last 10 ticks)
47 0015  1    S_REFR_CNT   : BYTE; (10 ms tick counter for spike retrigger)
48 0016  1    A_REFR_SEC   : BYTE; (1 second counter)
49 0017  1    A_REFR_SUB   : BYTE; (10 ms tick counter)
50 0018  1
51 0018  1    (This flag is true when a 2-byte message to Casper needs xmitting)
52 0018  1    PT_ALERT     : BOOLEAN;
53 0019  1
54 0019  1  $GLOBVAR OFF$
55 0019  1
56 0019  1  $EXTVAR ON$
57 0019  1    INTRSTS     : SET OF INTRBITS;
58 0019  1    XECOM_DATA  : BYTE;
59 0019  1    (These are flags that generate special code pairs in the data stream)
60 0019  1    (They are tested before each byte is transmitted. If a code pair is
61 0019  1     currently being transmitted, they are held off)
62 0019  1    SEND_RATE   : BOOLEAN;
63 0019  1    RINGNURSE   : BOOLEAN;
64 0019  1    PTCALLING   : BOOLEAN;
65 0019  1    PTWANTSDT   : BOOLEAN;
66 0019  1    PTREADY     : BOOLEAN;
67 0019  1    PTGAVEUP    : BOOLEAN;
68 0019  1    RATE_TO_SEND : BYTE;    (module MONITOR)
69 0019  1  $EXTVAR OFF$
```

```
70 0000  1
71 0000  1  PROCEDURE RMASK;
72 0000  2    EXTERNAL;
73 0000  1
74 0000  1  PROCEDURE ENABLE_75;  (module SAMPLER)
75 0000  2    EXTERNAL;
76 0000  1
77 0000  1  PROCEDURE SMASK;
78 0000  2    EXTERNAL;
79 0000  1
80 0000  1  $GLOBPROC ON$
81 0000  1
82 0000  1
83 0000  1   PROCEDURE CMDIN(VAL:BYTE);
84 0009  2   BEGIN
85 0009  2     COMMAND_INSIDE := TRUE;
86 000E  2     COMMAND_PTR := 1;
87 0013  2     C_BUFFER[1] := 0FEH;
88 0018  2     C_BUFFER[2] := VAL;
89 001E  2   END;
90 0000  1
91 0000  1  PROCEDURE RESET_REFR;
92 0023  2  BEGIN
93 0023  2     (Impose a 1 second minimum)
94 0023  2     IF (ALARM_REFR = 0) THEN A_REFR_SEC := 0
95 002E  2                             ELSE A_REFR_SEC := ALARM_REFR - 1;
96 0033  2     A_REFR_SUB := 100;
97 0038  2  END;
98 0000  1
99 0000  1  PROCEDURE PROC_SPIKE;
100 0039 2  BEGIN (cont_sid () 1)
101 0039 2    IF SID_OF_TEN > ALARM_TRIP THEN
102 0044 2    BEGIN
103 0044 2      IF (A_REFR_SEC + A_REFR_SUB = 0) THEN
104 0050 2      (Alarm refractory = 0)
105 0050 2      BEGIN
106 0050 2        PT_ALERT := TRUE;
107 0055 2        RESET_REFR;
108 0058 2      END
109 0058 2    END;
110 0058 2  END; (PROC_SPIKE)
111 0000 1
112 0000 1  PROCEDURE LOOK_SPIKE;
113 0059 2  BEGIN
114 0059 2    (This reflects a the first occurance of a spike)
115 0059 2    (once refractory has run out)
116 0059 2    IF (S_REFR_CNT = 0) THEN
117 0061 2      (Here a valid spike has occurred and will not
118 0061 2       occur again for SPIKE_REFR * 10 ms)
119 0061 2      (Note that an enhanced spike will occur at the
120 0061 2       beginning of a patient alert period also.)
121 0061 2      BEGIN
122 0061 2        TEMP := SPIKECODE;
123 0066 2        S_REFR_CNT := SPIKE_REFR;
124 006B 2      END;
125 006B 2    PROC_SPIKE; (Look at potential alarm trip in any case)
126 006E 2  END; (LOOK_SPIKE)
```

```
127 0000  1
128 0000  1   PROCEDURE INBYTE;
129 006F  2   {This procedure is called from SAMPLER every 10 ms with the
130 006F  2    averaged value of the ECG signal for the last 10 ms in the
131 006F  2    variable XMIT_ECG. It is now responsible (it wasn't in the
132 006F  2    first rate detect version) for the testing of the SID line
133 006F  2    for pacing spike occurance. It incorporates code that will
134 006F  2    send a "Patient Alert" message to Casper if the SID is true
135 006F  2    for x sample times (X*10 ms). It will then wait for 500 sample
136 006F  2    times (5 seconds) before sending a patient alert message. Spike
137 006F  2    code transmission is controlled to a refractory also
138 006F  2    -- Beckmann 11 October 1985}
139 006F  2   BEGIN
140 006F  2     {Get the ECG/artifact data byte}
141 006F  2     TEMP := XMIT_ECG;
142 0075  2
143 0075  2     {The decrementing of the alert & spike refractory occurs}
144 0075  2     {whether the spike is present or enabled}
145 0075  2     IF NOT ((A_REFR_SEC + A_REFR_SUB) = 0) THEN
146 008A  2     BEGIN {Decrement the refractory counters}
147 008A  2       IF NOT(A_REFR_SUB = 0) THEN
148 0099  2       BEGIN
149 0099  2         A_REFR_SUB := A_REFR_SUB - 1;
150 00A1  2       END
151 00A4  2       ELSE
152 00A4  2       BEGIN
153 00A4  2         IF NOT(A_REFR_SEC = 0) THEN
154 00B5  2         BEGIN
155 00B5  2           A_REFR_SUB := 100;
156 00BA  2           A_REFR_SEC := A_REFR_SEC - 1;
157 00C2  2         END
158 00C2  2       END
159 00C2  2     END;
160 00C2  2     IF NOT(S_REFR_CNT = 0) THEN S_REFR_CNT := S_REFR_CNT - 1;
161 00DB  2
162 00DB  2     {Here the spike channel on the SID line is looked at if enabled}
163 00DB  2     {CONT_SID_COUNT reflects the # of continuous SID line occurances}
164 00DB  2     RMASK;
165 00DE  2     IF SID_POINTER = 10 THEN SID_POINTER := 1
166 00EE  2                          ELSE SID_POINTER := SID_POINTER + 1;
167 00F6  2     IF (SID IN INTRSTS) THEN SID_LINE[SID_POINTER] := 1
168 0111  2                          ELSE SID_LINE[SID_POINTER] := 0;
169 011D  2     SID_OF_TEN := 0;
170 0122  2     INDEX := 1;
171 0127  2     WHILE NOT(INDEX = 11) DO
172 0138  2     BEGIN
173 0138  2       SID_OF_TEN := SID_OF_TEN + SID_LINE[INDEX];
174 0149  2       INDEX := INDEX + 1;
175 0151  2     END;
176 0154  2
177 0154  2
178 0154  2     IF SPIKE_ENABLED THEN
179 015B  2     BEGIN
180 015B  2       IF (SID_LINE[SID_POINTER] = 1) THEN LOOK_SPIKE
181 016E  2     END
182 0171  2     ELSE {spike not enabled}
```

```
183 0171 2    BEGIN
184 0171 2    {Here the spike enhancement is software-disabled. We      }
185 0171 2    {set the refractories to zero so that 1st patient alert & spike }
186 0171 2    {are recognized. Once enhancement is enabled, refractory is }
187 0171 2    {decremented in the outer loop.                           }
188 0171 2      A_REFR_SEC := 0;
189 0176 2      A_REFR_SUB := 0;
190 017B 2      S_REFR_CNT := 0;
191 0180 2    END;
192 0180 2
193 0180 2    {Test for calibration signal generator activity}
194 0180 2    {Calibration overrides the transmission of EKG data or
195 0180 2     the spike detection code. It does not override the
196 0180 2     transmission of special codes tested for below.}
197 0180 2    IF NOT(CALGENCOUNT = 0)
198 0191 2      THEN BEGIN
199 0191 2        IF (CALGENCOUNT > (STEPCOUNT + POSTCOUNT))
200 01A4 2          THEN TEMP := PRECALVAL
201 01AD 2          ELSE IF (CALGENCOUNT > POSTCOUNT)
202 01BA 2            THEN TEMP := STEPCALVAL
203 01C3 2            ELSE TEMP := POSTCALVAL;
204 01C9 2        CALGENCOUNT := CALGENCOUNT - 1;
205 01D1 2      END;
206 01D1 2
207 01D1 2
208 01D1 2    {Here flags are tested for special codes to be sent to Casper.}
209 01D1 2    {Their order implies their rank and precedence. Notice that only
210 01D1 2     if they are sent are they reset.}
211 01D1 2    {COMMANDS_INSIDE indicates that a pair is in the process of being
212 01D1 2     sent and blocks the testing for any other flags}
213 01D1 2
214 01D1 2    IF COMMAND_INSIDE THEN BEGIN END ELSE
215 01DB 2
216 01DE 2    {Test Alert (should be a 07H) with 01H (ring bell)}
217 01DB 2    IF PT_ALERT  THEN BEGIN CMDIN(01H); PT_ALERT  := FALSE
218 01EC 2                     END ELSE
219 01EF 2    IF PTCALLING THEN BEGIN CMDIN(02H); PTCALLING := FALSE
220 0200 2                     END ELSE
221 0203 2    IF RINGNURSE THEN BEGIN CMDIN(01H); RINGNURSE := FALSE
222 0214 2                     END ELSE
223 0217 2    IF SEND_RATE THEN BEGIN
224 021E 2                    {40 (= RATE_TO_SEND (= 255 better be!!)
225 021E 2                    {38 & 39 used for special SAM cases}
226 021E 2                    {We'll use 37 here for a CLOCKIO trap}
227 021E 2                    {I'd test it here but I don't think there's time}
228 021E 2                    {Oh, hell....}
229 021E 2                    IF (RATE_TO_SEND < 37) THEN RATE_TO_SEND := 37;
230 022D 2                    CMDIN(RATE_TO_SEND);
231 0232 2                    SEND_RATE := FALSE;
232 0237 2                  END ELSE
233 023A 2    IF PTWANTSDT THEN BEGIN CMDIN(03H); PTWANTSDT := FALSE
234 024B 2                     END ELSE
235 024E 2    IF PTREADY   THEN BEGIN CMDIN(05H); PTREADY   := FALSE
236 025F 2                     END ELSE
237 0262 2    IF PTGAVEUP  THEN BEGIN CMDIN(06H); PTGAVEUP  := FALSE
238 0273 2                     END;
239 0273 2
```

```
240 0273  2
241 0273  2      (********************)
242 0273  2      (HERE WE OUTPUT A BYTE)
243 0273  2      (********************)
244 0273  2      IF COMMAND_INSIDE
245 027A  2        THEN BEGIN
246 027A  2          XECOM_DATA := C_BUFFER[COMMAND_PTR];
247 0288  2          COMMAND_PTR := COMMAND_PTR + 1;
248 0290  2          IF COMMAND_PTR = 3
249 0295  2            THEN COMMAND_INSIDE := FALSE;
250 029A  2        END
251 029D  2      (Temp contains either a SPIKE code or EKG data)
252 029D  2      ELSE XECOM_DATA := TEMP;
253 02A3  2
254 02A3  2  END;
255 0000  1
256 0000  1
257 0000  1  PROCEDURE INIT_QUEUE;
258 02A9  2  BEGIN
259 02A9  2    COMMAND_INSIDE := FALSE;
260 02AE  2    S_REFR_CNT := 0;
261 02B3  2
262 02B3  2    INDEX := 1;
263 02B8  2    WHILE NOT(INDEX = 11) DO
264 02C9  2    BEGIN
265 02C9  2      SID_LINE[INDEX] := 0;
266 02D5  2      INDEX := INDEX + 1;
267 02DA  2    END;
268 02DD  2
269 02DD  2    SID_POINTER := 1;
270 02E2  2    SID_OF_TEN := 0;
271 02E7  2    COMMAND_PTR := 0;
272 02EC  2    A_REFR_SEC := 0;
273 02F1  2    A_REFR_SUB := 0;
274 02F6  2
275 02F6  2    (Reset the flags here)
276 02F6  2    SEND_RATE   := FALSE;
277 02FB  2    RINGNURSE   := FALSE;
278 0300  2    PTCALLING   := FALSE;
279 0305  2    PTWANTSDT   := FALSE;
280 030A  2    PTREADY     := FALSE;
281 030F  2    PTGAVEUP    := FALSE;
282 0314  2    PT_ALERT    := FALSE;
283 0319  2    ENABLE_75;
284 031C  2  END;
285 0000  1  $GLOBPROC OFF$
286 0000  1  .

End of compilation, number of errors=     0

FILE: TELE3:BOBBS1      HP 64000 - Pascal     "8085" Code Generator 1 0000  1  "8085"
  2 0000  1  $TITLE "MIAMI BASESTATION PROGRAM -- TELEPHONE"$
  3 0000  1  PROGRAM TELEPHONE;
  4 0000  1
  5 0000  1  $OPTIMIZE OFF$
```

```
 6 0000  1  $EXTENSIONS ON$
 7 0000  1  $SEPARATE ON$
 8 0000  1
 9 0000  1  CONST
10 0000  1    CASPERSNUM    = 0;
11 0000  1    ALT1NUM       = 1;
12 0000  1    ALT2NUM       = 2;
13 0000  1
14 0000  1    SPIKECODE     = 0FEH;         (DATA STREAM CODE FOR SPIKEDETECT)
15 0000  1
16 0000  1  TYPE
17 0000  1    XESTS_BITS    = (XETXRDY,XERXRDY,XETXE,XEPE,XEOE,XEFE,XEDET,XEDSR);
18 0000  1    XECMD_BITS    = (XETXEN,XEDTR,XERXEN,XEBRK,XEER,XERTS,XEIR,XEEH);
19 0000  1    XESTS_TYPE    = SET OF XESTS_BITS;
20 0000  1    XECMD_TYPE    = SET OF XECMD_BITS;
21 0000  1    BITTYPE       = (D0,D1,D2,D3,D4,D5,D6,D7);
22 0000  1    S8            = SET OF BITTYPE;
23 0000  1    STATE_TYPE    = (STATE_A, STATE_B, STATE_C, STATE_D);
24 0000  1    LSTATE_TYPE   = (BUSY,RINGBACK,VOICE,DIALTONE,TIMEOUT);
25 0000  1    CHAN_TYPE     = (CHAN_A,CHAN_B);
26 0000  1    MODE_TYPE     = (MODE_A,MODE_B,MODE_AB);
27 0000  1    BYTEPTR       = ^BYTE;
28 0000  1    PHONENUM      = ARRAY[0..19] OF CHAR;
29 0000  1    PHONETAB      = ARRAY[0..9] OF PHONENUM;
30 0000  1
31 0000  1  $PAGE$
32 0000  1  VAR
33 0000  1
34 0000  1  $EXTVAR ON$
35 0000  1    PHONEBOOK           : PHONETAB;
36 0000  1
37 0000  1    PORT_A              : S8;
38 0000  1    PORT_B              : S8;
39 0000  1    PORT_C              : S8;
40 0000  1    XECOM_DATA          : BYTE;
41 0000  1    XECOM_COMMAND       : S8;
42 0000  1    A_AMP               : BYTE;
43 0000  1    B_AMP               : BYTE;
44 0000  1    SECONDS_LEFT        : BYTE;
45 0000  1    COMMAND_RCVD        : BYTE;
46 0000  1    RINGMURSE           : BOOLEAN;
47 0000  1
48 0000  1  $EXTVAR OFF$
49 0000  1  $GLOBVAR ON$
50 0000  1
51 0000  1  VAR
52 0000  1    LAST_RING                : BOOLEAN;
53 0001  1    RING_STATE               : BOOLEAN;
54 0002  1    STS_WORK                 : XESTS_TYPE;
55 0003  1    PHYSCONNECTED,
56 0003  1    PHYSCONNECTFAIL,
57 0003  1    MODEMCONNECTED,
58 0003  1    MODEMCONNECTFAIL         : BOOLEAN;
59 0007  1    RING_COUNT               : BYTE;
60 0008  1    CONNECT_RESULT           : BYTE;
61 0009  1    DUMMY                    : BYTE;
62 000A  1
```

```
63 000A  1  {This should reflect the last values written to the command reg.}
64 000A  1  XE_CMD          : XECMD_TYPE;
65 000B  1
66 000B  1  {This is a new layout for the status register}
67 000B  1  {Its origin follows XECUM_COMMAND (They're the same location)}
68 000B  1  {Move this to MIAMIO when things settle down.}
69 000B  1  $ORG 0F60H$
70 000B  1  XE_STS          : XESTS_TYPE;
71 000B  1  $END_ORG$
72 000B  1
73 000B  1  INFO_FLAG, DATA_FLAG,
74 000B  1  TX_FLAG         : BOOLEAN;
75 000E  1
76 000E  1  DBYTE, IBYTE    : BYTE;
77 0010  1
78 0010  1  {The following are used for function manipulation}
79 0010  1    SLOWDIAL      : BOOLEAN;    {IF TRUE, DIAL TT OR PULSE W/ PAUSE}
80 0011  1    USE_TT        : BOOLEAN;    {IF TRUE, TRY TT FIRST TO DIAL CASPER}
81 0012  1  {}
82 0012  1    PRICHAN,
83 0012  1    SECCHAN       : BYTEPTR;    {POINTERS TO PRIMARY & SECONDARY EKG}
84 0016  1  {}
85 0016  1    FILTERA,
86 0016  1    FILTERB       : BOOLEAN;    {WHETHER TO FILTER A AND B}
87 0018  1    A_GAIN,
88 0018  1    B_GAIN        : 0..15;
89 001A  1    ALRIGHT       : BOOLEAN;
90 001B  1  {}
91 001B  1    CASPER_ANSWERED             : BOOLEAN;
92 001C  1    RINGS         : 0..10;
93 001D  1    VCOUNT        : 0..10;
94 001E  1
95 001E  1  {}
96 001E  1    RESULT : BYTE; {THIS IS THE RESULT OF ALL SENDFUNC CALLS}
97 001F  1
98 001F  1  $PAGE$
99  0000 1  PROCEDURE SETCLOCK(NUM:BYTE);   EXTERNAL;    {XETSM -- starts the 1 second interrupt}
100 0000 1  PROCEDURE STOPCLOCK;            EXTERNAL;    {XETSM -- disables clock interrupts}
101 0000 1  $GLOBPROC ON$
102 0000 1
103 0000 1  {-----------------------------------------------------------}
104 0000 1  {********** MODEM/TELEPHONE FUNCTIONS AND PROCEDURES **********}
105 0000 1  {-----------------------------------------------------------}
106 0000 1  {-----}
107 0000 1  FUNCTION ELITEONHOOK         : BOOLEAN;
108 0001 2  VAR
109 0001 2    I : INTEGER;
110 0000 2  BEGIN
111 0000 2    {MUST HAVE POWER TO SENSE OFFHOOK}
112 0000 2    {This de-energizes the ringer relay. This puts the Elite either}
113 0000 2    {across the +5 of the pseudoringer or across the line}
114 0000 2    IF ((PORT_B * [D0] = [D0])) THEN ELITEONHOOK := TRUE ELSE
115 0012 2    ELITEONHOOK := FALSE;
116 0017 2  END;
117 0000 1
118 0000 1  {-----}
119 0000 1  FUNCTION ELITEOFFHOOK        : BOOLEAN;
```

```
120 0001  2  VAR
121 0001  2    I: INTEGER;
122 001C  2  BEGIN
123 001C  2    (MUST HAVE POWER TO SENSE OFFHOOK)
124 001C  2    ELITEOFFHOOK := TRUE;
125 0021  2    FOR I := 0 TO 10000 DO BEGIN
126 0034  2      (Port bit D0 HI indicates ONHOOK)
127 0034  2      IF ((PORT_B * [D0] = [D0])) THEN BEGIN
128 003E  2                                 ELITEOFFHOOK := FALSE;
129 0043  2                                 I := 10000;
130 0049  2                                 END;
131 0049  2    END;
132 005B  2  END;
133 0000  1
134 0000  1  {------}
135 0000  1  PROCEDURE ELITEONLINE;
136 0060  2  (THIS PROCEDURE PUTS THE ELITE RELAY IN THE ONLINE POSITION)
137 0060  2  BEGIN
138 0060  2    PORT_A := PORT_A * [D7,D5,D4,D3,D2,D1,D0] (D6 --> ZERO)
139 0068  2  END;
140 0000  1
141 0000  1  PROCEDURE ELITEOFFLINE;
142 0069  2  (THIS PROCEDURE PUTS THE ELITE RELAY IN THE OFFLINE POSITION)
143 0069  2  BEGIN
144 0069  2    PORT_A := PORT_A + [D6]; (D6 --> ONE)
145 0071  2  END;
146 0000  1
147 0000  1  {------}
148 0000  1  PROCEDURE XECOM_INIT;    (CHANGED 3-4-86)
149 0001  2  VAR
150 0000  2    IDX : INTEGER;
151 0072  2  BEGIN
152 0072  2
153 0072  2    (These bytes either supply two missing sync bytes or
154 0072  2                           one missing sync and a mode
155 0072  2                           or two modes)
156 0072  2    (The values are selected without the D6 internal reset bit
157 0072  2     high and as 1.5 stop bit 1200 baud async which doesn't
158 0072  2     require any sync bytes on its own)
159 0072  2    (Be careful if you decide to change these -- if this procedure
160 0072  2     is entered upon hardware reset, the XeCom will be looking for
161 0072  2     a mode byte. If you change these following two bytes to zeros
162 0072  2     as recommended in the application note, the unit MAY look for
163 0072  2     two SYNC bytes. This means that the second zero and the reset
164 0072  2     byte could be loaded as SYNC bytes which would force the
165 0072  2     desired mode byte to be interpreted as a command -- VERY BAD!)
166 0072  2
167 0072  2    (Hard reset first -- modification done to board tying D5 of PORT_C )
168 0072  2    (to RESET of the XeCOM.)
169 0072  2  $LIST_CODE ON$ 170 0072  2    PORT_C := PORT_C + [D5];
          0072 3A ????      LDA  PORT_C
          0075 F6 20        ORI  32
          0077 32 ????      STA  PORT_C
```

```
171 007A  2   FOR IDX := 1 TO 1000 DO BEGIN END;
      007A  21 E803       LXI   H,1000
      007D  22 ????       SHLD  DXECOM_INIT+2
      0080  11 0100       LXI   D,1
      0083  CD ????       CALL  Zintleq
      0086  CA ????       JZ    XECOM_I07_6
      0089  EB            XCHG
      008A              XECOM_I07_7:
      008A  22 ????       SHLD  DXECOM_INIT
      008D  EB            XCHG
      008E  2A ????       LHLD  DXECOM_INIT+2
      0091  CD ????       CALL  Zintneq
      0094  CA ????       JZ    XECOM_I07_6
      0097  EB            XCHG
      0098  23            INX   H
      0099  C3 ????       JMP   XECOM_I07_7
      009C              XECOM_I07_6:

172 009C  2   PORT_C := PORT_C - [D5];
      009C  3A ????       LDA   PORT_C
      009F  47            MOV   B,A
      00A0  EE 20         XRI   32
      00A2  A0            ANA   B
      00A3  32 ????       STA   PORT_C 173 00A6  2
174 00A6  2   XECOM_COMMAND := [D6,D3,D2,D0];
      00A6  3E 4D         MVI   A,77
      00A8  32 ????       STA   XECOM_COMMAND 175 00AB  2   (1 STOP BIT, 8 BITS/CHAR, PARITY DISABLED, 1200 BAUD ASYNC)
176 00AB  2
177 00AB  2   (Reset Errors -- parity, overrun, framing)
178 00AB  2   XECOM_COMMAND := [D0,D1,D2,D4,D5];
      00AB  3E 37         MVI   A,55
      00AD  32 ????       STA   XECOM_COMMAND 179 00B0  2
180 00B0  2
181 00B0  2  END;
      00B0              RXECOM_INIT:
      00B0  C9            RET
      0008              DATA
      0008              DXECOM_INIT:
      0008              DS    4
      00B1              PROG
                        EXECOM_INIT EQU $-1

182 0000  1  $LIST_CODE OFF$
183 0000  1  $PAGE$
184 0000  1
185 0000  1  {-----}
186 0000  1  PROCEDURE SENDFUNC ( FUNCBYTE:CHAR ; VAR RESULT:CHAR ) ;
187 00BA  2  BEGIN
188 00BA  2   (SEND THE COMMAND BYTE WITH RTS CLEARED)
189 00BA  2   (HERE COMES THE FUNCTION)
190 00BA  2   XECOM_COMMAND := [D4,D2,D1,D0];
191 00BF  2   (READY FOR THE FUNCTION?)
```

```
192 00BF  2     WHILE (XECOM_COMMAND * [D0] = []) DO ;
193 00CC  2     XECOM_DATA := FUNCBYTE;
194 00D2  2     (THEN WAIT UNTIL TXRDY GO HIGH)
195 00D2  2     WHILE (XECOM_COMMAND * [D0] = []) DO;
196 00DF  2     (THEN CHECK FOR RXRDY HI AND DSR LO FOR INFO BYTE)
197 00DF  2     IF (XECOM_COMMAND * [D7,D1] = [D1]) THEN
198 00E9  2       RESULT := XECOM_DATA
199 00F3  2     ELSE RESULT := ' ';
200 00F8  2     (IF NO INFO BYTE, RETURN " ")
201 00F8  2   END;
202 0000  1   $PAGE$
203 0000  1
204 0000  1   (The following procedures are updates of the sendfunc-type)
205 0000  1   (function. Their purpose is to interface to the XeCom modem)
206 0000  1   (in everything but mainstream data transfers.)
207 0000  1
208 0000  1   (-----)
209 0000  1   PROCEDURE XECOM_DO(FUNC:BYTE; VAR OK:BOOLEAN);
210 0003  2
211 0003  2   (This procedure writes a function byte out to the XeCom)
212 0003  2   (It signals the modem that a function byte is to be written)
213 0003  2   (by clearing the RTS (request to send) bit in the command)
214 0003  2   (register. It then looks to see if the modem is ready to)
215 0003  2   (receive a new function. If it isn't, it sets OK to false)
216 0003  2
217 0003  2   VAR
218 0003  2     (Used to snapshot the status of the modem)
219 0003  2     STS_WORK : XESTS_TYPE;
220 0108  2
221 0108  2   BEGIN
222 0108  2     (Turn off RTS)
223 0108  2     XE_CMD := XE_CMD - [XERTS];
224 0112  2     XE_CMD := [XERXEN,XETXEN,XEDTR,XEER];
225 0117  2     XECOM_COMMAND := SB(XE_CMD);
226 011A  2
227 011A  2     (Snapshot)
228 011A  2     STS_WORK := XE_STS;
229 0120  2
230 0120  2     IF NOT (XETXRDY IN STS_WORK) THEN
231 012A  2       OK := FALSE
232 0131  2     ELSE BEGIN
233 0131  2       OK := TRUE;
234 0136  2       XECOM_DATA := FUNC;
235 013C  2     END; (IF)
236 013C  2
237 013C  2   END;
238 0000  1
239 0000  1   (-----)
240 0000  1   PROCEDURE GETDATA(VAR GOT_INFO  : BOOLEAN; VAR GOT_DATA:BOOLEAN;
241 0004  2                     VAR TX_RDY    : BOOLEAN;
242 0006  2                     VAR INFO_BYTE : BYTE;   VAR DATA_BYTE : BYTE);
243 014C  2
244 014C  2   (Layout of bits for command and status)
245 014C  2   (XESTS_BITS  = (XETXRDY,XERXRDY,XETXE,XEPE,XEOE,XEFE,XEDET,XEDSR);)
246 014C  2   (XECMD_BITS  = (XETXE,XEDTR,XERXE,XEBRK,XEER,XERTS,XEIR,XELH);     )
247 014C  2
248 014C  2   (This procedure gets information from the XeCom. It can return nothing,
```

```
 014C  2    a data byte, an information byte, or both.  The reason we have to be
 014C  2    concerned here about a data byte when the primary use of this routine
 014C  2    is to get information from the modem regarding a previous command, is
 014C  2    that a data byte in the buffer will block the presentation of an info
 014C  2    byte by the modem.  We therefore look for a data byte also.)
 014C  2    (The routine will return CANT as an aid if no byte is returned and a
 014C  2    function in still processing (or transmitter busy??))
 014C  2
 014C  2    (Note that all five parameters of this function are variables and
 014C  2    need to be declared as such in uses of this procedure.)
 014C  2
 014C  2
 014C  2    BEGIN
 014C  2      STS_WORK := XE_STS;                        (Snapshot)
 0152  2      (Initialize)
 0152  2      GOT_INFO := FALSE;
 0157  2      GOT_DATA := FALSE;
 015C  2      TX_RDY := FALSE;
 0161  2
 0161  2      (First, is there data available?)
 0161  2      IF (XERXRDY IN STS_WORK) THEN BEGIN
 016A  2        (First we consider the case with a pending data byte)
 016A  2        IF (XEDSR IN STS_WORK) THEN BEGIN
 0172  2          (If there is data, get it)
 0172  2          DATA_BYTE := XECUM_DATA;
 0179  2          GOT_DATA := TRUE;
 017E  2          (Take another snapshot!)
 017E  2          STS_WORK := XE_STS;
 0184  2          (This is necessary to see if an info byte is waiting)
 0184  2
 0184  2          (Now look to see if there is an information byte)
 0184  2          IF ((XERXRDY IN STS_WORK) AND (NOT(XEDSR IN STS_WORK))) THEN BEGIN
 0196  2            INFO_BYTE := XECUM_DATA;
 019D  2            GOT_INFO := TRUE;
 01A2  2          END; (IF)
 01A2  2
 01A2  2        END ELSE BEGIN (Here we know it's just an info byte)
 01A5  2          INFO_BYTE := XECUM_DATA;
 01AC  2          GOT_INFO := TRUE;
 01B1  2        END;
 01B1  2
 01B1  2      END;
 01B1  2      IF NOT (XETXRDY IN STS_WORK) THEN TX_RDY := FALSE;
 01C2  2    END;
 0000  1
 0000  1
 0000  1    (-----)
 0000  1    PROCEDURE ABORT_FUNCTION;
 01CF  2    (All that's required here is a raising of the Request to Send
 01CF  2    line on the modem.  The GETDATA function should be executed
 01CF  2    after this to clear the 'A' info byte that is generated if
 01CF  2    a function is actually aborted.)
 01CF  2    BEGIN
 01CF  2      XE_CMD := XE_CMD + [XERTS];
 01D7  2      XECUM_COMMAND := SB(XE_CMD);
 01DA  2    END;
 0000  1
 0000  1    $PAGE$
```

```
307 0000  1  {-----}
308 0000  1  PROCEDURE LOOK_FOR_COMMAND;
309 01DB  2  {Here we assume 0AAH is unused}
310 01DB  2  BEGIN
311 01DB  2    GETDATA(INFO_FLAG,DATA_FLAG,TX_FLAG,IBYTE,DBYTE);
312 01E8  2    IF DATA_FLAG THEN COMMAND_RCVD := DBYTE
313 01FB  2                 ELSE COMMAND_RCVD := 0AAH;
314 01FD  2  END;
315 0000  1
316 0000  1
317 0000  1
318 0000  1  {-----}
319 0000  1  PROCEDURE DIALFROMPHONEBOOK(ENTRY:BYTE);
320 0001  2  (Note that this checks SLOWDIAL and places delays into dialing)
321 0001  2  (stream if true)
322 0001  2  (Note also that this is adaptive dialing, i.e., try first digit)
323 0001  2  (TT and if within 5 seconds the dialtone doesn't go away, go to)
324 0001  2  (pulse dialing.)
325 0001  2
326 0001  2  VAR
327 0001  2    I,J,K : INTEGER;
328 0007  2    CH    : CHAR;
329 0207  2  BEGIN
330 0207  2
331 0207  2    (First, make sure HostReady (DTR) and ErrorReset are set
332 0207  2     and that RTS is low, indicating function write)
333 0207  2    XE_CMD := (XE_CMD + [XEER,XEDTR])-[XERTS];
334 0213  2    XECOM_COMMAND := S8(XE_CMD);
335 0216  2    (Get the Elite offline because it causes false readings)
336 0216  2    ELITEOFFLINE;
337 0219  2    (Wait for the dialtone)
338 0219  2    REPEAT XECOM_DO('W',ALRIGHT) UNTIL ALRIGHT;
339 0227  2    (Remember that alright indicates that the function could be
340 0227  2     written. It doesn't say anything about the InfoByte.)
341 0227  2
342 0227  2    (Dial the first digit)
343 0227  2    CH := PHONEBOOK[ENTRY,0];
344 023F  2    XECOM_DO(CH,ALRIGHT);
345 0246  2
346 0246  2    (If we still have dialtone then we have to go to rotary)
347 0246  2    REPEAT XECOM_DO('W', ALRIGHT) UNTIL ALRIGHT;
348 0254  2    REPEAT
349 0254  2      GETDATA(INFO_FLAG,DATA_FLAG,TX_FLAG,IBYTE,DBYTE)
350 0261  2    UNTIL TX_FLAG;
351 0268  2    (If no information byte, dialtone still there & switch to rotary)
352 0268  2    IF NOT INFO_FLAG THEN BEGIN
353 026F  2      (Command to switch to rotary dial)
354 026F  2      REPEAT XECOM_DO('R',ALRIGHT) UNTIL ALRIGHT;
355 027D  2      I := 0;
356 0283  2    END ELSE
357 0286  2      I := 1;
358 028C  2
359 028C  2    (It's ok for them to listen to dialing)
360 028C  2    ELITEONLINE;
361 028F  2
362 028F  2    WHILE PHONEBOOK[ENTRY,I] () ' ' DO BEGIN
363 02A9  2      XECOM_DO(PHONEBOOK[ENTRY,I],ALRIGHT);
```

```
364 02C9 2      IF SLOWDIAL THEN FOR J := 1 TO 2000 DO ;
365 02F2 2      I := I + 1;
366 02FC 2    END; (WHILE)
367 02FF 2
368 02FF 2    (SHOULD CHECK AFTER THIS TO SEE IF RINGING)
369 02FF 2    (IF NOT, SHOULD HANGUP AND SET SLOWDIAL TO TRUE)
370 02FF 2    (AND TRY AGAIN)
371 02FF 2  END;
372 0000 1
373 0000 1  (-----)
374 0000 1  PROCEDURE HANGUPLINE;
375 0308 2  BEGIN
376 0308 2    (XECOM ONHOOK)
377 0308 2    XECOM_COMMAND := [];
378 030D 2    (ELITE OFFLINE)
379 030D 2    PORT_A := PORT_A + [D6];
380 0315 2  END;
381 0000 1
382 0000 1  (-----)
383 0000 1  PROCEDURE XECOM_TO_DTMF;
384 0316 2  BEGIN
385 0316 2  ( DUMMY:=XECOM_DATA; DUMMY:=XECOM_DATA; DUMMY:=XECOM_DATA;     )
386 0316 2    REPEAT XECOM_DO('D',ALRIGHT) UNTIL ALRIGHT;
387 0324 2    (NOW EVERY TIME THE RXRDY GOES HIGH, A DTMF HAS BEEN RECEIVED)
388 0324 2  END;
389 0000 1
390 0000 1  (-----)
391 0000 1  PROCEDURE TRANSPOND;
392 0326 2    (THIS PROCEDURE SENDS A DTMF TONEPAIR AND EXPECTS ONE BACK)
393 0326 2    (OF THE SAME VALUE WITHIN A CERTAIN AMOUNT OF TIME (5 SEC.))
394 0326 2    (ITS PURPOSE IS TO CONFIRM THAT CASPER IS ON THE OTHER END OF A)
395 0326 2    (QUIET LINE. IF IT DOES, THE VARIABLE 'CASPER_ANSWERED' IS)
396 0326 2    (SET TO TRUE)
397 0326 2    (THIS PROCEDURE SENDS A DTMF 'A' IF THE NO DATA PRIORITY AND 'B')
398 0326 2    (FOR A DATA PRIORITY CONNECT)
399 0326 2  BEGIN
400 0326 2    SENDFUNC('a',RESULT); (SEND ONLY A FOR NOW)
401 032D 2    XECOM_TO_DTMF;
402 0330 2    ( WAIT_FOR_SECONDS(5); )
403 0330 2    IF ((XECOM_COMMAND * [D1]) = []) THEN CASPER_ANSWERED := FALSE
404 0342 2    ELSE BEGIN
405 0342 2      IF XECOM_DATA = '*' THEN CASPER_ANSWERED := TRUE (FOR TEST)
406 0352 2      ELSE CASPER_ANSWERED := FALSE;
407 0357 2    END;
408 0357 2  END;
409 0000 1
410 0000 1  $PAGE$
411 0000 1
412 0000 1  FUNCTION GOTODATA           : BOOLEAN;
413 0359 2    (This is only active with the modems squelched)
414 0359 2  BEGIN
415 0359 2    XECOM_COMMAND:=[D2,D1,D0]; (enables receiver)
416 035E 2    GETDATA(INFO_FLAG, DATA_FLAG,TX_FLAG,IBYTE,DBYTE);
417 036B 2    ( IF (D1 IN XECOM_COMMAND) THEN DBYTE := XECOM_DATA ELSE DBYTE := ' ';)
418 036B 2    IF DATA_FLAG THEN
419 0372 2      IF ((DBYTE = 'a') OR (DBYTE = '*')) THEN
420 0394 2        GOTODATA := TRUE
```

```
421 039C  2      ELSE
422 039C  2         GOTODATA := FALSE
423 03A4  2      ELSE GOTODATA := FALSE;
424 03A9  2    END;
425 0000  1
426 0000  1  FUNCTION BEING_CALLED: BOOLEAN;
427 0001  2  VAR
428 0001  2    B_C : BOOLEAN;
429 03AE  2  BEGIN
430 03AE  2    B_C := TRUE;
431 03B3  2    IF (PORT_B * [D2] = []) THEN   B_C := FALSE;
432 03C2  2    BEING_CALLED := B_C;
433 03C8  2  END;
434 0000  1
435 0000  1  PROCEDURE ENABLE_XECOM;
436 03CA  2  BEGIN
437 03CA  2    XE_CMD := XE_CMD + [XECTR];
438 03D2  2    XECOM_COMMAND := SB(XE_CMD);
439 03D5  2  END;
440 0000  1
441 0000  1  PROCEDURE DISABLE_XECOM;
442 03D6  2  BEGIN
443 03D6  2    XE_CMD := XE_CMD - [XECTR];
444 03E0  2    XECOM_COMMAND := SB(XE_CMD);
445 03E3  2  END;
446 0000  1
447 0000  1  PROCEDURE ENABLE_TXRX;
448 03E4  2  BEGIN
449 03E4  2    XE_CMD := XE_CMD + [XERXEN,XETXEN];
450 03EC  2    XECOM_COMMAND := SB(XE_CMD);
451 03EF  2  END;
452 0000  1
453 0000  1  PROCEDURE DISABLE_TXRX;
454 03F0  2  BEGIN
455 03F0  2    XE_CMD := XE_CMD - [XERXEN,XETXEN];
456 03FA  2    XECOM_COMMAND := SB(XE_CMD);
457 03FD  2  END;
458 0000  1
459 0000  1  PROCEDURE XECOM_TO_DATA;
460 03FE  2  BEGIN
461 03FE  2    (RTS Hi, Error reset, Receive Enable, DTR, Transmit Enable)
462 03FE  2    (RTS indicates all further XECOM_DATA writes will be data
463 03FE  2     to be transmitted.)
464 03FE  2    ( XECOM_COMMAND := [D5,D4,D2,D1,D0];  ) (Done elsewhere)
465 03FE  2  END;
466 0000  1
467 0000  1  PROCEDURE STARTRINGBACK;
468 03FF  2  BEGIN
469 03FF  2    RING_STATE := TRUE;
470 0404  2    RINGNURSE := TRUE;
471 0409  2    SETCLOCK(1);
472 040E  2    PORT_A := PORT_A + [D6,D2]; (Energize the Eliterelay & gate pseudo gn)
473 0416  2  END;
474 0000  1  PROCEDURE STOPRINGBACK;
475 0418  2  BEGIN
476 0418  2    RING_STATE := FALSE;
477 041D  2    STOPCLOCK;
```

```
478 0420 2      (Turn off gen here)
479 0420 2      (De-energize ringer relay)
480 0420 2      PORT_A := PORT_A * [D6,D1,D0]; (Leave the Eliterelay & lites alone)
481 0428 2   END;
482 0000 1   PROCEDURE SERVICERINGBACK;
483 0429 2   BEGIN
484 0429 2      IF (SECONDS_LEFT = 0) THEN
485 0431 2        IF RING_STATE THEN BEGIN
486 0438 2           RING_STATE := FALSE;
487 043D 2           SETCLOCK(3);
488 0442 2           (Turn off gen)
489 0442 2           (De-energize ringer relay)
490 0442 2           PORT_A := PORT_A * [D6,D1,D0]; (Leave the Eliterelay & lites alone)
491 044A 2        END ELSE BEGIN
492 044D 2           RING_STATE := TRUE;
493 0452 2           SETCLOCK(1);
494 0457 2           RINGNURSE := TRUE;           (Serviced and reset by ISR)
495 045C 2           (Do the relay switching and generator start here)
496 045C 2           PORT_A := PORT_A + [D6,D2]; (Energize the Eliterelay & gate pseudo gn)
497 0464 2        END;
498 0464 2   END;
499 0000 1
500 0000 1   PROCEDURE STARTBELL;
501 0000 2   VAR
502 0000 2      I: INTEGER;
503 0467 2   BEGIN
504 0467 2      (The first call to SERVICEBELL will turn the bell on)
505 0467 2      RING_STATE := TRUE;
506 046C 2      SETCLOCK(1);
507 0471 2      PORT_A := PORT_A + [D7,D6,D3]; (Energize the Eliterelay & gate BELL gn)
508 0479 2   END;
509 0000 1   PROCEDURE STOPBELL;
510 047B 2   BEGIN
511 047B 2      (Do not call SERVICEBELL after this)
512 047B 2      RING_STATE := FALSE;
513 0480 2      STOPCLOCK;
514 0483 2      (Turn off gen here)
515 0483 2      (De-energize ringer relay)
516 0483 2      PORT_A := PORT_A * [D6,D1,D0]; (Leave the Eliterelay & lites alone)
517 048B 2   END;
518 0000 1   PROCEDURE SERVICEBELL;
519 048C 2   BEGIN
520 048C 2      IF (SECONDS_LEFT = 0) THEN
521 0494 2        CASE RING_STATE OF
522 049A 2          TRUE: BEGIN
523 049A 2             RING_STATE := FALSE;
524 049F 2             SETCLOCK(3);
525 04A4 2             (Turn off gen)
526 04A4 2             (De-energize ringer relay)
527 04A4 2             PORT_A := PORT_A * [D6,D1,D0]; (Leave the Eliterelay & lites alone)
528 04AC 2          END;
529 04AF 2          FALSE: BEGIN
530 04AF 2             RING_STATE := TRUE;
531 04B4 2             SETCLOCK(1);
532 04B9 2             RINGNURSE := TRUE;           (Serviced and reset by ISR)
533 04BE 2             (Do the relay switching and generator start here)
534 04BE 2             PORT_A := PORT_A + [D7,D6,D3]; (Energize the Eliterelay & gate BELL gn)
```

```
535 14C6  2     END;
536 14C9  2     END; (CASE)
537 14D6  2   END;
538 0000  1
539 0000  1 PROCEDURE PHYSCHECK;
540 04D9  2 BEGIN
541 04D9  2   (CHECK THE PHYSICAL CONNECTION)
542 04D9  2   PHYSCONNECTED := FALSE;
543 04DE  2   PHYSCONNECTFAIL := FALSE;
544 04E3  2   REPEAT XECOM_DO('N',ALRIGHT) UNTIL ALRIGHT;
545 04F1  2   REPEAT
546 04F1  2     GETDATA(INFO_FLAG,DATA_FLAG,TX_FLAG,IBYTE,DBYTE);
547 04FE  2   UNTIL ((NOT TX_FLAG) AND INFO_FLAG);
548 050A  2   CASE IBYTE OF
549 0518  2     'R' : RING_COUNT := RING_COUNT + 1;
550 051B  2     'V',
551 051B  2     'T' : PHYSCONNECTED := TRUE;
552 0523  2   OTHERWISE
553 0523  2     PHYSCONNECTFAIL := TRUE;
554 0528  2   END; (CASE)
555 053D  2   IF RING_COUNT > 9 THEN PHYSCONNECTFAIL := TRUE;
556 054D  2 END;
557 0000  1
558 0000  1 PROCEDURE MODEMCHECK;
559 054F  2 BEGIN
560 054F  2   IF (CONNECT_RESULT = ' ') THEN BEGIN
561 0557  2     MODEMCONNECTED := TRUE;
562 055C  2     MODEMCONNECTFAIL := FALSE;
563 0561  2   END ELSE BEGIN
564 0564  2     MODEMCONNECTED := FALSE;
565 0569  2     MODEMCONNECTFAIL := TRUE;
566 056E  2   END;
567 056E  2 END;
568 0000  1
569 0000  1 $GLOBPROC OFF$
570 0000  1 .

End of compilation, number of errors=   0
  LOCATION OBJECT CODE LINE      SOURCE LINE 1 "8085"
                    2 ;
                    3 ; TELEPHONE BOOK FOR MIAMI
                    4 ;
                    5
                    6
                    7            GLB          PHONEBOOK
  0000              8 PHONEBOOK
  0000 3537323131   9            ASC          "5721091
  0014 2020202020  10            ASC          "
  0028 2020202020  11            ASC          "
  003C 2020202020  12            ASC          "
  0050 2020202020  13            ASC          "
  0064 2020202020  14            ASC          "
  0078 2020202020  15            ASC          "
```

```
008C 2020202020    16        ASC        "          "
00A0 2020202020    17        ASC        "          "
00B4 2020202020    18        ASC        "          "
                   19        END
```

```
  1 0000  1  "8085"
  2 0000  1  $EXTENSIONS ON$
  3 0000  1  $SEPARATE ON$
  4 0000  1  $OPTIMIZE OFF$
  5 0000  1  PROGRAM XET;
  6 0000  1  TYPE
  7 0000  1    BITS        = (D0,D1,D2,D3,D4,D5,D6,D7);
  8 0000  1    S8          = SET OF BITS;
  9 0000  1    CMDBITS     = (TXEN,DTR,RXEN,SBRK,ER,RTS,IR,EH);
 10 0000  1    CMDBYTE     = SET OF CMDBITS;
 11 0000  1    STSBITS     = (XETXRDY,XERXRDY,XETXE,XEPE,XEOE,XEFE,XEDET,XEDSR);
 12 0000  1    STSBYTE     = SET OF STSBITS;
 13 0000  1  VAR
 14 0000  1  $GLOBVAR ON$
 15 0000  1    WRITE_ENABLED : BOOLEAN;      (Must be true to write to XeCom)
 16 0001  1  $GLOBVAR OFF$
 17 0001  1  $EXTVAR ON$
 18 0001  1    XECOM_COMMAND : SET OF BITS;
 19 0001  1    INTRMSK       : S8;           (Used by SMASK to set interrupt mask)
 20 0001  1  $EXTVAR OFF$
 21 0001  1  $ORG 0F600H$
 22 0001  1    XE_D          : BYTE;         (XeCOM data register)
 23 0001  1    XE_C          : CMDBYTE;      (XeCOM command register -- write only)
 24 0001  1  $END_ORG$
 25 0001  1  $ORG 0F601H$
 26 0001  1    XE_STS        : STSBYTE;      (XeCom status register -- read only)
 27 0001  1  $END_ORG$
 28 0001  1  $ORG 0F601H$
 29 0001  1    XE_MODE       : S8;           (XeCom mode register -- write only)
 30 0001  1  $END_ORG$
 31 0001  1  $ORG 0F100H$
 32 0001  1    PORT_CMD      : S8;           (8155 command port)
 33 0001  1    PORT_A        : S8;           (OUTPUTS)
 34 0001  1                                  (D7 - Ringer relay; 1==) bell generator)
 35 0001  1                                  (                    0==) pseudo ringback)
 36 0001  1                                  (D6 - Elite relay;   1==) across ring generators)
 37 0001  1                                  (                    0==) on the line)
 38 0001  1                                  (D1 - Active lite;   1 ==) on)
 39 0001  1    PORT_B        : S8;           (INPUTS)
 40 0001  1    PORT_C        : S8;           (OUTPUTS)
 41 0001  1  $END_ORG$
 42 0000  1
 43 0000  1  PROCEDURE INIT_QUEUE;   EXTERNAL; (QUEUE - initializes the queue pointers; empties the qu
 44 0000  1  PROCEDURE SMASK;        EXTERNAL; (INTR -- uses INTRMSK to SIM)
 45 0000  1  PROCEDURE DISABLE;      EXTERNAL; (INTR -- executes the DI command)
 46 0000  1  PROCEDURE ENABLE;       EXTERNAL; (INTR -- executes the EI command)
 47 0000  1  PROCEDURE ENABLE_75;    EXTERNAL; (RATE ALARM STUFF)
 48 0000  1  PROCEDURE DISABLE_75;   EXTERNAL; (RATE ALARM STUFF)
 49 0000  1
 50 0000  1
```

```
51 0000  1
52 0000  1  PROCEDURE ACTIVELITEON;          EXTERNAL;
53 0000  1
54 0000  1
55 0000  1  $PAGE$
56 0000  1  $GLOBPROC ON$
57 0000  1  PROCEDURE DISABLE_INOUT;
58 0000  2  (This procedure disables the interrupts generated by the TxRDY pin
59 0000  2   of the XeCOM and and 5 ms interrupt. It does not generally disable
60 0000  2   the interrupts but does reset the 7.5 latch)
61 0000  2  (Note that the 5.5 (1 second) interrupt mask status is uneffected
62 0000  2   by this routine.)
63 0000  2  BEGIN
64 0000  2  ( DISABLE;                                         )
65 0000  2  ( INTRMSK := INTRMSK + [D4,D3,D2,D1];              )
66 0000  2  ( SMASK;                                           )
67 0000  2  ( ENABLE;                                          )
68 0000  2    DISABLE_75;   (17 Sept 85 Rate Alarm Stuff)
69 0003  2  END;
70 0000  1
71 0000  1  PROCEDURE ENABLE_INOUT;
72 0004  2  (This procedure initializes the buffer for input data and enables the
73 0004  2   interrupts)
74 0004  2  (Note that the TxRDY interrupt (6.5) is unmasked by the interrupt
75 0004  2   service routine of the 7.5 interrupt when there is a data byte to
76 0004  2   send. We make sure it is masked here before we enable the interrupts)
77 0004  2  (Note that the 5.5 (1 second) interrupt mask status is uneffected
78 0004  2   by this routine.)
79 0004  2  BEGIN
80 0004  2  ( DISABLE;                                         )
81 0004  2  ( INIT_QUEUE;                        (Resets the queue -- erases what is stored)
82 0004  2  ( INTRMSK := (INTRMSK + [D4,D3,D1]) - [D2];  (Reset 7.5 latch, mask 6.5(TxRDY))
83 0004  2  (                                    (Unmask 7.5(Ums))
84 0004  2  ( SMASK;                                           )
85 0004  2    INIT_QUEUE;
86 0007  2    ENABLE_75;
87 000A  2    XE_C := [TXEN,DTR,RXEN,ER,RTS];
88 000F  2  ( ENABLE;                                          )
89 000F  2  END;
90 0000  1
91 0000  1  $PAGE$
92 0000  1  PROCEDURE XECOM_RESET;
93 0000  2  (Here we hit the Xecom hardware reset line and program the mode
94 0000  2   byte and send the command register with DTR set high. Experience
95 0000  2   has shown that DTR is required for the DET (SYNDET/BRKDET) pin to
96 0000  2   reliably show the bell status)
97 0000  2  VAR
98 0000  2    I            : INTEGER;
99 0010  2  BEGIN
100 0010  2   PORT_C := PORT_C + [D5];     (Hardware reset high)
101 0018  2   FOR I := 1 TO 1000 DO BEGIN END;
102 003A  2   PORT_C := PORT_C - [D5];     (Hardware reset lo)
103 0044  2                                ( D7,D6 = 01 ==) 1 stop bit     )
104 0044  2                                ( D5,D4 = 00 ==) parity disabled )
105 0044  2                                ( D3,D2 = 11 ==) 8 bits/char    )
106 0044  2                                ( D1,D0 = 01 ==) 1200 baud async)
107 0044  2   XECOM_COMMAND := [D6,D3,D2,D0];     (Set the mode per above)
```

```
108 0049  2    XECOM_COMMAND := [D0,D1,D2,D4,D5];
109 004E  2    WHILE (XECOM_COMMAND * [D0] = []) DO;
110 005B  2  END;
111 0000  1
112 0000  1  PROCEDURE INTERCOM;
113 0000  2  (This procedure sets up the intercom mode.  The telephone is online
114 0000  2   in parallel with the Xecom.  No writes can occur here.  The data
115 0000  2   I/O interrupts are disabled.)
116 0000  2  VAR
117 0000  2     JUNK         : BYTE;                           (Used for buffer cleanout)
118 005C  2  BEGIN
119 005C  2     DISABLE_INOUT;                                 (Mask the 5 ms and TxRDY interrupts)
120 005F  2     XE_C := [TXEN,DTR,RXEN];                       (Make sure receiver is enabled)
121 0064  2
122 0064  2  (************)
123 0064  2     XE_D := 'H';                                   (Disconnect modems--offhook)
124 0069  2                                                    (No information byte possible here)
125 0069  2     REPEAT UNTIL (XETXRDY IN XE_STS);              (Wait for the function to complete)
126 0075  2
127 0075  2     WHILE (XERXRDY IN XE_STS) DO JUNK := XE_D;     (Here we clean out the data buffer)
128 008A  2  (************)
129 008A  2     XE_D := #16H;     (Function '^V')              (Connect audio input for ring)
130 008F  2                                                    (No information byte possible here)
131 008F  2     REPEAT UNTIL (XETXRDY IN XE_STS);              (Wait for the function to complete)
132 009B  2
133 009B  2     WHILE (XERXRDY IN XE_STS) DO JUNK := XE_D;     (Here we clean out the data buffer)
134 00B0  2  (************)
135 00B0  2     XE_C := [DTR,ER];                              (Set DTR, reset errors)
136 00B5  2     XE_C := [DTR,TXEN,RXEN];                       (Set DSR, enable receiver and xmitter)
137 00BA  2
138 00BA  2     XE_D := 'D';                                   (Take the modem offhook and go to DTMF)
139 00BF  2     REPEAT UNTIL (XETXRDY IN XE_STS);              (Wait for the function to complete)
140 00CB  2                                                    (Info byte '1' possible)
141 00CB  2                                                    (....but under what circumstances??)
142 00CB  2
143 00CB  2     WRITE_ENABLED := FALSE;                        (Don't allow writes here -- functions)
144 00D0  2                                                    (Below is ELITE to online)
145 00D0  2     PORT_A := PORT_A - [D6];                       (Do this last to save the ears)
146 00DA  2     XE_C := [DTR,RXEN,TXEN];                       (Set up for receive)
147 00DF  2  END;
148 0000  1
149 0000  1  FUNCTION DATALINK: BYTE;
150 00E0  2  (This sets up the digital communications in the answer mode between
151 00E0  2   the XeCOM and Casper.)
152 00E0  2  (The value returned is any information byte that was returned from
153 00E0  2   the Answer function.  If the function returned normally, a space is
154 00E0  2   returned)
155 00E0  2  BEGIN
156 00E0  2     PORT_A := (PORT_A - [D3,D2]) + [D6];           (Turn off the ringback and bell ring
                                                                generators)
157 00ED  2                                                    (Do this so below we don't come across
                                                                a bell ringing with ear )
158 00ED  2                                                    (Elite off the line to save the ears)
159 00ED  2     XE_C := [DTR];                                 (Set up for function write)
160 00F2  2     REPEAT UNTIL (XETXRDY IN XE_STS);              (Wait for it to complete)
161 00FE  2     XE_D := 'A';                                   (go into answer mode)
162 0103  2     REPEAT UNTIL (XETXRDY IN XE_STS);              (Wait for it to complete)
```

```
163 010F  2       IF ((XERXRDY IN XE_STS) AND (NOT(XEDSR IN XE_STS)))
164 0120  2             THEN DATALINK := XE_D       (If we get a info byte, here it is)
165 0129  2             ELSE
166 0129  2             BEGIN
167 0129  2                  DATALINK := ' ';       (Return for normal)
168 012E  2                  XE_C := [RTS,TXEN,RXEN,ER,DTR];  (Set up for 2 way link)
169 0133  2                  ENABLE_INOUT;          (Initialize the queue and get things
                                                    going)
170 0136  2             END;
171 0136  2       END;
172 0000  1  $GLOBPROC OFF$
173 0000  1  .
End of compilation, number of errors=    0
FILE: SAMPLER:TLJpbs   H: 64000 - Pascal 1 0000  1  "8085"
  2 0000  1  TITLE "SAMPLER -- REAL-TIME ECG PREPROCESSOR"
**** ERROR ??       ^3                                      ^430
  3 0000  1
  4 0000  1  ; CHANGE HISTORY:
  5 0000  1  ;   20 SEP 85 -- TL JIRAK & TC EVANS -- BASELINE VERSION CREATED
**** ERROR ??                 ^6
  6 0000  1
  7 0000  1  ; DESCRIPTION:
  8 0000  1  ;   THIS MODULE CONTAINS THE REAL-TIME ECG PREPROCESSOR AND SEGMENTIZER
  9 0000  1  ;   USED BY THE ECG RATE MONITOR SOFTWARE IN THE TransCare (tm) PATIENT
 10 0000  1  ;   BASESTATION (8085 WITH MEMORY-MAPPED IO).  THE RATE MONITOR SOFTWARE
 11 0000  1  ;   IS A MODIFICATION OF THE SAM I (REALYST) ECG ANALYSIS ALGORITHM.
 12 0000  1  ;   THIS MODULE WAS CREATED BY CONVERTING THE SAM I (REALYST) MODULE
 13 0000  1  ;   "MAIN" (VERSION 2E) FROM INTEL ASSEMBLER FORMAT TO HP64000 ASSEMBLER
**** ERROR ??        ^450          ^450
 14 0000  1  ;   FORMAT AND MODIFING THE CODE TO USE THE BASESTATION'S IO AND
**** ERROR ??                                                      ^202,450
 15 0000  1  ;   ELIMINATE FEATURES NOT USED IN THE RATE MONITOR APPLICATION.
 16 0000  1  ;   SOME VARIABLES WERE RENAMED; THE ORIGINAL NAMES ARE IN CURLY
 17 0000  1  ;   BRACKETS.  THE RATE MONITOR BACKGROUND (NON-REAL-TIME) PORTION IS
 18 0000  1  ;   CONTROLLED BY MODULE "SM" AND USES PROCEDURES AND FUNCTIONS IN
**** ERROR ??                              ^450
 19 0000  1  ;   MODULES "RSENSE" AND "MONITOR".
**** ERROR ??               ^450         ^450
 20 0000  1  SKIP
 21 0000  1  CHECK_TIME  EQU    50D          ; SET CHECK_ECG INTERVAL TO 500MS
**** ERROR ??                                                        ^15,455
 22 0000  1  FALSE       EQU    00H          ; BOOLEAN FALSE
**** ERROR ??                   ^455
 23 0000  1  TRUE        EQU    01H          ; BOOLEAN TRUE
**** ERROR ??                   ^455
 24 0000  1  SPIKE_CODE  EQU    255D         ; VALUE (FFH) SENT TO INDICATE PACER
 25 0000  1                                  ; SPIKE DETECTION.
 26 0000  1  T100MS      EQU    30D          ; 100 MILLISECOND CONSTANT
 27 0000  1  MAX_SEGIDX  EQU    19D          ; MAXIMUM OF SEGMENT BUFFER POINTER
 28 0000  1  SBSIZ       EQU    2*(MAX_SEGIDX+1) ; SIZE OF EACH SEGMENT BUFFER ARRAY
 29 0000  1
 30 0000  1
 31 0000  1       EXT  INBYTE         ; PROCEDURE IN MODULE "CLOCKIO" THAT
**** ERROR ??
```

FILE: SAMPLER:TLJpbs   HEWLETT-PACKARD, COMPILER -- REAL TIME ECG PREPROCESSOR

LOCATION OBJECT CODE LINE   SOURCE LINE

```
          1     "8085"
          3
          4   ; CHANGE HISTORY:
          5   ;   20 SEP 85 — TL JIRAK & TC EVANS — BASELINE VERSION CREATED
          6
          7   ; DESCRIPTION:
          8   ;   THIS MODULE CONTAINS THE REAL-TIME ECG PREPROCESSOR AND SEGMENTIZER
          9   ;   USED BY THE ECG RATE MONITOR SOFTWARE IN THE TransCare (tm) PATIENT
         10   ;   BASESTATION (8085 WITH MEMORY-MAPPED IO). THE RATE MONITOR SOFTWARE
         11   ;   IS A MODIFICATION OF THE SAM I (REALYST) ECG ANALYSIS ALGORITHM.
         12   ;   THIS MODULE WAS CREATED BY CONVERTING THE SAM I (REALYST) MODULE
         13   ;   "MAIN" (VERSION 2E) FROM INTEL ASSEMBLER FORMAT TO HP64000 ASSEMBLER
         14   ;   FORMAT AND MODIFING THE CODE TO USE THE BASESTATION'S IO AND
         15   ;   ELIMINATE FEATURES NOT USED IN THE RATE MONITOR APPLICATION.
         16   ;   SOME VARIABLES WERE RENAMED; THE ORIGINAL NAMES ARE IN CURLY
         17   ;   BRACKETS. THE RATE MONITOR BACKGROUND (NON-REAL-TIME) PORTION IS
         18   ;   CONTROLLED BY MODULE "SM" AND USES PROCEDURES AND FUNCTIONS IN
         19   ;   MODULES "RSENSE" AND "MONITOR".
(0032)   21   CHECK_TIME   EQU   50D              ; SET CHECK_ECG INTERVAL TO 500MS
(0000)   22   FALSE        EQU   00H              ; BOOLEAN FALSE
(0001)   23   TRUE         EQU   01H              ; BOOLEAN TRUE
(00FF)   24   SPIKE_CODE   EQU   255D             ; VALUE (FFH) SENT TO INDICATE PACER
         25                                        ; SPIKE DETECTION.
(001E)   26   T100MS       EQU   30D              ; 100 MILLISECOND CONSTANT
(0013)   27   MAX_SEGIDX   EQU   19D              ; MAXIMUM OF SEGMENT BUFFER POINTER
(0028)   28   SBSIZ        EQU   2*(MAX_SEGIDX+1) ; SIZE OF EACH SEGMENT BUFFER ARRAY
         29
         30
         31        EXT  INBYTE         ; PROCEDURE IN MODULE "CLOCKIO" THAT
         32                             ; SENDS DATA TO CASPER.
         33        EXT  R_WAVE_TYPE    ; VARIABLE IN MODULE "RSENSE" INDICATES LEVEL
         34                             ; OF DATA UNRELIABILITY.
         35        EXT  SPIKE_ENABLED  ; BOOLEAN IN "CLOCKIO" SET TRUE TO ENABLE
         36                             ; SENDING SPIKE_CODE WHEN PACER SPIKE DETECTED.
         37
         38
         39        GLB  ABSVAL_SCALE   ; DIFFERENTIATOR SCALE FACTOR CONTROL.
         40        GLB  BUFFER_LEVEL   ; NUMBER OF SEGMENTS DETECTED SINCE THE
         41                             ; CANDIDATE (BLEVEL).
         42        GLB  CANDIDATE_FLAG ; SET TRUE WHENEVER A CANDIDATE QRS
         43                             ; IS DETECTED (CANQRS).
         44        GLB  CANDIDATE_PTR  ; BUFFER LOCATION OF CANDIDATE QRS DETECTED
         45                             ; BY PREPROCESSOR (PSIGPT).
         46        GLB  CHECK_ECG      ; SET TRUE EVERY CHECK_TIME WHEN NEW PEAK_BUFFER
         47                             ; AND ECG_PP ARE READY.
         48        GLB  DISABLE_75     ; MASK RST 7.5 WITHOUT DISABLING INTERRUPTS AND
         49                             ; FLAG END OF RATE MONITORING.
         50        GLB  ECG_PP         ; P-P ECG AMPLITUDE.
         51        GLB  ENABLE_75      ; PROCEDURE THAT INITIALIZES SAMPLER AND
         52                             ; ENABLES THE RST 7.5 INTERRUPT.
         53        GLB  INSIGT         ; SEGMENT SENSING THRESHOLD.
         54        GLB  MINUTES        ; MINUTES PORTION OF TOC (ETIME).
         55        GLB  MODEM_ON       ; ENABLES DATA TRANSMISSION IF SAMPLER ACTIVE.
```

```
         56    GLB  MODEM_OFF          ; DISABLES DATA TRANSMISSION BUT DOES NOT
         57                            ; DISABLE RST 7.5 (SAMPLER STAYS ACTIVE).
         58    GLB  PEAK_SLOPE         ; PEAK DIFFERENTIAL DURING LAST CHECK_TIME.
         59    GLB  SAMPLE_ON          ; SET TRUE TO ENABLE RATE MONITOR BACKGROUND.
         60    GLB  SAMPLER            ; ENTRY POINT TO 300HZ SAMPLING PROCEDURE.
         61    GLB  SIGT               ; SIGNIFICANT SEGMENT THRESHOLD.
         62    GLB  XMIT_ECG           ; ECG (OR PACER ARTIFACT) DATA BYTE TO BE
         63                            ; TRANSMITTED TO CASPER.
         64
         65                            ; BASE ADDRESSES OF SEGMENT DATA BUFFERS USED
         66                            ; AS PASCAL ARRAYS (SEGBUF)
         67    GLB  END_TIME           ; END_TIME     : ARRAY[0..MAX_SEGIDX] OF INTEGER;
         68    GLB  PEAK_MAG           ; PEAK_MAG     : ARRAY[0..MAX_SEGIDX] OF INTEGER;
         69    GLB  PP_START_TIME      ; PP_START_TIME: ARRAY[0..MAX_SEGIDX] OF INTEGER;
         70    GLB  PP_VALUE           ; PP_VALUE     : ARRAY[0..MAX_SEGIDX] OF INTEGER;
         71    GLB  START_MINUTE       ; START_MINUTE : ARRAY[0..MAX_SEGIDX] OF INTEGER;
         72    GLB  START_SUBMIN       ; START_SUBMIN : ARRAY[0..MAX_SEGIDX] OF INTEGER;
         73    GLB  START_TIME         ; START_TIME   : ARRAY[0..MAX_SEGIDX] OF INTEGER;
         75    ORG  0F800H             ; MEMORY-MAPPED IO.
F800     76 ECG_INPUT:   DS 1          ; ECG CHANNEL USED FOR ANALYSIS (READ ONLY).
         77
         78
         79    DATA
         80
0000     81 ABSVAL_SCALE: DS 1         ; CONTROL DIFFERENTIATOR SCALE FACTOR -- NUMBER
         82                            ; OF TIMES ABSOLUTE VALUE IS HALVED.
0001     83 ARTFLAG:      DS 1         ; PACER ARTIFACT FLAG.
0002     84 BUFFER_LEVEL: DS 1         ; NUMBER OF SEGMENTS DETECTED SINCE
         85                            ; LAST QRS CANDIDATE (BLEVEL).
0003     86 CANDIDATE_FLAG: DS 1       ; SET TRUE WHENEVER A CANDIDATE
         87                            ; QRS IS DETECTED (CANQRS).
0004     88 CANDIDATE_PTR: DS 1        ; BUFFER LOCATION OF CANDIDATE QRS
         89                            ; DETECTED BY PREPROCESSOR (PSIGPT).
0005     90 CANISO:       DS 2         ; ACCUMULATES TIME FROM THE LAST
         91                            ; SIGNIFICANT SEGMENT END TO THE NEXT
         92                            ; SIGNIFICANT SEGMENT START
0007     93 CDPEAK:       DS 1         ; CURRENT DIFFERENTIAL PEAK.
0008     94 CHECK_ECG:    DS 1         ; SET TRUE EVERY CHECK_TIME WHEN NEW PEAK_BUFFER
         95                            ; AND ECG_PP ARE READY.
0009     96 CHECK_TMR:    DS 1         ; USED TO COUNT DOWN CHECK_TIME BY 10MS TICKS.
000A     97 DIFPTR:       DS 2         ; SELECTS DIFFERENTIAL COMPUTATION.
000C     98 ECG_MN_SUM:   DS 2         ; MINIMUM VALUE OF SUMMED ECG SAMPLES.
000E     99 ECG_MX_SUM:   DS 2         ; MAXIMUM VALUE OF SUMMED ECG SAMPLES.
0010    100 ECG_PP:       DS 2         ; P-P ECG AMPLITUDE.
0012    101 EIN0:         DS 2         ; BUFFER FOR ANALYZED CHANNEL INPUT USED FOR
0014    102 EIN1:         DS 2         ; SUMMING 5 CONSECUTIVE ECG BYTES.
0016    103 EIN2:         DS 2
0018    104 EIN3:         DS 2
001A    105 EIN4:         DS 2
001C    106 EINPTR:       DS 2         ; DIRECTS INPUT TO APPROPRIATE EINx BUFFER.
001E    107 FLAG_10MS:    DS 1         ; SET TRUE EVERY 10MS.
001F    108 INSIGT:       DS 1         ; INSIGNIFICANCE THRESHOLD.
0020    109 MINUTES:      DS 2         ; MINUTES PORTION OF TOD (ETIME).
0022    110 PEAK_BUFFER:  DS 1         ; ACCUMULATES PEAK DIFFERENTIAL FOR PEAK_SLOPE.
0023    111 PEAK_SLOPE:   DS 2         ; PEAK DIFFERENTIAL DURING LAST CHECK_TIME.
0025    112 PPINT:        DS 2         ; LAST PACE-TO-PACE INTERVAL.
```

```
0027      113 PPTMR:        DS 2    ; PACE-SPIKE TO PACE-SPIKE TIMER.
0029      114 PSFLAG:       DS 1    ; PACE-SPIKE FLAG -- USED IN SPIKE
          115                       ; DETECT PROCESS.
002A      116 SAMPLE_ON:    DS 1    ; SET TRUE TO ENABLE RATE MONITOR BACKGROUND.
002B      117 SEFLAG:       DS 1    ; SEGMENT START & END FLAG.
          118 ;(SEGBUF) -- QRS SEGMENT DATA CIRCULAR BUFFERS:
002C      119 END_TIME:     DS SBSIZ ; END_TIME : ARRAY[0..MAX_SEGIDX] OF INTEGER;
          120                       ; SEGMENT DURATION (SEGTMR) -- HAS A
          121                       ; MAXIMUM VALUE OF 255.
0054      122 PEAK_MAG:     DS SBSIZ ; PEAK_MAG : ARRAY[0..MAX_SEGIDX] OF INTEGER;
          123                       ; PEAK OF DIFFERENTIAL (CDPEAK) FOR EACH
          124                       ; SEGMENT -- MAXIMUM VALUE OF 255.
007C      125 PP_START_TIME: DS SBSIZ ; PP_START_TIME : ARRAY[0..MAX_SEGIDX] OF INTEGER;
          126                       ; VALUE OF PPTMR AT SEGMENT START.
00A4      127 PP_VALUE:     DS SBSIZ ; PP_VALUE : ARRAY[0..MAX_SEGIDX] OF INTEGER;
          128                       ; PPINT AT SEGMENT START.
00CC      129 START_MINUTE: DS SBSIZ ; START_MINUTE : ARRAY[0..MAX_SEGIDX] OF INTEGER;
          130                       ; VALUE OF MINUTES PORTION OF SYSTEM TOD
          131                       ; AT SEGMENT START.
00F4      132 START_SUBMIN: DS SBSIZ ; START_SUBMIN : ARRAY[0..MAX_SEGIDX] OF INTEGER;
          133                       ; VALUE OF SUBMIN PORTION OF SYSTEM TOD
          134                       ; AT SEGMENT START.
011C      135 START_TIME:   DS SBSIZ ; START_TIME : ARRAY[0..MAX_SEGIDX] OF INTEGER;
          136                       ; TIME FROM THE END OF THE LAST SEGMENT TO
          137                       ; THE START OF THE CURRENT SEGMENT (SEGISO).
0144      138 SEGCNT:       DS 1    ; NUMBER OF ENTRIES IN (SEGBUF) BUFFERS.
0145      139 SEGIDX:       DS 1    ; POINTER TO ARRAY ELEMENTS IN SEGMENT DATA
          140                       ; CIRCULAR BUFFERS THAT WILL STORE DATA FROM
          141                       ; THE NEXT COMPLETED SEGMENT.
0146      142 SEGISO:       DS 2    ; ACCUMULATES TIME FROM THE END OF A
          143                       ; SEGMENT TO THE START OF THE NEXT
          144                       ; SEGMENT
0148      145 SEGTMR:       DS 1    ; SEGMENT TIMER.
0149      146 SGNREF:       DS 1    ; SIGN OF DIFFERENTIAL.
014A      147 SIGPTR:       DS 1    ; CURRENT VALUE OF SEGIDX AFTER A
          148                       ; SIGNIFICANT SEGMENT HAS BEEN
          149                       ; DETECTED
014B      150 SIGT:         DS 1    ; SIGNIFICANCE THRESHOLD.
014C      151 SLOPE_MAG:    DS 1    ; CURRENT DIFFERENTIAL (SLOPE) MAGNITUDE.
014D      152 SUBMIN:       DS 2    ; A/D SAMPLE COUNT; RESET
          153                       ; EVERY MINUTE
014F      154 SUMBUF:       DS 2    ; SUM OF ECG INPUT FOR FIVE SAMPLES (OVER
          155                       ; 16.666667 MS) (AVEBUF).
0151      156 SUMIN0:       DS 2    ; BUFFERS FOR ECG BYTES SUMMED OVER 16.67MS --
0153      157 SUMIN1:       DS 2    ; USED FOR COMPUTING THE BAND-LIMITED
0155      158 SUMIN2:       DS 2    ; DIFFERENTIAL (AVEIN0 THRU AVLIN5).
0157      159 SUMIN3:       DS 2
0159      160 SUMIN4:       DS 2
015B      161 SUMIN5:       DS 2
015D      162 XMIT_ACTIVE:  DS 1    ; SET TRUE WHEN MODEM IS TO SEND DATA.
015E      163 XMIT_ARTFLAG: DS 1    ; FLAG PACER ARTIFACT CODE TO BE INSERTED
          164                       ; FOR TRANSMISSION.
015F      165 XMIT_ECG:     DS 1    ; AVERAGED ECG (OR PACER ARTIFACT) DATA BYTE
          166                       ; TO BE TRANSMITTED TO CASPER.
0160      167 XMIT_SUMBUF:  DS 1    ; BUFFER FOR SUM OF 5 ECG BYTES TO BE PROCESSED
          168                       ; FOR TRANSMISSION.
```

```
170  PROG
171
172 ; INTERRUPT ROUTINE SAMPLER -- DRIVEN BY A 300 HZ SAMPLE CLOCK CONNECTED
173 ;   TO RST 7.5. UPDATES SOFTWARE TIMER, DOES ECG REAL-TIME PROCESSING, STORES
174 ;   STORES ECG SAMPLES IN WAVEFORM MEMORY, AND CALLS THE TRANSMIT
175 ;   PROCEDURE EVERY 1MS.
176
0000 F5        177 SAMPLER:   PUSH PSW
0001 C5        178            PUSH B
0002 D5        179            PUSH D
0003 E5        180            PUSH H
0004 3EC0      181            MVI A,11000000B      ; SOD HI TO CHECK REAL TIME USE.
0006 30        182            SIM
               183
               184 ; MANAGE SYSTEM TIME OCCURRANCE CLOCK (TOC).
0007 2A014D    185            LHLD SUBMIN          ; UPDATE LOW-ORDER PART OF TOC.
000A 23        186            INX H
000B 22014D    187            SHLD SUBMIN
000E 11B9D0    188            LXI D,-18000         ; TEST FOR ELAPSED MINUTE
0011 19        189            DAD D
0012 D2002F    190            JNC GET_SAMPLE       ; IF MINUTE NOT ELAPSED
0015 210000    191            LXI H,0              ; RESET SAMPLE COUNT
0018 22014D    192            SHLD SUBMIN
001B 2A0020    193            LHLD MINUTES         ; INDEX MINUTE COUNT
001E 23        194            INX H
001F 7C        195            MOV A,H              ; CHECK IF MINUTES HAS ROLLED OVER FROM
0020 17        196            RAL                  ; 7FFFH (POSITIVE INTEGER) TO 8000H (NEGATIVE
0021 D2002C    197            JNC STILL_POS        ; INTEGER).
0024 3E08      198            MVI A,8              ; TELL QRS DETECTION PROCESS TO IGNORE THE
0026 320060    199            STA R_WAVE_TYPE      ; NEXT FEW BEATS.
0029 210000    200            LXI H,0              ; RESET MINUTES.
002C 220020    201 STILL_POS: SHLD MINUTES
               202
               203 ; INPUT ECG SAMPLE AND STORE FOR AVERAGING.
002F 21F800    204 GET_SAMPLE: LXI H,ECG_INPUT     ; LOAD 8-BIT SAMPLE INTO DE.
0032 5E        205            MOV E,M
0033 1600      206            MVI D,0
0035 2A001C    207            LHLD EINPTR          ; JUMP TO STORAGE ROUTINE.
0038 E9        208            PCHL
0039 EB        209 ESTOR0:    XCHG
003A 220012    210            SHLD EIN0            ; STORE SAMPLE 0.
003D 210043    211            LXI H,ESTOR1
0040 C30068    212            JMP EINDUN
0043 EB        213 ESTOR1:    XCHG
0044 220014    214            SHLD EIN1            ; STORE SAMPLE 1.
0047 21004D    215            LXI H,ESTOR2
004A C30068    216            JMP EINDUN
004D EB        217 ESTOR2:    XCHG
004E 220016    218            SHLD EIN2            ; STORE SAMPLE 2.
0051 210057    219            LXI H,ESTOR3
0054 C30068    220            JMP EINDUN
0057 EB        221 ESTOR3:    XCHG
0058 220018    222            SHLD EIN3            ; STORE SAMPLE 3.
005B 210061    223            LXI H,ESTOR4
005E C30068    224            JMP EINDUN
0061 EB        225 ESTOR4:    XCHG
0062 22001A    226            SHLD EIN4            ; STORE SAMPLE 4.
```

```
0065 210039      227           LXI  H,ESTOR0
0068 22001C      228 EINDUN:   SHLD EINPTR        ; READY FOR NEXT SAMPLE.
                 229
                 230 ; LOOK FOR PACE SPIKE.
006B 210029      231           LXI  H,PSFLAG
006E 20          232           RIM                ; LOOK AT SPIKE DETECTOR OUTPUT
006F 17          233           RAL                ; (B7 = 1 WHEN SPIKE DETECTED).
0071 DA0087      234           JC   SPIKE
0073 3600        235           MVI  M,FALSE       ; NO DETECT, SO CLEAR PSFLAG.
0075 2A0027      236 IPPT:     LHLD PPTMR         ; INCREMENT PPTMR.
0078 23          237           INX  H
0079 7C          238           MOV  A,H           ; CHECK IF PPTMR HAS ROLLED OVER FROM
007A 17          239           RAL                ; 7FFFH (POSITIVE INTEGER) TO 8000H (NEGATIVE
007B D20081      240           JNC  SPPT          ; INTEGER).
007E 217FFF      241           LXI  H,7FFFH       ; PREVENT TIMER ROLL OVER.
0081 220027      242 SPPT:     SHLD PPTMR         ; STORE PPTMR.
0084 C3009F      243           JMP  IST
0087 7E          244 SPIKE:    MOV  A,M           ; SPIKE DETECTED -- IGNORE IF
0088 B7          245           ORA  A             ; NOT LEADING EDGE.
0089 C20075      246           JNZ  IPPT
008C 3601        247           MVI  M,TRUE        ; SET PSFLAG ON SPIKE DETECT.
008E 2A0027      248           LHLD PPTMR         ; SAVE CURRENT PPTMR VALUE.
0091 220025      249           SHLD PPINT
0094 210000      250           LXI  H,0           ; ZERO PPTMR.
0097 220027      251           SHLD PPTMR
009A 3E01        252           MVI  A,TRUE        ; SET ARTIFACT DETECTED FLAG.
009C 320001      253           STA  ARTFLAG
                 254
                 255 ; INCREMENT THE SEGMENT TIMER.
009F 210148      256 IST:      LXI  H,SEGTMR
00A2 34          257           INR  M
00A3 C200A8      258           JNZ  SUMIN         ; IF SEGTMR < 0FFH
00A6 36FF        259           MVI  M,0FFH        ; ELSE HOLD AT 0FFH
                 260
                 261 ; COMPUTE THE SUM OF THE ECG SAMPLES TAKEN
                 262 ; DURING THE LAST 16.66667 MS.
00A8 2A0012      263 SUMIN:    LHLD EIN0          ; [HL] = EIN0.
00AB EB          264           XCHG
00AC 2A0014      265           LHLD EIN1
00AF 19          266           DAD  D             ; [HL] = EIN0 + EIN1.
00B0 EB          267           XCHG
00B1 2A0016      268           LHLD EIN2
00B4 19          269           DAD  D             ; [HL] = EIN0 + EIN1 + EIN2.
00B5 EB          270           XCHG
00B6 2A0018      271           LHLD EIN3
00B9 19          272           DAD  D             ; [HL] = EIN0 + EIN1 + EIN2
00BA EB          273           XCHG               ; + EIN3.
00BB 2A001A      274           LHLD EIN4
00BE 19          275           DAD  D             ; [HL] = EIN0 + EIN1 + EIN2
                 276                              ; + EIN3 + EIN4.
00BF 22014F      277           SHLD SUMBUF        ; STORE CURRENT SUM.
00C2 EB          278           XCHG
00C3 2A000A      279           LHLD DIFPTR        ; JUMP TO APPROPRIATE
00C6 E9          280           PCHL               ; COMPUTATION ROUTINE.
                 281
                 282 ; COMPUTE DIFFERENTIAL AND STORE CURRENT SUM
                 283 ; -- SUMS ARE STORED IN THE SUMINi VARIABLES
```

```
00C7 2A0151    284 DIFF0:   LHLD SUMIN0        ; GET OLDEST SUM.
00CA EB        285          XCHG
00CB 220151    286          SHLD SUMIN0        ; REPLACE IT WITH NEWEST.
00CE CD0331    287          CALL ABSVAL        ; COMPUTE DIFFERENTIAL.
00D1 2100D7    288          LXI H,DIFF1        ; LOAD NEXT POINTER.
00D4 C30148    289          JMP DIFDUN
00D7 2A0153    290 DIFF1:   LHLD SUMIN1        ; GET OLDEST SUM.
00DA EB        291          XCHG
00DB 220153    292          SHLD SUMIN1        ; REPLACE IT WITH NEWEST.
00DE CD0331    293          CALL ABSVAL        ; COMPUTE DIFFERENTIAL.
00E1 2100E7    294          LXI H,DIFF2        ; LOAD NEXT POINTER.
00E4 C30148    295          JMP DIFDUN
00E7 2A0155    296 DIFF2:   LHLD SUMIN2        ; GET OLDEST SUM.
00EA EB        297          XCHG
00EB 220155    298          SHLD SUMIN2        ; REPLACE IT WITH NEWEST.
00EE CD0331    299          CALL ABSVAL        ; COMPUTE DIFFERENTIAL.
00F1 220160    300          SHLD XMIT_SUMBUF   ; TIME TO SEND DATE TO CASPER, SO STORE
00F4 210001    301          LXI H,ARTFLAG      ; DATA IN BUFFERS AND SET SEND FLAG.
00F7 7E        302          MOV A,M
00F8 3600      303          MVI M,FALSE
00FA 21015E    304          LXI H,XMIT_ARTFLAG
00FD 77        305          MOV M,A
00FE 21001E    306          LXI H,FLAG_10MS
0101 3601      307          MVI M,TRUE
0103 210109    308          LXI H,DIFF3        ; LOAD NEXT POINTER.
0106 C30148    309          JMP DIFDUN
0109 2A0157    310 DIFF3:   LHLD SUMIN3        ; GET OLDEST SUM.
010C EB        311          XCHG
010D 220157    312          SHLD SUMIN3        ; REPLACE IT WITH NEWEST.
0110 CD0331    313          CALL ABSVAL        ; COMPUTE DIFFERENTIAL.
0113 210119    314          LXI H,DIFF4        ; LOAD NEXT POINTER.
0116 C30148    315          JMP DIFDUN
0119 2A0159    316 DIFF4:   LHLD SUMIN4        ; GET OLDEST SUM.
011C EB        317          XCHG
011D 220159    318          SHLD SUMIN4        ; REPLACE IT WITH NEWEST.
0120 CD0331    319          CALL ABSVAL        ; COMPUTE DIFFERENTIAL.
0123 210129    320          LXI H,DIFF5        ; LOAD NEXT POINTER.
0126 C30148    321          JMP DIFDUN
0129 2A015B    322 DIFF5:   LHLD SUMIN5        ; GET OLDEST SUM.
012C EB        323          XCHG
012D 22015B    324          SHLD SUMIN5        ; REPLACE IT WITH NEWEST.
0130 CD0331    325          CALL ABSVAL        ; COMPUTE DIFFERENTIAL.
0133 220160    326          SHLD XMIT_SUMBUF   ; TIME TO SEND DATE TO CASPER, SO STORE
0136 210001    327          LXI H,ARTFLAG      ; DATA IN BUFFERS AND SET SEND FLAG.
0139 7E        328          MOV A,M
013A 3600      329          MVI M,FALSE
013C 21015E    330          LXI H,XMIT_ARTFLAG
013F 77        331          MOV M,A
0140 21001E    332          LXI H,FLAG_10MS
0143 3601      333          MVI M,TRUE
0145 2100C7    334          LXI H,DIFF0        ; LOAD NEXT DIFPTR.
0148 22000A    335 DIFDUN:  SHLD DIFPTR        ; FINISH UP COMPUTATION.
014B 210149    336          LXI H,SGNREF       ; CHECK IF DIFFERENTIAL
014E 78        337          MOV A,B            ; CHANGED SIGN.
014F BE        338          CMP M
0150 CA0156    339          JZ DIF1ST
0153 70        340          MOV M,B            ; SIGN CHANGED -- STORE NEW
```

```
0154 0E00      341           MVI  C,0           ; SIGN AND ZERO DIFFERENTIAL.
0156 21002B    342 DIFTST:   LXI  H,SEFLAG      ; TEST DIFFERENTIAL (C) TO DECIDE
0159 79        343           MOV  A,C
015A 32014C    344           STA  SLOPE_MAG     ; MAGNITUDE OF CURRENT DIFFERENTIAL.
015D 3A001F    345           LDA  INSIGT        ; WHAT NEXT.
0160 B9        346           CMP  C
0161 DA0208    347           JC   SEG_EXISTS    ; (C))INSIGT UNTIL SEGMENT ENDS.
0164 7E        348           MOV  A,M           ; DIFFERENTIAL (= INSIGT, SO
0165 B7        349           ORA  A             ; SEE IF SEGMENT EVER STARTED.
0166 CA027F    350           JZ   DONE
               351
               352 ; A SEGMENT JUST ENDED, SO DO END OF SEGMENT PROCESSING.
0169 3600      353           MVI  M,FALSE       ; FLAG SEGMENT END.
016B 3A0148    354           LDA  SEGTMR        ; NO OTHER PROCESSING NEEDED
016E FE05      355           CPI  5             ; IF SEGMENT (= 13 MSEC.
0170 DA027F    356           JC   DONE
               357
               358 ; STORE SEGMENT END DATA AND, IF NECESSARY, FLAG NON-
               359 ; REAL-TIME PORTION TO ANALYZE SEGMENT BUFFER.
0173 210144    360           LXI  H,SEGCNT      ; INCREMENT SEGMENT COUNT
0176 34        361           INR  M
0177 2A0145    362           LHLD SEGIDX        ; OBTAIN BUFFER INDEX
017A 2600      363           MVI  H,0           ; DON'T WANT TOP BYTE
017C 29        364           DAD  H             ; * 2
017D EB        365           XCHG               ; (DE) = 2*SEGIDX
               366
               367 ; END_TIME[SEGIDX] := SEGTMR
017E 210148    368           LXI  H,SEGTMR
0181 4E        369           MOV  C,M
0182 0600      370           MVI  B,0           ; zero top byte , bc = SEGTMR
0184 21002C    371           LXI  H,END_TIME    ; HL = base of Pascal integer array
0187 19        372           DAD  D             ; add SEGIDX*2
0188 71        373           MOV  M,C           ; store to array
0189 23        374           INX  H             ; point to other half
018A 70        375           MOV  M,B           ; store to array
               376
               377 ; PEAK_MAG[SEGIDX] := CDPEAK
018B 210007    378           LXI  H,CDPEAK
018E 4E        379           MOV  C,M
018F 0600      380           MVI  B,0           ; zero top byte , bc = SEGTMR
0191 210054    381           LXI  H,PEAK_MAG    ; HL = base of Pascal integer array
0194 19        382           DAD  D             ; add SEGIDX*2
0195 71        383           MOV  M,C           ; store to array
0196 23        384           INX  H             ; point to other half
0197 70        385           MOV  M,B           ; store to array
               386
               387 ; START_TIME[SEGIDX] := SEGISO
0198 2A0146    388           LHLD SEGISO
019B 44        389           MOV  B,H
019C 4D        390           MOV  C,L           ; BC = value to be stored in array
019D 21011C    391           LXI  H,START_TIME  ; HL = base of Pascal integer array
01A0 19        392           DAD  D             ; add SEGIDX*2
01A1 71        393           MOV  M,C           ; store to array
01A2 23        394           INX  H             ; point to other half
01A3 70        395           MOV  M,B           ; store to array
               396
               397 ; TEST FOR LARGE SEGMENT.
```

```
01A4 211007      398            LXI  H,CDPEAK        ; CDPEAK > SIGT ?
01A7 3A014B      399            LDA  SIGT
01AA BE          400            CMP  M
01AB D201DF      401            JNC  NORMAL_END
                 402
                 403 ; A LARGE SEGMENT JUST ENDED, SO TEST IF CANDIDATE.
01AE A7          404            ANA  A               ; RESET CARRY BIT
01AF 2A0005      405            LHLD CANISO
01B2 EB          406            XCHG                 ; (DE) =CANISO
01B3 21001E      407            LXI  H,T100MS        ; (HL) = 100 MSEC CONSTANT
01B6 CD0365      408            CALL CMP16           ; TEST FOR CANISO > T100MS
01B9 D201D0      409            JNC  LARGE_END
                 410
                 411 ; LARGE SEGMENT ISOLATED, SO FLAG START OF NON-REAL-TIME ANALYSIS.
01BC 210003      412            LXI  H,CANDIDATE_FLAG
01BF 3601        413            MVI  M,TRUE
01C1 3A014A      414            LDA  SIGPTR
01C4 320004      415            STA  CANDIDATE_PTR   ; CANDIDATE IS LAST LARGE SEGMENT.
01C7 210144      416            LXI  H,SEGCNT
01CA 7E          417            MOV  A,M
01CB 320002      418            STA  BUFFER_LEVEL    ; BUFFER_LEVEL := SEGCNT
01CE 3600        419            MVI  M,0             ; RESET SEGCNT
                 420
                 421 ; CLEANUP AFTER END OF LARGE SEGMENT.
01D0 3A0145      422 LARGE_END: LDA  SEGIDX
01D3 32014A      423            STA  SIGPTR          ; SIGPTR = SEGIDX
01D6 210000      424            LXI  H,0
01D9 220005      425            SHLD CANISO          ; RESET CANISO
01DC C301EC      426            JMP  ALL_ENDS
                 427
                 428 ; CLEANUP AFTER TYPICAL SEGMENT END.
01DF 2A0148      429 NORMAL_END: LHLD SEGTMR         ; IF CDPEAK <= SIGT
01E2 EB          430            XCHG
01E3 1600        431            MVI  D,0             ; (DE) = SEGTMR
01E5 2A0005      432            LHLD CANISO
01E8 19          433            DAD  D
01E9 220005      434            SHLD CANISO          ; CANISO = CANISO + SEGTMR
                 435
                 436 ; COMPLETE SEGMENT END CLEANUP.
01EC 210000      437 ALL_ENDS:  LXI  H,0
01EF 220146      438            SHLD SEGISO          ; RESET SEGISO
01F2 AF          439            XRA  A
01F3 320148      440            STA  SEGTMR          ; RESET SEGTMR
01F6 210145      441            LXI  H,SEGIDX        ; ADVANCE SEGIDX
01F9 7E          442            MOV  A,M
01FA FE13        443            CPI  MAX_SEGIDX      ; TEST FOR SEGIDX >= MAX_SEGIDX
01FC D20203      444            JNC  RSTIDX          ; IF TRUE, ELSE
01FF 34          445            INR  M               ; INCREMENT SEGIDX
0200 C3027F      446            JMP  DONE
0203 3600        447 RSTIDX:    MVI  M,0             ; RESET SEGIDX
0205 C3027F      448            JMP  DONE
                 449
                 450 ; SEGMENT IN PROCESS OR JUST STARTED.
0208 7E          451 SEG_EXISTS: MOV A,M
0209 B7          452            ORA  A
020A C20276      453            JNZ  CKPEAK
020D 3601        454            MVI  M,TRUE          ; SEGMENT JUST STARTED, SO
```

```
020F 79          455           MOV A,C              ; SET SEFLAG AND
0211 320007      456           STA CDPEAK           ; STORE INITIAL CDPEAK.
0213 2A0148      457           LHLD SEGTMR          ; UPDATE SEGISO AND CANISO
0216 EB          458           XCHG
0217 1600        459           MVI D,0
0219 2A0146      460           LHLD SEGISO
021C 19          461           DAD D
021D 7C          462           MOV A,H              ; CHECK IF SEGISO ROLLED OVER FROM POSITIVE
021E 17          463           RAL                  ; TO NEGATIVE VALUES.
021F D20225      464           JNC UD_SEGISO
0222 217FFF      465           LXI H,7FFFH          ; HOLD SEGISO AS POSITIVE PASCAL INTEGER.
0225 220146      466 UD_SEGISO: SHLD SEGISO         ; SEGISO = SEGISO + SEGTMR
0228 2A0005      467           LHLD CANISO
022B 19          468           DAD D
022C 7C          469           MOV A,H              ; CHECK IF CANISO ROLLED OVER FROM POSITIVE
022D 17          470           RAL                  ; TO NEGATIVE VALUES.
022E D20234      471           JNC UD_CANISO
0231 217FFF      472           LXI H,7FFFH          ; HOLD CANISO AS POSITIVE PASCAL INTEGER.
0234 220015      473 UD_CANISO: SHLD CANISO         ; CANISO = CANISO + SEGTMR
                 474
                 475 ; LOAD CIRCULAR BUFFERS WITH SEGMENT START DATA
0237 2A0145      476           LHLD SEGIDX          ; OBTAIN BUFFER INDEX
023A 2600        477           MVI H,0
023C 29          478           DAD H
023D EB          479           XCHG                 ; (DE) = 2*SEGIDX
                 480
                 481 ; START_MINUTE[SEGIDX] := MINUTES
023E 2A0020      482           LHLD MINUTES
0241 44          483           MOV B,H
0242 4D          484           MOV C,L              ; BC = value to be stored in array
0243 2100CC      485           LXI H,START_MINUTE   ; HL = base of Pascal integer array
0246 19          486           DAD D                ; add SEGIDX*2
0247 71          487           MOV M,C              ; store to array
0248 23          488           INX H                ; point to other half
0249 70          489           MOV M,B              ; store to array
                 490
                 491 ; START_SUBMIN[SEGIDX] := SUBMIN
024A 2A014D      492           LHLD SUBMIN
024D 44          493           MOV B,H
024E 4D          494           MOV C,L              ; BC = value to be stored in array
024F 2100F4      495           LXI H,START_SUBMIN   ; HL = base of Pascal integer array
0252 19          496           DAD D                ; add SEGIDX*2
0253 71          497           MOV M,C              ; store to array
0254 23          498           INX H                ; point to other half
0255 70          499           MOV M,B              ; store to array
                 500
                 501 ; PP_START_TIME[SEGIDX] := PPTMR
0256 2A0027      502           LHLD PPTMR
0259 44          503           MOV B,H
025A 4D          504           MOV C,L              ; BC = value to be stored in array
025B 21007C      505           LXI H,PP_START_TIME  ; HL = base of Pascal integer array
025E 19          506           DAD D                ; add SEGIDX*2
025F 71          507           MOV M,C              ; store to array
0260 23          508           INX H                ; point to other half
0261 70          509           MOV M,B              ; store to array
                 510
                 511 ; PP_VALUE[SEGIDX] := PPINT
```

```
0262 2A0025    512              LHLD PPINT
0265 44        513              MOV B,H
0266 4D        514              MOV C,L              ; BC = value to be stored in array
0267 2100A4    515              LXI H,PP_VALUE       ; HL = base of Pascal integer array
026A 19        516              DAD D                ; add SEGIDX*2
026B 71        517              MOV M,C              ; store to array
026C 23        518              INX H                ; point to other half
026D 70        519              MOV M,B              ; store to array
               520
               521 ; RESET SEGTMR.
026E 210148    522              LXI H,SEGTMR         ; RESET SEGTMR
0271 3600      523              MVI M,0
0273 C3027F    524              JMP DONE
               525
               526 ; SEGMENT IS IN PROGRESS, SO STORE LARGEST MAGNITUDE.
0276 210007    527 CKPEAK:      LXI H,CPEAK
0279 79        528              MOV A,C
027A BE        529              CMP M
027B DA027F    530              JC DONE
027E 71        531              MOV M,C
               532
               533 ; ALL REAL-TIME DATA IS SAFELY BUFFERED, SO ENABLE INTERRUPTS.
027F FB        534 DONE:        EI
               535
               536 ; UPDATE ECG_MN_SUM & ECG_MX_SUM.
0280 2A000C    537              LHLD ECG_MN_SUM
0283 EB        538              XCHG
0284 2A014F    539              LHLD SUMBUF
0287 CD0365    540 CKMIN:       CALL CMP16
028A D20293    541              JNC CKMAX
028D 22000C    542              SHLD ECG_MN_SUM      ; SUMBUF < ECG_MN_SUM, SO STORE IT.
0290 C302A1    543              JMP CKCDPEAK
0293 EB        544 CKMAX:       XCHG                 ; SUMBUF >= ECG_MN_SUM, SO FIND IF
0294 2A000E    545              LHLD ECG_MX_SUM      ; SUMBUF > ECG_MX_SUM.
0297 CD0365    546              CALL CMP16
029A D202A1    547              JNC CKCDPEAK
029D EB        548              XCHG
029E 22001E    549              SHLD ECG_MX_SUM      ; SUMBUF > ECG_MX_SUM, SO STORE IT.
               550
               551 ; UPDATE PEAK ECG SLOPE MAGNITUDE (PEAK_BUFFER)
02A1 210022    552 CKCDPEAK:    LXI H,PEAK_BUFFER
02A4 3A014C    553              LDA SLOPE_MAG
02A7 BE        554              CMP M
02A8 DA02AC    555              JC CKCKTM
02AB 77        556              MOV M,A              ; PEAK_BUFFER ACCUMULATES PEAK_SLOPE.
               557
               558 ; COUNTDOWN CHECK_TMR AND SEND SERIAL DATA EVERY 10MS.
02AC 21001E    559 CKCKTM:      LXI H,FLAG_10MS      ; IS IT TIME TO CHECK ECG DATA?
02AF 7E        560              MOV A,M
02B0 B7        561              ORA A
02B1 CA02B8    562              JZ RESTORE
02B4 3600      563              MVI M,FALSE          ; TIME TO CHECK!
02B6 210019    564              LXI H,CHECK_TMR
02B9 35        565              DCR M
02BA C202F1    566              JNZ CKMODEM
02BD 3632      567              MVI M,CHECK_TIME     ; DO IT EVERY CHECK_TIME.
02BF 2A000C    568              LHLD ECG_MN_SUM      ; PREPARE TO COMPUTE ECG_PP.
```

```
02C2 EB          569            XCHG
02C3 2A000E      570            LHLD ECG_MX_SUM
02C6 7D          571            MOV A,L             ; [HL] - [DE] PUT INTO [HL]
02C7 93          572            SUB E
02C8 6F          573            MOV L,A
02C9 7C          574            MOV A,H
02CA 9A          575            SBB D
02CB 67          576            MOV H,A
02CC CD036B      577            CALL DIVBY5         ; ECG_PP IS NOW IN [A]
02CF 6F          578            MOV L,A             ; STORE AS A PASCAL INTEGER.
02D0 2600        579            MVI H,0
02D2 220010      580            SHLD ECG_PP
02D5 2A014F      581            LHLD SUMBUF         ; RESET ECG_MN_SUM & ECG_MX_SUM.
02D8 22000C      582            SHLD ECG_MN_SUM
02DB 22000E      583            SHLD ECG_MX_SUM
02DE 210022      584            LXI H,PEAK_BUFFER   ; GET PEAK_SLOPE
02E1 6E          585            MOV L,M
02E2 2600        586            MVI H,0             ; STORE PEAK_SLOPE AS PASCAL INTEGER.
02E4 220023      587            SHLD PEAK_SLOPE
02E7 210022      588            LXI H,PEAK_BUFFER
02EA 3600        589            MVI M,0             ; RESET PEAK_BUFFER
02EC 3E01        590            MVI A,TRUE          ; INDICATE NEW DATA IS READY.
02EE 320008      591            STA CHECK_ECG
02F1 3A015D      592 CKMODEM:   LDA XMIT_ACTIVE     ; IS MODEM ENABLED?
02F4 B7          593            ORA A
02F5 CA0328      594            JZ RESTORE
                 595
                 596 ; MODEM ENABLED, SO PREPARE ECG DATA AND CALL THE MODEM HANDLER.
02F8 3A0000      597            LDA SPIKE_ENABLED   ; DOES CASPER CARE IF PACER SPIKES ARE
02FB B7          598            ORA A               ; DETECTED?
02FC CA030B      599            JZ NOSPIKEFLG
02FF 21015E      600            LXI H,XMIT_ARTFLAG  ; SEND CODE IF PACER ARTIFACT DETECTED.
0302 7E          601            MOV A,M
0303 B7          602            ORA A               ; SET Z FLAG IF NO CODE TO BE SENT.
0304 3600        603            MVI M,FALSE
0306 3EFF        604            MVI A,SPIKE_CODE    ; INSERT CODE JUST IN CASE
0308 C20322      605            JNZ SEND_IT         ; JUMP TO SEND SPIKE_CODE IF ARTIFACT DETECTED.
030B 2A0160      606 NOSPIKEFLG: LHLD XMIT_SUMBUF   ; NO SPIKE CODE TO SEND, SO COMPUTE
030E CD036B      607            CALL DIVBY5         ; AVERAGE ECG INPUT OVER 16.67MS INTERVAL.
0311 FEFE        608            CPI 254             ; IS AVERAGE OVER 253 (0FDh)?
0313 DA031B      609            JC LT_254
0316 3EFD        610            MVI A,253           ; LIMIT TO 253.
0318 C30322      611            JMP SEND_IT
031B FE01        612 LT_254:    CPI 1               ; IS AVERAGE UNDER 1?
031D D20322      613            JNC SEND_IT
0320 3E01        614            MVI A,1             ; SET TO 1.
0322 32015F      615 SEND_IT:   STA XMIT_ECG
0325 CD00C0      616            CALL INBYTE
0328 E1          617 RESTORE:   POP H
0329 3E40        618            MVI A,01000000B     ; SO LO TO CHECK REAL TIME USE.
032B 30          619            SIM
032C D1          620            POP D
032D C1          621            POP B
032E F1          622            POP PSW
032F FB          623            EI
0331 C9          624            RET
```

```
626 ; SUBROUTINE ABSVAL -- RETURNS ABSOLUTE VALUE OF [HL]-[DE] IN [C]
627 ;   AND SETS [B] = TRUE IF [DE] > [HL]. ([B] = FALSE OTHERWISE).
628 ;   [HL] & [BC] UNCHANGED BY PROCESS. THE ABSOLUTE VALUE CAN BE SCALED
629 ;   BY HALVING ONCE OR TWICE (CONTROLLED BY ABSVAL_SCALE). IF THE
630 ;   SCALED OR UNSCALED VALUE IS GREATER THAN 255, 255 IS RETURNED.
631
0331 E5        632 ABSVAL:   PUSH H                  ; FREE HL FOR OTHER USE.
0332 0600      633          MVI B,FALSE             ; ASSUME [HL] >= [DE].
0334 7D        634          MOV A,L
0335 93        635          SUB E
0336 4F        636          MOV C,A                 ; LOW BYTE OF DIFFERENCE.
0337 7C        637          MOV A,H
0338 9A        638          SBB D
0339 D20343    639          JNC ABVDUN
033C 0601      640          MVI B,TRUE              ; BORROW OUT OF HIBYTE
033E 7B        641          MOV A,E                 ; SHOWS [DE] > [HL].
033F 95        642          SUB L
0340 4F        643          MOV C,A                 ; REDONE LOW BYTE.
0341 7A        644          MOV A,D
0342 9C        645          SBB H
0343 67        646 ABVDUN:  MOV H,A                 ; SAVE HIBYTE.
0344 3A0000    647          LDA ABSVAL_SCALE        ; SHOULD SLOPE BE HALVED?
0347 B7        648          ORA A
0348 CA035E    649          JZ ABVLIMIT
034B 6F        650          MOV L,A                 ; SAVE TO TEST AGAIN.
034C A7        651          ANA A                   ; DIVIDE DIFFERENCE BY 2.
034D 7C        652          MOV A,H
034E 1F        653          RAR
034F 67        654          MOV H,A                 ; SAVE HIBYTE.
0350 79        655          MOV A,C
0351 1F        656          RAR
0352 4F        657          MOV C,A                 ; TENTATIVE ABSOLUTE VALUE.
0353 2D        658          DCR L                   ; SHOULD SLOPE BE DIVIDED AGAIN?
0354 CA035E    659          JZ ABVLIMIT
0357 A7        660          ANA A                   ; DIVIDE IN HALF AGAIN.
0358 7C        661          MOV A,H
0359 1F        662          RAR
035A 67        663          MOV H,A
035B 79        664          MOV A,C
035C 1F        665          RAR
035D 4F        666          MOV C,A
035E 7C        667 ABVLIMIT: MOV A,H
035F E1        668          POP H
0361 B7        669          ORA A                   ; TEST DIFFERENCE HIBYTE.
0361 C8        670          RZ
0362 0EFF      671          MVI C,255               ; LIMIT RETURNED DIFFERENCE TO 255.
0364 C9        672          RET
674 ; SUBROUTINE CMP16 -- COMPARES TWO 16-BIT NUMBERS AND RETURNS WITH CARRY
675 ;   SET IF [HL] < [DE] AND ZERO SET IF [HL] = [DE]. ONLY ACCUMULATOR
676 ;   AND FLAGS CHANGED.
677
0365 7C        678 CMP16:   MOV A,H                 ; COMPARE HIGH BYTE.
0366 BA        679          CMP D
0367 C0        680          RNZ
0368 7D        681          MOV A,L                 ; HIGH BYTES IDENTICAL, SO
0369 BB        682          CMP E                   ; TEST LOW BYTES.
```

```
036A C9          683         RET
                 684
                 685
                 686
                 687 ; SUBROUTINE DIVBY5 -- DIVIDES CONTENTS OF HL BY 5 AND RETURNS RESULT
                 688 ;  IN ACCUMULATOR. HL ASSUMED LESS THAN 1276. QUOTIENT IS ALLOWED TO
                 689 ;  RANGE FROM 0 THRU 255 (0FFH). ALL REGISTERS AFFECTED.
036B 54          690 DIVBY5:  MOV D,H        ; REPLICATE HL IN DE.
036C 5D          691         MOV E,L
036D 01FB04      692         LXI B,-1276    ; IS HL>1275 ?
0370 19          693         DAD B
0371 D20377      694         JNC DO_DIV
0374 3EFF        695         MVI A,255      ; HL>1275 SO RETURN 255.
0376 C9          696         RET
0377 62          697 DO_DIV: MOV H,D        ; HL IN RANGE, SO RESTORE FROM DE.
0378 6B          698         MOV L,E
0379 AF          699         XRA A          ; CLEAR ACCUMULATOR & FLAGS.
037A 01FD80      700         LXI B,-640     ; HL=HL-640
037D 09          701         DAD B
037E DA0382      702         JC EQIV1       ; WAS INITIAL HL<640 ?
0381 EB          703         XCHG           ; RESTORE INITIAL HL<640.
0382 54          704 EQIV1:  MOV D,H        ; REPLICATE HL IN DE.
0383 5D          705         MOV E,L
0384 17          706         RAL            ; CARRY=1 IF HL WAS >639.
0385 01FEC0      707         LXI B,-320     ; HL=HL-320
0388 09          708         DAD B
0389 DA038D      709         JC EQIV2       ; NEW HL < 0 ?
038C EB          710         XCHG           ; NEW HL<0, SO USE OLD.
038D 54          711 EQIV2:  MOV D,H        ; REPLICATE HL IN DE.
038E 5D          712         MOV E,L
038F 17          713         RAL            ; CARRY=1 IF NEW HL>0.
0390 01FF60      714         LXI B,-160
0393 09          715         DAD B
0394 DA0398      716         JC EQIV3       ; NEW HL < 0 ?
0397 EB          717         XCHG           ; NEW HL<0, SO USE OLD.
0398 54          718 EQIV3:  MOV D,H        ; REPLICATE HL IN DE.
0399 5D          719         MOV E,L
039A 17          720         RAL            ; CARRY=1 IF NEW HL>0.
039B 01FFB0      721         LXI B,-80
039E 09          722         DAD B
039F DA03A3      723         JC EQIV4       ; NEW HL < 0 ?
03A2 EB          724         XCHG           ; NEW HL<0, SO USE OLD.
03A3 54          725 EQIV4:  MOV D,H        ; REPLICATE HL IN DE.
03A4 5D          726         MOV E,L
03A5 17          727         RAL            ; CARRY=1 IF NEW HL>0.
03A6 01FFD8      728         LXI B,-40
03A9 09          729         DAD B
03AA DA03AE      730         JC EQIV5       ; NEW HL < 0 ?
03AD EB          731         XCHG           ; NEW HL<0, SO USE OLD.
03AE 54          732 EQIV5:  MOV D,H        ; REPLICATE HL IN DE.
03AF 5D          733         MOV E,L
03B0 17          734         RAL            ; CARRY=1 IF NEW HL>0.
03B1 01FFEC      735         LXI B,-20
03B4 09          736         DAD B
03B5 DA03B9      737         JC EQIV6       ; NEW HL < 0 ?
03B8 EB          738         XCHG           ; NEW HL<0, SO USE OLD.
```

```
03B9 54        739 EQIV6:    MOV D,H          ; REPLICATE HL IN DE.
03BA 5D        740           MOV E,L
03BB 17        741           RAL              ; CARRY=1 IF NEW HL>0.
03BC 01FFF6    742           LXI B,-10
03BF 09        743           DAD B
03C0 DA03C4    744           JC EQIV7
03C3 EB        745           XCHG             ; NEW HL<0, SO USE OLD.
03C4 17        746 EQIV7:    RAL              ; REPLICATION UN-NESSARY
03C5 01FFFB    747           LXI B,-5         ; ON LAST CYCLE.
03C8 09        748           DAD B
03C9 17        749           RAL              ; A = QUOTIENT !!
03CA C9        750           RET
               752 ; SUBROUTINE ENABLE_75 -- INITIALIZES VARIABLES USED BY SAMPLER,
               753 ;   SETS SAMPLE_ON TRUE, UNMASKS THE RST 7.5 INTERRUPT,
               754 ;   AND ENABLES INTERRUPTS.
               755
03CB F5        756 ENABLE_75: PUSH PSW
03CC E5        757           PUSH H
03CD AF        758           XRA A            ; INITIALIZE CONTROL BYTES TO ZERO
03CE 320003    759           STA CANDIDATE_FLAG ; OR FALSE.
03D1 320029    760           STA PSFLAG
03D4 32002B    761           STA SEFLAG
03D7 32001E    762           STA FLAG_10MS
03DA 320001    763           STA ARTFLAG
03DD 32015E    764           STA XMIT_ARTFLAG
03E0 320148    765           STA SEGTMR
03E3 320145    766           STA SEGIDX
03E6 320144    767           STA SEGCNT
03E9 320002    768           STA BUFFER_LEVEL
03EC 320007    769           STA CD_PEAK
03EF 320022    770           STA PEAK_BUFFER
03F2 320008    771           STA CHECK_ECG
03F5 3E32      772           MVI A,CHECK_TIME ; INITIALIZE CHECK_TMR.
03F7 320009    773           STA CHECK_TMR
03FA 3E01      774           MVI A,1
03FC 320010    775           STA ABSVAL_SCALE ; DIFFERENTIAL WILL BE HALVED ONCE.
03FF 3E01      776           MVI A,TRUE       ; INITIALIZE CONTROL BYTES TRUE.
0401 32015D    777           STA XMIT_ACTIVE  ; SEND DATA VIA MODEM.
0404 32002A    778           STA SAMPLE_ON    ; TELL BACKGROUND ECG IS BEING SAMPLED.
0407 210000    779           LXI H,0          ; SET DOUBLE BYTES TO ZERO.
040A 220005    780           SHLD CANISO
040D 220146    781           SHLD SEGISO
0410 220020    782           SHLD MINUTES
0413 22014D    783           SHLD SUBMIN
0416 220010    784           SHLD ECG_PP
0419 220023    785           SHLD PEAK_SLOPE
041C 217FFF    786           LXI H,7FFFH      ; SET DOUBLE BYTES TO 32767D.
041F 220025    787           SHLD PPINT
0422 220027    788           SHLD PPTMR
0425 210080    789           LXI H,128        ; INITIALIZE ECG BUFFERS.
0428 220012    790           SHLD EIN0
042B 220014    791           SHLD EIN1
042E 220016    792           SHLD EIN2
0431 220018    793           SHLD EIN3
0434 22001A    794           SHLD EIN4
0437 220151    795           SHLD SUMIN0
043A 220153    796           SHLD SUMIN1
```

```
043D 220155   797            SHLD SUMIN2
0440 220157   798            SHLD SUMIN3
0443 220159   799            SHLD SUMIN4
0446 22015B   800            SHLD SUMIN5
0449 22014F   801            SHLD SUMBUF
044C 22800C   802            SHLD ECG_MN_SUM
044F 22800E   803            SHLD ECG_MX_SUM
0452 220160   804            SHLD XMIT_SUMBUF
0455 210039   805            LXI H,ESTORG    ; INITIALIZE ECG INPUT HANDLER.
0458 22001C   806            SHLD EINPTR
045B 2100C7   807            LXI H,DIFF0     ; INITIALIZE ECG DIFFERENTIAL.
045E 22000A   808            SHLD DIFPTR
0461 F3      809            DI
0462 20      810            RIM              ; GET RST 6.5 AND 5.5 MASKS.
0463 E603    811            ANI 00000011B    ; UNMASK 7.5.
0465 F618    812            ORI 00011000B    ; CLEAR 7.5 F/F AND ENABLE MASK SET.
0467 30      813            SIM
0468 FB      814            EI               ; START SAMPLING !!
0469 E1      815            POP H
046A F1      816            POP PSW
046B C9      817            RET
             818
             819
             820
             821 ; SUBROUTINE DISABLE_75 -- MASKS RST 7.5 (BUT PRESERVES INTERRUPT
             822 ;   STATUS) AND SETS SAMPLE_ON FALSE.
             823
046C F5      824 DISABLE_75: PUSH PSW
046D E5      825            PUSH H
046E AF      826            XRA A            ; 0 MEANS FALSE.
046F 32002A   827            STA SAMPLE_ON   ; TELL BACKGROUND ECG NOT BEING SAMPLED.
0472 32015D   828            STA XMIT_ACTIVE ; SEND NO DATA.
0475 20      829            RIM              ; GET RST 6.5 AND 5.5 MASKS AND STATUS.
0476 F3      830            DI
0477 67      831            MOV H,A          ; SAVE MASKS AND STATUS.
0478 E603    832            ANI 00000011B    ; PRESERVE 6.5 & 5.5 STATUS.
047A F61C    833            ORI 00011100B    ; CLEAR 7.5 F/F AND SET 7.5 MASK.
047C 30      834            SIM
047D 7C      835            MOV A,H          ; TEST INTERRUPT STATUS.
047E E608    836            ANI 00001000B
0481 CA0484   837            JZ INTR_OFF
0483 FB      838            EI               ; ENABLE ONLY IF PREVIOUSLY ENABLED.
0484 E1      839 INTR_OFF:  POP H
0485 F1      840            POP PSW
0486 C9      841            RET
             842
             843
             844
             845 ; SUBROUTINE MODEM_ON -- TURNS ON DATA TRANSMISSION ASSUMING THAT
             846 ;   SAMPLER (RST 7.5) IS ACTIVE.
0487 F5      847 MODEM_ON:  PUSH PSW
0488 3E01    848            MVI A,TRUE
048A 32015D   849            STA XMIT_ACTIVE
048D F1      850            POP PSW
048E C9      851            RET
             852
             853
```

```
                            854
                            855 ; SUBROUTINE MODEM_OFF -- TURNS OFF DATA TRANSMISSION AND LEAVES
                            856 ;   SAMPLER (RST 7.5) ACTIVE.
    048F F5                 857 MODEM_OFF: PUSH PSW
    0490 AF                 858            XRA A
    0491 32015D             859            STA XMIT_ACTIVE
    0494 F1                 860            POP PSW
    0495 C9                 861            RET

Errors=  0

FILE: RSENSL:BOBBS:     HP 64100 - Pascal    "8085" Code Generator 1 0000  1   "8085"
   2 0000  1   PROGRAM RSENSE;
   3 0000  1   $EXTENSIONS ON$
   4 0000  1   $SEPARATE ON$
   5 0000  1   $OPTIMIZE OFF$
   6 0000  1
   7 0000  1   { THIS MODULE CONTAINS THE QRS SEGMENT DEFINER AND QRS DETECTOR.
   8 0000  1     PROCEDURES IN THIS MODULE ARE CALLED FROM OTHER MODULES. }
   9 0000  1
  10 0000  1
  11 0000  1   CONST
  12 0000  1      MAX_SEGIDX = 19;   {MAXIMUM VALUE OF SEGIDX IN MODULE SAMPLER}
  13 0000  1      RR_AVENUM = 4;     {NUMBER OF R-Rs AVERAGED TO COMPUTE RATE}
  14 0000  1
  15 0000  1
  16 0000  1   CONST   {TIME LIMITS FOR 300HZ A/D SAMPLE RATE}
  17 0000  1      T_20MS  = 6;
  18 0000  1      T_80MS  = 24;
  19 0000  1      T_100MS = 30;
  20 0000  1      T_120MS = 36;
  21 0000  1      T_160MS = 48;
  22 0000  1      T_180MS = 54;
  23 0000  1      T_200MS = 60;
  24 0000  1      T_260MS = 78;
  25 0000  1      T_300MS = 90;
  26 0000  1      T_340MS = 102;
  27 0000  1      T_600MS = 180;
  28 0000  1      T_1000MS = 300;
  29 0000  1
  30 0000  1
  31 0000  1   $EXTVAR ON$
  32 0000  1   VAR
  33 0000  1      BUFFER_LEVEL   : BYTE;
  34 0000  1      CANDIDATE_FLAG : BOOLEAN;
  35 0000  1      CANDIDATE_PTR  : BYTE;
  36 0000  1      INSIGT         : BYTE;
  37 0000  1      MINUTES        : INTEGER;
  38 0000  1      SIGT           : BYTE;
  39 0000  1      {THE FOLLOWING ARRAYS CONSTITUTE THE SEGMENT BUFFER}
  40 0000  1      END_TIME       : ARRAY[0..MAX_SEGIDX] OF INTEGER;
  41 0000  1      PEAK_MAG       : ARRAY[0..MAX_SEGIDX] OF INTEGER;
  42 0000  1      START_MINUTE   : ARRAY[0..MAX_SEGIDX] OF INTEGER;
  43 0000  1      START_SUBMIN   : ARRAY[0..MAX_SEGIDX] OF INTEGER;
```

```
44 0000  1     START_TIME     : ARRAY[0..MAX_SEGIDX] OF INTEGER;
45 0000  1     $EXTVAR OFF$
46 0000  1
47 0000  1
48 0000  1     $GLOBVAR ON$
49 0000  1     VAR  (GLOBAL VARIABLES DEFINED IN THIS MODULE)
50 0000  1       R_WAVE_TYPE : BYTE;
51 0001  1           ( INDICATES HOW MANY R-R INTERVALS IN RR_BUFFER MAY NOT BE
52 0001  1             CONSECUTIVE BECAUSE NOISE-CONTAMINATED INTERVALS WERE DROPPED. )
53 0001  1
54 0001  1
55 0001  1       (LOCAL VARIABLES DEFINED IN THIS MODULE)
56 0001  1       AVERAGE_CPM : INTEGER;
57 0003  1           ( RUNNING AVERAGE OF COMPLEX PEAK_MAG -- USED TO
58 0003  1             MECHANIZE ADAPTIVE SENSING THRESHOLD )
59 0003  1       AVERAGED_RR : INTEGER;
60 0005  1           ( RUNNING AVERAGE OF VALID R-R INTERVALS (UPDATED
61 0005  1             BY QRS_DETECTED) )
62 0005  1       COMPLEX_PEAK_MAG : INTEGER;
63 0007  1           ( PEAK MAGNITUDE OF THE BAND-LIMITED DIFFERENTIAL
64 0007  1             DURING A QRS COMPLEX )
65 0007  1       LAST_MINUTE : INTEGER;
66 0009  1           ( VALUE OF SYSTEM TOC MINUTE COUNTER AT LAST
67 0009  1             QRS DETECTED )
68 0009  1       LAST_SUBMIN : INTEGER;
69 000B  1           ( VALUE OF SYSTEM TOC SUB-MINUTE COUNTER AT LAST
70 000B  1             QRS DETECTED )
71 000B  1       MAXIMUM_ST,MINIMUM_ST : INTEGER;
72 000F  1           ( S-T INTERVAL RANGES -- USED TO REJECT T-WAVES )
73 000F  1       Q_PTR, R_PTR, T1_PTR, T2_PTR : BYTE;
74 0013  1           ( SEGMENT BUFFER POINTERS USED IN THE QRS DETECTION & SHAPE
75 0013  1             MEASUREMENT PROCESS -- Q_PTR EVENTUALLY INDICATES THE Q-R SEGMENT
76 0013  1             AND R_PTR EVENTUALLY INDICATES THE R-S SEGMENT )
77 0013  1       QS_INTERVAL : INTEGER;
78 0015  1           ( APPROXIMATION OF THE Q-S INTERVAL OF A QRS COMPLEX
79 0015  1             (EXACT IF THERE ARE NO NOTCHES AND NO PROMINENT
80 0015  1             Q- OR S-WAVES) )
81 0015  1       RATIO : INTEGER;
82 0017  1           ( RATIO BETWEEN LEADING AND TRAILING PEAK SLOPES OF A QRS )
83 0017  1       RR_BUFFER : ARRAY[1..RR_AVENUM] OF INTEGER;
84 001F  1           ( BUFFER USED TO ACCUMULATE R-R INTERVALS FOR AVERAGE RATE. )
85 001F  1       RR_INTERVAL : INTEGER;
86 0021  1           ( BUFFER USED TO TRANSFER R-R INTERVAL DATA )
87 0021  1       RR_PRIOR, RR_CURRENT : INTEGER,
88 0025  1           ( CIRCULAR BUFFER OF TWO MOST RECIENT R-R INTERVALS )
89 0025  1       RR_PTR : BYTE;
90 0026  1           ( POINTER TO ELEMENTS OF RR_BUFFER )
91 0026  1       TEMP1(TEMP_A1),TEMP2(TEMP_B1),TEMP3(TEMP_B2),TEMP4(TEMP_B3) : INTEGER;
92 002E  1           ( TEMPORARY STORAGE FOR NON-REAL-TIME TASKS )
93 002E  1       T_WAVE_LIMIT : INTEGER;
94 0030  1           ( MAXIMUM VALUE OF PEAK_MAG THAT WILL BE INTERPRETED
95 0030  1             AS A T-WAVE IF IT IS WITHIN THE SENSING REFRACTORY )
96 0030  1       RS_M1,RS_M2,RS_M3 : INTEGER;
97 0036  1     $GLOBVAR OFF$
98 0000  1
99 0000  1
100 0000 1    FUNCTION DELTA (BASE,CHANGE : INTEGER) : INTEGER;
```

```
101 0009  2     ( RETURNS A LIMITED INCREMENT TO BE ADDED TO
102 0009  2       (OR SUBTRACTED FROM) THE BASE TO LET IT ULTIMATELY
103 0009  2       REACH THE TARGET -- USED IN ADAPTIVE TRACKING. )
104 0009  2     BEGIN
105 0009  2       IF CHANGE > BASE
106 0016  2         THEN CHANGE := BASE; (SET UPPER LIMIT)
107 0019  2       CHANGE := SHIFT(CHANGE,-3);
108 0024  2       IF CHANGE > 0
109 002D  2         THEN DELTA := CHANGE
110 0033  2         ELSE DELTA := 1; (LOWER LIMIT)
111 0039  2     END; (DELTA)
112 0000  1
113 0000  1
114 0000  1   FUNCTION UPDATE (BASE,TARGET : INTEGER) : INTEGER;
115 004C  2     ( ADAPTIVELY TRACKS THE BASE VALUE OF A PARAMETER TOWARD
116 004C  2       A MOVING TARGET. )
117 004C  2     BEGIN
118 004C  2       IF TARGET > BASE
119 0059  2         THEN UPDATE := BASE + DELTA(BASE, (TARGET - BASE))
120 0071  2         ELSE UPDATE := BASE - DELTA(BASE, (BASE - TARGET));
121 0090  2     END; (UPDATE)
122 0000  1
123 0000  1
124 0000  1   PROCEDURE SET_THRESHOLDS (REFERENCE_MAG : INTEGER);
125 00A3  2     ( UPDATES QRS SEGMENT SENSING THRESHOLDS )
126 00A3  2     BEGIN
127 00A3  2       IF REFERENCE_MAG < 24
128 00AF  2         THEN REFERENCE_MAG := 24; (KEEP INSIGT >= 3)
129 00B3  2       IF REFERENCE_MAG > 255
130 00BF  2         THEN REFERENCE_MAG := 255; (MAXIMUM POSSIBLE PEAK_MAG)
131 00C3  2       AVERAGE_CPM := REFERENCE_MAG;
132 00C9  2       INSIGT := SHIFT(REFERENCE_MAG,-3);
133 00D2  2       SIGT := INSIGT + INSIGT + INSIGT;
134 00DA  2     END; (SET_THRESHOLDS)
135 0000  1
136 0000  1
137 0000  1   FUNCTION BPM (INTERVAL : INTEGER) : INTEGER;
138 00E8  2     ( COMPUTES THE RATE EQUIVALENT TO AN R-R INTERVAL
139 00E8  2       MEASURED IN TICKS OF A 300HZ SAMPLE CLOCK. SCALE FACTOR
140 00E8  2       IS 1 BIT PER BPM, WITH RATES NOT COMPUTED FOR INTERVALS
141 00E8  2       SHORTER THAN 100MS. COMPUTATION INCLUDES ROUNDOFF. )
142 00E8  2     BEGIN
143 00E8  2       IF (INTERVAL > 18000) OR (INTERVAL < T_100MS)
144 00FC  2         THEN BPM := 0 ( OVERFLOW PROTECTION )
145 0105  2         ELSE BPM := (18000 + SHIFT(INTERVAL,-1)) DIV INTERVAL;
146 011B  2     END; (BPM)
147 0000  1
148 0000  1
149 0000  1   FUNCTION NEWER (CURRENT_PTR : BYTE) : BYTE;
150 012C  2     ( RETURN POINTER TO LOCATION IN SEGMENT BUFFER ONE CELL
151 012C  2       "LATER" THAN CURRENT_PTR )
152 012C  2     BEGIN
153 012C  2       IF CURRENT_PTR = MAX_SEGIDX
154 0134  2         THEN NEWER := 0
155 013C  2         ELSE NEWER := CURRENT_PTR + 1;
156 0144  2     END; (NEWER)
157 0000  1
```

```
158 0080  1
159 0000  1  FUNCTION OLDER (CURRENT_PTR : BYTE) : BYTE;
160 0156  2    ( RETURN POINTER TO LOCATION IN SEGMENT BUFFER ONE CELL
161 0156  2      "EARLIER" THAN CURRENT_PTR )
162 0156  2  BEGIN
163 0156  2    IF CURRENT_PTR = 0
164 015E  2      THEN OLDER := MAX_SEGIDX
165 0166  2      ELSE OLDER := CURRENT_PTR - 1;
166 016E  2  END; (OLDER)
167 0000  1
168 0000  1
169 0000  1  FUNCTION ISOLATED (SEG_PTR : BYTE) : BOOLEAN;
170 0180  2    ( RETURNS TRUE IF SEGMENT IS ISOLATED FROM PRIOR SEGMENTS )
171 0180  2  BEGIN
172 0180  2    IF START_TIME[SEG_PTR] ) T_100MS
173 0197  2      THEN ISOLATED := TRUE
174 019F  2      ELSE ISOLATED := FALSE;
175 01A4  2  END; (ISOLATED)
176 0000  1
177 0000  1
178 0000  1  FUNCTION DELTA_TOC (MINUTE,SUBMINUTE : INTEGER) : INTEGER;
179 0006  2    ( FINDS THE DIFFERENCE BETWEEN THE TOC PASSED AS PARAMETERS AND THE
180 0006  2      TOC STORED IN THE SEGMENT BUFFER AT R_PTR. IT IS ASSUMED THAT
181 0006  2      TOC(PASSED) ( TOC (AT R_PTR). THE VALUE RETURNED IS THE DIFFERENCE
182 0006  2      IN SAMPLE COUNTS; IF THE DIFFERENCE IS GREATER THAN ONE MINUTE,
183 0006  2      18000 IS RETURNED )
184 0006  2  VAR
185 0006  2    BORROW : INTEGER;  (CONTAINS SUBMINUTES BORROWED FROM MINUTES)
186 01B6  2  BEGIN
187 01B6  2    BORROW := 0;
188 01BC  2    IF START_SUBMIN[R_PTR] ( SUBMINUTE
189 01D3  2      THEN BEGIN  (BORROW FROM MINUTES)
190 01D3  2        MINUTE := MINUTE + 1;
191 01DD  2        BORROW := 18000;
192 01E3  2      END; (BORROW FROM MINUTES)
193 01E3  2    IF MINUTE ( START_MINUTE[R_PTR]
194 01FE  2      THEN DELTA_TOC := 18000
195 0207  2      ELSE DELTA_TOC := (START_SUBMIN[R_PTR] + BORROW) - SUBMINUTE;
196 0223  2  END; (DELTA_TOC)
197 0000  1
198 0000  1
199 0000  1  $GLOBPROC ON$
200 0000  1
201 0000  1
202 0000  1  PROCEDURE INIT_RATE_MNTR;
203 022D  2    ( INITIALIZES THE R-WAVE SENSING ALGORITHM. )
204 022D  2  BEGIN
205 022D  2    LAST_MINUTE := MINUTES;
206 0233  2    CANDIDATE_FLAG := FALSE;
207 0238  2    R_WAVE_TYPE := 0;
208 023D  2    RR_PTR := 1;
209 0242  2    AVERAGED_RR := T_1000MS;
210 0248  2    MINIMUM_ST := T_340MS;
211 024E  2    MAXIMUM_ST := T_600MS;
212 0254  2    SET_THRESHOLDS(60);
213 0259  2  END; (INIT_RATE_MNTR)
214 0000  1
```

```
215 0000  1
216 0000  1  FUNCTION AVERAGE_RATE : BYTE;
217 0001  2    ( COMPUTES THE AVERAGE RATE AND RETURNS VALUES BETWEEN 40 & 127 )
218 0001  2  VAR
219 0001  2    TEMPINT : INTEGER;
220 0003  2    TMPTR : BYTE;
221 025C  2  BEGIN
222 025C  2    TEMPINT := 0;
223 0262  2    FOR TMPTR := 1 TO RR_AVENUM DO TEMPINT := TEMPINT + RR_BUFFER[TMPTR];
224 0295  2    TEMPINT := TEMPINT DIV RR_AVENUM;
225 02A2  2    RS_M1 := TEMPINT;
226 02A5  2    TEMPINT := BPM(TEMPINT);
227 02AD  2    RS_M2 := TEMPINT;
228 02B0  2    IF TEMPINT > 127
229 02B9  2      THEN AVERAGE_RATE := 127
230 02C1  2      ELSE BEGIN
231 02C1  2        IF TEMPINT > 40
232 02CD  2          THEN AVERAGE_RATE := TEMPINT
233 02D4  2          ELSE AVERAGE_RATE := 40;
234 02D9  2      END;
235 02D9  2  END; (AVERAGE_RATE)
236 0000  1
237 0000  1
238 0000  1  FUNCTION QRS_DETECTED : BOOLEAN;
239 0000  2    ( A NON-REAL-TIME PROCEDURE THAT EVALUATES SEGMENT
240 0000  2      BUFFER CONTENTS TO DECIDE WHETHER A BONAFIDE
241 0000  2      QRS HAS OCCURRED AND TO DETERMINE ITS PARAMETERS. )
242 0000  2  LABEL 3333; (EXIT TO END OF QRS_DETECTED WITHOUT FURTHER COMPUTATION)
243 02DE  2  BEGIN
244 02DE  2    IF CANDIDATE_FLAG = FALSE
245 02E6  2      THEN BEGIN
246 02E6  2        QRS_DETECTED := FALSE;
247 02EB  2        GOTO 3333;
248 02EE  2      END
249 02F1  2      ELSE BEGIN  (TEST CANDIDATE)
250 02F1  2        RS_M3 := 1;
251 02F7  2        CANDIDATE_FLAG := FALSE;
252 02FC  2        T2_PTR := CANDIDATE_PTR;
253 0302  2        IF BUFFER_LEVEL > 10
254 030D  2          THEN BEGIN  ( SUBSEQUENT ENTRIES INTO SEGMENT BUFFER MAY
255 030D  2                        HAVE OVERWRITTEN QRS DATA )
256 030D  2            R_WAVE_TYPE := 0;
257 0312  2            QRS_DETECTED := FALSE;
258 0317  2            GOTO 3333;
259 031A  2          END
260 031D  2          ELSE BEGIN (NO-BUFFER-OVERFLOW)
261 031D  2            IF ISOLATED(T2_PTR)
262 0325  2              THEN BEGIN  (TEST NEWER SEGMENT)
263 0325  2                ( CANDIDATE MAY BE A QRS WITH STEEP Q-R )
264 0325  2                IF ISOLATED(NEWER(T2_PTR))
265 0335  2                  THEN BEGIN (NOISE OR T-WAVE)
266 0335  2                    QRS_DETECTED := FALSE;
267 033A  2                    GOTO 3333;
268 033D  2                  END (NOISE OR T-WAVE)
269 0340  2                  ELSE BEGIN  (SIGNIFICANT QR)
270 0340  2                    R_PTR := NEWER(T2_PTR);
271 0348  2                    IF (PEAK_MAG[T2_PTR] = 0) OR (PEAK_MAG[R_PTR] = 0)
```

```
272 0373  2                        THEN BEGIN  (BUFFER BAD)
273 0373  2                            R_WAVE_TYPE := 8;
274 0378  2                            QRS_DETECTED := FALSE;
275 037D  2                            GOTO 3333;
276 0380  2                        END;  (BUFFER BAD)
277 0380  2                      END;  (SIGNIFICANT QR)
278 0380  2                    END  (TEST NEWER SEGMENT)
279 0383  2                    ELSE BEGIN  (SIGNIFICANT RS)
280 0383  2                      ( T2_PTR INDICATES "NEWEST" POSSIBLE R-S.  FIND LARGEST
281 0383  2                        OLDER SEGMENT IN GROUP AND ASSUME IT TO BE THE R-S )
282 0383  2                      IF (PEAK_MAG[OLDER(T2_PTR)] = 0)
283 0383  2                      OR (PEAK_MAG[T2_PTR] = 0)
284 03B3  2                        THEN BEGIN  (BUFFER ERROR)
285 03B3  2                            R_WAVE_TYPE := 8;
286 03B8  2                            QRS_DETECTED := FALSE;
287 03BC  2                            GOTO 3333;
288 03C0  2                        END  (BUFFER ERROR)
289 03C3  2                        ELSE BEGIN  (REFINE RS LOCATION)
290 03C3  2                            TEMP2 := 0; TEMP3 := 0; TEMP4 := 0;
291 03CF  2                            R_PTR := T2_PTR; T1_PTR := T2_PTR;
292 03DB  2                            WHILE (TEMP2 < 4)
293 03DB  2                            AND (NOT ISOLATED(T1_PTR)) DO BEGIN  (LOCATE RS)
294 03ED  2                                TEMP2 := TEMP2 + 1;
295 03F4  2                                IF PEAK_MAG[T1_PTR] > TEMP3
296 040B  2                                  THEN BEGIN  (LARGER SEGMENT)
297 040B  2                                    TEMP3 := PEAK_MAG[T1_PTR];
298 041D  2                                    R_PTR := T1_PTR;
299 0420  2                                  END;  (LARGER SEGMENT)
300 0420  2                                T1_PTR := OLDER(T1_PTR);
301 0428  2                                TEMP4 := OLDER(T1_PTR);
302 0433  2                                IF (END_TIME[TEMP4] <= T_20MS)
303 0433  2                                OR (PEAK_MAG[TEMP4] = 0)
304 0457  2                                    THEN TEMP2 := 6;  ( STOP PROCESS )
305 045A  2                            END;  (LOCATE RS)
306 045D  2                        END;  (REFINE RS LOCATION)
307 045D  2                    END;  (SIGNIFICANT RS)
308 045D  2
309 045D  2  RS_M3 := 2;
310 0463  2           ( R-PTR NOW LOCATES THE R-S, SO COMPUTE R-R & CHECK VALIDITY )
311 0463  2           RR_INTERVAL := DELTA_TOC (LAST_MINUTE,LAST_SUBMIN);
312 046D  2           IF (RR_INTERVAL < MINIMUM_ST)
313 0477  2             THEN BEGIN  (INSIDE ABSOLUTE REFRACTORY)
314 0477  2                 QRS_DETECTED := FALSE;
315 047C  2                 GOTO 3333;
316 047F  2             END;  (INSIDE ABSOLUTE REFRACTORY)
317 047F  2
318 047F  2           ( FIND Q-R AS TALLEST OF UP TO 3 SEGMENTS PRECEEDING THE R-S )
319 047F  2           T1_PTR := R_PTR;
320 0485  2           TEMP2 := 0; TEMP4 := 0;
321 048E  2           WHILE (NOT ISOLATED(T1_PTR)) AND (TEMP2 < 3)
322 048E  2           AND (PEAK_MAG[T1_PTR] > 0) DO BEGIN  (FIND Q)
323 04BA  2               TEMP2 := TEMP2 + 1;
324 04C4  2               T1_PTR := OLDER(T1_PTR);
325 04CC  2               IF (TEMP4 + INSIGT) < PEAK_MAG[T1_PTR]
326 04EE  2                 THEN BEGIN  (LARGER VALUE)
327 04EE  2                     TEMP4 := PEAK_MAG[T1_PTR];
328 0500  2                     Q_PTR := T1_PTR;
```

```
329 0503  2              END; (LARGER VALUE)
330 0503  2            END; (FIND Q)
331 0506  2
332 0506  2            ( DETERMINE MAGNITUDE OF CANDIDATE. )
333 0506  2            COMPLEX_PEAK_MAG := TEMP4;
334 050C  2            IF TEMP3 > COMPLEX_PEAK_MAG
335 0516  2               THEN COMPLEX_PEAK_MAG := TEMP3;
336 0519  2            IF (RR_INTERVAL < MAXIMUM_ST)
337 0519  2            AND (COMPLEX_PEAK_MAG < T_WAVE_LIMIT)
338 0532  2               THEN BEGIN  (LOW SIGNAL IN RELATIVE REFRACTORY)
339 0532  2                  QRS_DETECTED := FALSE;
340 0537  2                  GOTO 3333;
341 053A  2               END; (LOW SIGNAL IN RELATIVE REFRACTORY)
342 053A  2
343 053A  2 RS_M3 := 3;
344 0540  2            ( ASSUME CANDIDATE IS A QRS )
345 0540  2            PEAK_MAG[R_PTR] := 0;
346 0551  2            LAST_MINUTE := START_MINUTE[R_PTR];
347 0560  2            LAST_SUBMIN := START_SUBMIN[R_PTR];
348 056F  2            T_WAVE_LIMIT := SHIFT((3 * COMPLEX_PEAK_MAG),-2);
349 0581  2            IF R_WAVE_TYPE > 0
350 058C  2               THEN R_WAVE_TYPE := R_WAVE_TYPE - 1;
351 0594  2            IF R_WAVE_TYPE > 5
352 059F  2               THEN BEGIN  (NOISE CONTAMINATED R-R DATA)
353 059F  2                  QRS_DETECTED := FALSE;
354 05A4  2                  GOTO 3333;
355 05A7  2               END (NOISE CONTAMINATED R-R DATA)
356 05AA  2            ELSE BEGIN  (RELIABLE QRS DATA)
357 05AA  2 RS_M3 := 4;
358 05B0  2               RATIO := (100 * TEMP4) DIV TEMP3;
359 05C4  2               QS_INTERVAL := END_TIME[R_PTR]
360 05C4  2                  + DELTA_TOC(START_MINUTE[Q_PTR],START_SUBMIN[Q_PTR]);
361 05FC  2               RR_PRIOR := RR_CURRENT;
362 0612  2               RR_CURRENT := RR_INTERVAL;
363 0608  2               ( ADAPTIVELY ADJUST REFRACTORY PERIODS )
364 0608  2               AVERAGED_RR := UPDATE(AVERAGED_RR, RR_INTERVAL);
365 0612  2               MAXIMUM_ST := T_200MS + SHIFT(AVERAGED_RR,-4);
366 061E  2               TEMP1 := SHIFT(AVERAGED_RR,-2);
367 0629  2               MINIMUM_ST := T_80MS + TEMP1;
368 0630  2               IF MAXIMUM_ST < MINIMUM_ST
369 063A  2                  THEN MINIMUM_ST := MAXIMUM_ST;
370 063D  2               IF MINIMUM_ST > T_260MS
371 0649  2                  THEN MINIMUM_ST := T_260MS;
372 064D  2               IF MINIMUM_ST > SHIFT(TEMP1,1)
373 065F  2                  THEN MINIMUM_ST := SHIFT(TEMP1,1);
374 066A  2               IF TEMP1 > T_160MS
375 0676  2                  THEN TEMP1 := T_160MS;
376 067A  2               MAXIMUM_ST := TEMP1 + MINIMUM_ST;
377 0685  2               ( ADAPTIVELY ADJUST SENSITIVITY )
378 0685  2               IF RR_CURRENT >= RR_PRIOR
379 0692  2                  THEN SET_THRESHOLDS(UPDATE(AVERAGE_CPM,COMPLEX_PEAK_MAG));
380 06A1  2               RR_BUFFER[RR_PTR] := RR_CURRENT;
381 06B4  2               RR_PTR := RR_PTR + 1;
382 06B9  2               IF RR_PTR > RR_AVENUM
383 06C1  2                  THEN RR_PTR := 1;
384 06C6  2               QRS_DETECTED := TRUE;
385 06CB  2               GOTO 3333;
```

```
386 06CE  2           END; (RELIABLE QRS DATA)
387 06CE  2         END; (NO-BUFFER-OVERFLOW)
388 06CE  2       END; (TEST CANDIDATE)
389 06CE  2
390 06CE  2     3333: (EXIT AFTER QRS PROCESSING COMPLETE)
391 06CE  2
392 06CE  2     RS_M3 := 5;
393 06D4  2   END; (QRS_DETECTED)
394 0000  1
395 0000  1
396 0000  1   $GLOBPROC OFF$
397 0000  1   .
```

End of compilation, number of errors=   0

FILE: MONITOR:BO3BS:    HP 64000 - Pascal    "8085" Code Generator

```
  1 0000  1  "8085"
  2 0000  1  PROGRAM MONITOR;
  3 0000  1  $EXTENSIONS ON$
  4 0000  1  $SEPARATE ON$
  5 0000  1  $OPTIMIZE OFF$
  6 0000  1
  7 0000  1
  8 0000  1  TYPE
  9 0000  1     RM_STATE_TYPE = (RESET,WAIT,SETUP,MNTR);
 10 0000  1
 11 0000  1
 12 0000  1  VAR $EXTVAR ON$
 13 0000  1     ECG_PP       : INTEGER;  (module SAMPLER)
 14 0000  1     R_WAVE_TYPE  : BYTE;     (module RSENSE)
 15 0000  1     SAMPLE_ON    : BOOLEAN;  (module SAMPLER monitor on/off control)
 16 0000  1     $EXTVAR OFF$
 17 0000  1
 18 0000  1
 19 0000  1  VAR $GLOBVAR ON$  ( Provide communication/handshaking between rate
 20 0000  1     monitor and basestation controller background state machines. )
 21 0000  1     GV1 : BYTE;
 22 0001  1     GV2 : BYTE;
 23 0002  1     GV3 : BYTE;
 24 0003  1     GV4 : BYTE;
 25 0004  1     GV5 : BYTE;
 26 0005  1     NEW_GAIN     : BOOLEAN;  (ECG gain change handshaking)
 27 0006  1     RATE_TO_SEND : BYTE;     (ECG rate and monitor status)
 28 0007  1     $GLOBVAR OFF$
 29 0007  1
 30 0007  1
 31 0007  1  VAR $GLOBVAR ON$  ( Rate monitor state variables. )
 32 0007  1     NEXT_RM_STATE : RM_STATE_TYPE;
 33 0008  1     RM_STATE      : RM_STATE_TYPE;
 34 0009  1     $GLOBVAR OFF$
 35 0000  1
 36 0000  1
 37 0000  1  PROCEDURE INIT_RATE_MNTR;         EXTERNAL;  (module RSENSE)
 38 0000  1  FUNCTION QRS_DETECTED : BOOLEAN;  EXTERNAL;  (module RSENSE)
 39 0000  1  FUNCTION AVERAGE_RATE : BYTE;     EXTERNAL;  (module RSENSE)
 40 0000  1
```

```
41 0000  1
42 0000  1  $GLOBPROC ON$
43 0000  1
44 0000  1  PROCEDURE CURRENT_RMS_OPS;
45 0000  2    ( Carry out operations for the current rate monitor state, evaluate
46 0000  2      triggers that may cause state changes, and exit the current state. )
47 0000  2  BEGIN
48 0000  2
49 0000  2    CASE RM_STATE OF
50 0006  2
51 0006  2      WAIT:  BEGIN
52 0006  2               ( RATE_TO_SEND stays at 0 to indicate rate monitor in WAIT.
53 0006  2                 Leave WAIT when patient basestation wants data sent. )
54 0006  2               IF SAMPLE_ON
55 000D  2                 THEN NEXT_RM_STATE := SETUP;
56 0012  2             END; (WAIT)
57 0015  2
58 0015  2      SETUP: BEGIN
59 0015  2  GV1 := 0;
60 001A  2               ( Real-time process samples ECG and sends a byte to Casper
61 001A  2                 every 10MS. ECG amplitude is tested -- system will not
62 001A  2                 leave SETUP if ECG amplitude is under 60 sample units p-p.
63 001A  2                 QRS detection occurs to let algorithm stabilize and load
64 001A  2                 the rate computation buffer. RATE_TO_SEND is held at 1
65 001A  2                 if ECG amplitude is under 60 units p-p, and at 2 if ECG
66 001A  2                 amplitude is adedquate. Leave SETUP if sampling is to stop
67 001A  2                 or after ECG amplitude is satisfactory and QRS detection
68 001A  2                 has stabilized. )
69 001A  2               IF QRS_DETECTED
70 0020  2                 THEN RATE_TO_SEND := RATE_TO_SEND; (Detector stabilizes)
71 0026  2               IF R_WAVE_TYPE = 0
72 002E  2                 THEN NEXT_RM_STATE := MNTR;
73 0033  2               IF NOT SAMPLE_ON
74 003A  2                 THEN NEXT_RM_STATE := WAIT;
75 003F  2  GV1 := 1;
76 0044  2             END; (SETUP)
77 0047  2
78 0047  2      MNTR:  BEGIN
79 0047  2  GV2 := 0;
80 004C  2               ( Real-time process samples ECG and sends a byte to Casper
81 004C  2                 every 10MS. ECG amplitude is tested and QRS detection
82 004C  2                 occurs. R-R data is used to compute RATE_TO_SEND as the
83 004C  2                 average rate of the six most recent beats unless ECG
84 004C  2                 amplitude stays under 35 sample units p-p or no QRSs are
85 004C  2                 detected for 4 seconds. RATE_TO_SEND will be set to 3 if
86 004C  2                 ECG amplitude is low and set to 4 if no QRS are detected.
87 004C  2                 Leave MNTR if sampling is to stop or if ECG gain has been
88 004C  2                 changed by the basestation controller. )
89 004C  2               IF QRS_DETECTED
90 0052  2                 THEN RATE_TO_SEND := AVERAGE_RATE;
91 0058  2               IF NOT SAMPLE_ON
92 005F  2                 THEN NEXT_RM_STATE := WAIT;
93 0064  2  GV2 := 1;
94 0069  2             END; (MNTR)
95 006C  2
96 006C  2      RESET: BEGIN
97 006C  2               (This is a transitional initialization state)
```

```
98 106C  2              NEXT_RM_STATE := WAIT;
99 1071  2            END; (RESET)
100 0074 2
101 0074 2      OTHERWISE NEXT_RM_STATE := RESET; (Fault recovery)
102 0079 2
103 0079 2      END; (CASE RM_STATE OF)
104 0093 2
105 0093 2   END; (CURRENT_RMS_OPS)
106 0000 1
107 0000 1
108 0000 1
109 0000 1   PROCEDURE CHANGE_RMS;
110 0094 2      ( Initialize new rate monitor states. )
111 0094 2   BEGIN
112 0094 2
113 0094 2      CASE NEXT_RM_STATE OF
114 009A 2
115 009A 2      WAIT:   BEGIN
116 009A 2                 (Sampling already off, so indicate to Casper that
117 009A 2                 rate monitor is in WAIT)
118 009A 2                 RATE_TO_SEND := 39;
119 009F 2              END; (WAIT)
120 00A2 2
121 00A2 2      SETUP:  BEGIN
122 00A2 2                 ( Real-time sampling is on. Initialize QRS detection
123 00A2 2                 and rate averaging. Indicate that SETUP is initiated. )
124 00A2 2                 INIT_RATE_MNTR;
125 00A5 2                 RATE_TO_SEND := 39;
126 00AA 2              END; (SETUP)
127 00AD 2
128 00AD 2      MNTR:   BEGIN
129 00AD 2                 ( No special initialization needed -- processes are
130 00AD 2                 initialized when SETUP runs. )
131 00AD 2              END; (MNTR)
132 00B0 2
133 00B0 2      OTHERWISE NEXT_RM_STATE := RESET; (Fault recovery)
134 00B5 2
135 00B5 2      END; (CASE NEXT_RM_STATE OF)
136 00CA 2
137 00CA 2   END; (CHANGE_RMS)
138 0000 1
139 0000 1   $GLOBPROC OFF$
140 0000 1   .
```

End of compilation, number of errors=    0
FILE: INTR:BOBSS1        HEWLETT-PACKARD: 8085 Assembler

LOCATION OBJECT CODE LINE     SOURCE LINE

```
                      1  "8085"
                      2
                      3  ; THESE ARE THE LOW LEVEL INTERRUPT HANDLERS
                      4
                      5        CLB    DISABLE
                      6        CLB    ENABLE
                      7        CLB    SMASK
```

```
                    8            CLB     RMASK
                    9            CLB     ISR55
                   10
                   11            EXT     SM              ; STATE MACHINE MODULE
                   12            EXT     SAMPLER
                   13            EXT     XECOM_DATA
                   14            EXT     TICK
                   15            EXT     INTRSTS
                   16            EXT     INTRMSK
                   17            EXT     CTC_0
                   18
                   19 ; RESET VECTOR
                   20            ORG     0006H
0000 C30000        21            JMP     SM
                   22
                   23 ; RST 5.5 VECTOR
                   24 ; 1 SECOND INTERRUPT
                   25            ORG     02CH
002C C300OE        26            JMP     ISR55
                   27
                   28 ; RST 6.5 VECTOR
                   29 ; TXRDY FROM THE XECOM
                   30            ORG     034H
0034               31 MY034
0034 C30034        32            JMP     MY034
                   33
                   34 ; RST 7.5 VECTOR
                   35 ; 300 HZ SAMPLING INTERRUPT
                   36            ORG     03CH
003C C30000        37            JMP     SAMPLER
                   39 ; PROGRAM AREA
                   40            PROG
                   41
0000               42 DISABLE
0000 F3            43            DI
0001 C9            44            RET
                   45
0002               46 ENABLE
0002 FB            47            EI
0003 C9            48            RET
                   49
0004               50 SMASK
0004 3A0010        51            LDA     INTRMSK
0007 30            52            SIM
0008 C9            53            RET
                   54
0009               55 RMASK
0009 20            56            RIM
000A 320000        57            STA     INTRSTS
000D C9            58            RET
                   59
                   60
000E               61 ISR55
000E F5            62            PUSH    PSW
                   63 ;
                   64 ;   RESTART THE TIMER
                   65 ;
```

```
00 0F 3E2C          66        MVI      A,120H
0011 320100         67        STA      CTC_0
0014 3E01           68        MVI      A,100H
0016 320100         69        STA      CTC_0
0019 C5             70        PUSH     B
001A D5             71        PUSH     D
001B E5             72        PUSH     H
                    73     ;
001C CD0000         74        CALL     TICK
                    75     ;
001F E1             76        POP      H
0020 D1             77        POP      D
0021 C1             78        POP      B
0022 F1             79        POP      PSW
                    80
0023 FB             81        EI
-1024 C9            82        RET
                    83
                    84
                    85
                    86        END
```

Errors= 0

In connection with the above description, we claim:

1. A telemetry base station, comprising:
radio receiver means for receiving telemetered radio signals containing physiological information;
modem means for transmitting and receiving digital signals, said modem means adapted to be coupled to a telephone line;
a telephone set adapted to be coupled to said telephone line for voice communication;
command decoding means for decoding the presence of command signals within said digital signals received by said modem means;
control means coupled to said command decoding means for coupling and uncoupling said telephone set from said telephone line, and for inhibiting transmission of digital signals from said modem while said telephone set is coupled to said telephone line in accordance with said command signals detected within said signals received by said modem means;
signal means for providing simulated call progress signals to the telephone set when the telephone set is uncoupled from the telephone line and the modem means is transmitting digital signals; and
A/D converter means coupled to said receiver means and to said modem means for converting said radio frequency signals received by said receiver means to digital signals for transmission by said modem means.

2. A base station according to claim 1 wherein said control means is also coupled to said telephone set and in response to said telephone going off hook, provides said modem means with a digital signal for transmission from said modem, indicating that said telephone set has gone off hook.

3. A telemetry base station, comprising:
radio receiver means for receiving telemetered radio signals containing physiological information;
modem means for transmitting and receiving digital signals, said modem means adapted to be coupled to a telephone line;
a telephone set adapted to be coupled to said telephone line for voice communication;
means for providing a signal which indicates when the telephone set is off hook;
command decoding means for decoding the presence of a command signal within said digital signals received by said modem means which indicates a desire on behalf of a source of the digital signals received by the modem means for voice communication;
means coupled to said command decoding means for coupling the telephone set from said telephone line during a voice communication mode and decoupling the telephone set from the telephone line during a data communication mode, based upon the command signals;
means for causing simulated operation of the telephone set during the data communication mode; and
A/D converter means coupled to said receiver means and to said modem means for converting said radio frequency signals received by said receiver means to digital signals for transmission by said modem means.

* * * * *